US010883980B2

(12) United States Patent
Ploss et al.

(10) Patent No.: US 10,883,980 B2
(45) Date of Patent: Jan. 5, 2021

(54) METHODS AND COMPOSITIONS FOR INHIBITING HEPATITIS E VIRUS

(71) Applicant: The Trustees of Princeton University, Princeton, NJ (US)

(72) Inventors: Alexander Ploss, Princeton, NJ (US); Qiang Ding, Princeton, NJ (US)

(73) Assignee: The Trustees of Princeton University, Princeton, NJ (US)

( * ) Notice: Subject to any disclaimer, the term of this patent is extended or adjusted under 35 U.S.C. 154(b) by 0 days.

(21) Appl. No.: 16/334,174

(22) PCT Filed: Sep. 21, 2017

(86) PCT No.: PCT/US2017/052769
§ 371 (c)(1),
(2) Date: Mar. 18, 2019

(87) PCT Pub. No.: WO2018/057773
PCT Pub. Date: Mar. 29, 2018

(65) Prior Publication Data
US 2019/0204297 A1 Jul. 4, 2019

Related U.S. Application Data

(60) Provisional application No. 62/398,297, filed on Sep. 22, 2016.

(51) Int. Cl.
*C12Q 1/68* (2018.01)
*G01N 33/50* (2006.01)
*C12Q 1/6897* (2018.01)
*C12Q 1/70* (2006.01)
*A61K 38/00* (2006.01)
*A61K 31/00* (2006.01)

(52) U.S. Cl.
CPC ........... *G01N 33/502* (2013.01); *A61K 31/00* (2013.01); *A61K 38/00* (2013.01); *C12Q 1/6897* (2013.01); *C12Q 1/706* (2013.01)

(58) Field of Classification Search
None
See application file for complete search history.

(56) References Cited

U.S. PATENT DOCUMENTS 6,514,690 B1 * 2/2003 Li ........................ C07K 14/005 435/5
2013/0302790 A1 * 11/2013 Emerson ................. C12N 7/00 435/5

OTHER PUBLICATIONS

Nan et al., "Molecular Biology and Infection of Hepatitis E Virus," Frontiers in Microbiology, 7:1419 (Year: 2016).*
Ding, Q. et al., "Hepatitis E virus ORF3 is a functional ion channel required for release of infectious particles," PNAS, vol. 114; No. 5; 1147-1152 (2017).

(Continued)

*Primary Examiner* — M Franco G Salvoza
(74) *Attorney, Agent, or Firm* — Hamilton, Brook, Smith & Reynolds, P.C.

(57) ABSTRACT

The present invention provides a method of inhibiting hepatitis E virus (HEV) release from a cell that is infected with an HEV, and a method of treating a HEV infection in a subject in need thereof. The present invention also provides a method of identifying agent that inhibits HEV infectivity using a transcomplementation system.

11 Claims, 28 Drawing Sheets

Specification includes a Sequence Listing.

(56) References Cited

OTHER PUBLICATIONS

Kenney, S.P. et al., “Replacement if the hepatitus E virus ORF3 protein PxxP motif with heterologous late domain motifs affects virus release via interaction with TSG101,” Virology, vol. 486; 198-208 (2015).
Kenney, S.P. and Meng, X.-J., “Therapeutic Targets for the Treatment of Hepatitis E Virus Infection,” Expert Opinion Ther Targets, vol. 19; No. 9; 1245-1260 (2015).
Liu, T. et al., “RNA Interference Induces Effective Inhibition of mRNA Accumulation and Protein Expression of SHEV ORF3 Gene In vitro,” Curr. Microbiol., vol. 62; 1355-1362 (2011).
Yamada, K. et al., “ORF3 protein of hepatitis E virus is essential for virion release from infected cells,” Journal of General Virology, vol. 90; 1880-1891 (2009).
Notification of Transmittal of the International Search Report and Written Opinion for International Application No. PCT/US2017/052769, entitled: “Methods and Compositions for Inhibiting Hepatitis E Virus,” dated Mar. 2, 2018.
Notification Concerning Transmittal of International Preliminary Report on Patentability for International Application No. PCT/US2017/052769, entitled: “Methods and Compositions for Inhibiting Hepatitis E Virus,” dated Apr. 4, 2019.
Emerson et al., “In Vitro Replication of Hepatitis E Virus (HEV) Genomes and of an HEV Replicon Expressing Green Fluorescent Protein”, Journal of Virology, May 2004, p. 4838-4846, vol. 78, No. 9.
Shukla et al., “Adaptation of a Genotype 3 Hepatitis E Virus to Efficient Growth in Cell Culture Depends on an Inserted Human Gene Segment Acquired by Recombination”, Journal of Virology, May 2012, p. 5697-5707, vol. 86, No. 10.
Tanaka et al., “Development and Characterization of a Genotype 4 Hepatitis E Virus Cell Culture System Using a HE-JF5/15F Strain Recovered from a Fulminant Hepatitis Patient”, Journal of Clinical Microbiology, Jun. 2009, p. 1906-1910, vol. 47, No. 6.
Yamada et al., “Construction of an infectious cDNA clone of hepatitis E virus strain JE03-1760F that can propagate efficiently in cultured cells”, Journal of General Virology, 2009, 90, p. 457-462.
Notification Concerning Transmittal of International Preliminary Report on Patentability for International Application No. PCT/US2017/052769, titled: “Methods and Compositions for Inhibiting Hepatitis E Virus,” dated Apr. 4, 2019.

* cited by examiner

FIG. 8C

| Name | HEV egress | Protein Expression | Ion Channel activity |
|---|---|---|---|
| WT | 100.0±9.1% | ✓ | 100.0±5.4% |
| 11-13A | 20.7±5.3% | ✓ | 10.4±2.0% |
| 29-31A | 16.3±7.2% | Not stable | |
| 32-34A | 9.3±1.1% | Not stable | |
| 35-37A | 5.6±0.5% | ✓ | 70.5±3.8% |
| 38-40A | 10.4±3.7% | ✓ | 122.4±10.2% |
| 59-61A | 9.6±0.8% | ✓ | 9.4±3.3% |
| 71-73A | 10.8±2.8% | ✓ | 55.2±1.0% |
| 80-82A | 11.1±5.2% | ✓ | 47.3±7.3% |
| 83-85A | 18.7±9.4% | ✓ | 94.0±4.5% |
| 86-88A | 10.2±3.0% | ✓ | 90.6±9.2% |
| 95-97A | 12.3±0.6% | ✓ | 86.3±4.1% |

FIG. 12A

| compound | chemical | target |
|---|---|---|
| amantadine | 1-adamantylamine | IAV M2, HCV p7, DENV M |
| rimantadine | 1-(1-adamantyl)ethanamine | IAV M2, HCV p7 |
| NN-DNJ | N-nonyl-deoxynojirimycin | HCV p7 |
| NN-DGJ | N-nonyl-deoxygalactonojirimycin | HCV p7 |
| HMA | 5-(N,N-hexamethylene)amiloride | HCV p7, SARS CoV E, DENV E, HIV Vpu |
| Emodin | 6-methyl-1,3,8-trihydroxyanthraquinone | SARS CoV 3a |
| Verapamil | (RS)-2-(3,4-Dimethoxyphenyl)-5-{[2-(3,4-dimethoxyphenyl)ethyl]-(methyl)amino}-2-prop-2-ylpentanenitrile | CSFV p7 |

SEQUENCE LISTING

```
<160> NUMBER OF SEQ ID NOS: 12

<210> SEQ ID NO 1
<211> LENGTH: 113
<212> TYPE: PRT
<213> ORGANISM: Hepatitis E Virus

<400> SEQUENCE: 1

Met Gly Ser Pro Cys Ala Leu Gly Leu Phe Cys Cys Cys Ser Ser Cys
1               5                   10                  15

Phe Cys Leu Cys Cys Pro Arg His Arg Pro Ala Ser Arg Leu Ala Val
            20                  25                  30

Val Val Gly Gly Ala Ala Ala Val Pro Ala Val Val Ser Gly Val Thr
        35                  40                  45

Gly Leu Ile Leu Ser Pro Ser Pro Ser Pro Ile Phe Ile Gln Pro Thr
    50                  55                  60

Pro Ser Pro Pro Ile Ser Phe His Asn Pro Gly Leu Glu Leu Ala Leu
65                  70                  75                  80

Gly Ser Arg Pro Ala Pro Leu Ala Pro Leu Gly Val Thr Ser Pro Ser
                85                  90                  95

Ala Pro Pro Leu Pro Pro Ala Val Asp Leu Pro Gln Leu Gly Leu Arg
            100                 105                 110

Arg
```

-continued

<210> SEQ ID NO 2
<211> LENGTH: 114
<212> TYPE: PRT
<213> ORGANISM: Hepatitis E Virus

<400> SEQUENCE: 2

```
Met Gly Ser Arg Pro Cys Ala Leu Gly Leu Phe Cys Cys Cys Ser Ser
1               5                   10                  15

Cys Phe Cys Leu Cys Cys Pro Arg His Arg Pro Val Ser Arg Leu Ala
            20                  25                  30

Ala Val Val Gly Gly Ala Ala Ala Val Pro Ala Val Val Ser Gly Val
        35                  40                  45

Thr Gly Leu Ile Leu Ser Pro Ser Gln Ser Pro Ile Phe Ile Gln Pro
    50                  55                  60

Thr Pro Ser Pro Pro Met Ser Pro Leu Arg Pro Gly Leu Asp Leu Val
65                  70                  75                  80

Phe Ala Asn Pro Pro Asp His Ser Ala Pro Leu Gly Val Thr Arg Pro
                85                  90                  95

Ser Ala Pro Pro Leu Pro His Val Val Asp Leu Pro Gln Leu Gly Pro
            100                 105                 110

Arg Arg
```

<210> SEQ ID NO 3
<211> LENGTH: 114
<212> TYPE: PRT
<213> ORGANISM: Hepatitis E Virus

<400> SEQUENCE: 3

```
Met Gly Ser Pro Pro Cys Ala Leu Gly Leu Phe Cys Cys Cys Ser Ser
1               5                   10                  15

Cys Phe Cys Leu Cys Cys Pro Arg His Arg Pro Val Ser Arg Leu Ala
            20                  25                  30

Ala Val Val Gly Gly Ala Ala Ala Val Pro Ala Val Val Ser Gly Val
        35                  40                  45

Thr Gly Leu Ile Leu Ser Pro Ser Gln Ser Pro Ile Phe Ile Gln Pro
    50                  55                  60

Thr Pro Leu Pro Gln Thr Leu Pro Leu Arg Pro Gly Leu Asp Leu Ala
65                  70                  75                  80

Phe Ala Asn Gln Pro Gly His Leu Ala Pro Leu Gly Glu Ile Arg Pro
                85                  90                  95

Ser Ala Pro Pro Leu Pro Pro Val Ala Asp Leu Pro Gln Pro Gly Leu
            100                 105                 110

Arg Arg
```

<210> SEQ ID NO 4
<211> LENGTH: 114
<212> TYPE: PRT
<213> ORGANISM: Hepatitis E Virus

<400> SEQUENCE: 4

```
Met Glu Met Pro Pro Cys Ala Leu Gly Leu Phe Cys Phe Cys Ser Ser
1               5                   10                  15

Cys Phe Cys Leu Cys Cys Pro Arg His Arg Pro Val Ser Arg Leu Ala
            20                  25                  30

Val Ala Ala Gly Gly Ala Ala Ala Val Pro Ala Val Val Ser Gly Val
        35                  40                  45

Thr Gly Leu Ile Leu Ser Pro Ser Pro Ser Pro Ile Phe Ile Gln Pro
```

```
    50                  55                  60

Ile Pro Ser His Pro Thr Phe Gln Pro Gln Pro Gly Leu Glu Leu Ala
65                  70                  75                  80

Leu Gly Ser Gln Pro Val His Ser Ala Pro Leu Gly Ala Thr Asn Pro
                85                  90                  95

Ser Ala Pro Pro Leu Leu Pro Val Ala Asp Leu Pro Gln Leu Gly Leu
            100                 105                 110

Arg Arg

<210> SEQ ID NO 5
<211> LENGTH: 5082
<212> TYPE: DNA
<213> ORGANISM: Hepatitis E Virus

<400> SEQUENCE: 5
atggaggccc atcagtttat caaggctcct ggcatcacta ctgctattga gcaggctgct     60
ctagcagcgg ccaactctgc ccttgcgaat gctgtggtag ttaggccttt tctctctcac    120
cagcagattg agatccttat taacctaatg caacctcgcc agcttgtttt ccgccccgag    180
gttttctgga accatcccat ccagcgtgtt atccataatg agctggagct ttactgtcgc    240
gcccgctccg gccgctgcct tgaaattggt gcccaccccc gctcaataaa tgacaatcct    300
aatgtggtcc accgttgctt cctccgtcct gccgggcgtg atgttcagcg ttggtatact    360
gcccctaccc gcgggccggc tgctaattgc cggcgttccg cgctgcgcgg gctccccgct    420
gctgaccgca cttactgctt cgacgggttt tctggctgta actttcccgc cgagacgggc    480
atcgccctct attctctcca tgatatgtca ccatctgatg tcgccgaggc tatgttccgc    540
catggtatga cgcggcttta cgctgccctc cacctcccgc ctgaggtcct gttgcccccct    600 ggcacatacc gcaccgcgtc gtacttgctg atccatgacg gcaggcgcgt tgtggtgacg    660
tatgagggtg acactagtgc tggttataac cacgatgttt ccaacctgcg ctcctggatt    720
agaaccacta aggttaccgg agaccaccct ctcgtcatcg agcgggttag ggccattggc    780
tgccactttg tccttttact cacggctgcc ccggagccat cacctatgcc ctatgtccct    840
tacccccggt ctaccgaggt ctatgtccga tcgatcttcg gcccgggtgg taccccctcc    900
ctatttccaa cctcatgctc caccaagtcg accttccatg ctgtccctgc ccatatctgg    960
gaccgtctca tgttgttcgg ggccacccta gatgaccaag ccttttgctg ctcccgccta   1020
atgacttacc tccgcggcat tagctacaag gttactgtgg gcacccttgt tgccaatgaa   1080
ggctggaacg cctctgagga cgctcttaca gctgtcatca ctgccgccta ccttaccatc   1140
tgccaccagc ggtacctccg cactcaggct atatctaagg ggatgcgtcg cctggagcgg   1200
gagcatgctc agaagtttat aacacgcctc tacagttggc tctttgagaa gtccggccgt   1260
gattatatcc ccggccgtca gttggagttc tacgctcagt gtaggcgctg gctctcggcc   1320
ggctttcatc ttgacccacg ggtgttggtt tttgatgagt cggccccctg ccactgtagg   1380
actgcgattc gtaaggcggt ctcaaagttt tgctgcttta tgaagtggct gggccaggag   1440
tgcacctgtt ttctacaacc tgcagaaggc gtcgttggcg accagggcca tgacaacgag   1500
gcctatgagg ggtctgatgt tgaccctgct gaatccgcta ttagtgacat atctgggtcc   1560
tacgtagtcc ctggcactgc cctccaaccg ctttaccaag cccttgacct ccccgctgag   1620
attgtggctc gtgcaggccg gctgaccgcc acagtaaagg tctcccaggt cgacgggcgg   1680
atcgattgtg agacccttct cggtaataaa accttccgca cgtcgtttgt tgacggggcg   1740
```

-continued

```
gttttagaga ctaatggccc agagcgccac aatctctctt ttgatgccag tcagagcact   1800
atggccgccg gccctttcag tctcacctat gccgcctctg ctgctgggct ggaggtgcgc   1860
tatgtcgccg ccgggcttga ccaccgggcg gtttttgccc ccggcgtttc accccggtca   1920
gcccctggcg aggtcaccgc cttctgttct gccctataca ggtttaatcg cgaggcccag   1980
cgcctttcgc tgaccggtaa tttttggttc catcctgagg ggctccttgg cccctttgcc   2040
ccgttttccc ccgggcatgt ttgggagtcg gctaatccat tctgtggcga gagcacactt   2100
tacacccgca cttggtcgga ggttgatgct gttcctagtc cagcccagcc cgacttaggt   2160
tttacatctg agccttctat acctagtagg gccgccacac ctaccccggc ggcccctcta   2220
cccccccctg caccggatcc ttcccctact ctctctgctc cggcgcgtgg tgagccggct   2280
cctggcgcta ccgccggggc cccagccata acccaccaga cggcccggca tcgccgcctg   2340
ctctttacct acccggatgg ctctaaggtg ttcgccggct cgctgtttga gtcgacatgt   2400
acctggctcg ttaacgcgtc taatgttgac caccgccctg gcggtgggct ctgtcatgca   2460
ttttaccaga ggtaccccgc ctcctttgat gctgcctctt ttgtgatgcg cgacggcgcg   2520
gccgcctaca cattaacccc ccggccaata attcatgccg tcgctcctga ttataggttg   2580
gaacataacc caaagaggct tgaggctgcc taccgggaga cttgctcccg cctcggtacc   2640
gctgcatacc cactcctcgg gaccggcata taccaggtgc cgatcggtcc cagttttgac   2700
gcctgggagc ggaatcaccg ccccggggac gagttgtacc ttcctgagct tgctgccaga   2760
tggttcgagg ccaataggcc gacctgccca actctcacta taactgagga tgttgcgcgg   2820
acagcaaatc tggctatcga acttgactca gccacagacg tcggccgggc ctgtgccggc   2880
tgtcgagtca cccccggcgt tgtgcagtac cagtttaccg caggtgtgcc tggatccggc   2940
aagtcccgct ctattaccca agccgacgtg gacgttgtcg tggtcccgac ccgggagttg   3000
cgtaatgcct ggcgccgccg cggcttcgct gctttcaccc cgcacactgc ggctagagtc   3060
acccaggggc gccgggttgt cattgatgag gccccgtccc ttccccctca tttgctgctg   3120
ctccacatgc agcgggccgc caccgtccac cttcttggcg acccgaatca gatcccagcc   3180
atcgattttg agcacgccgg gctcgttccc gccatcaggc ccgatttggc ccccacctcc   3240
tggtggcatg ttacccatcg ctgccctgcg gatgtatgtg agctaatccg cggcgcatac   3300
cctatgattc agaccactag tcgggtcctc cggtcgttgt tctggggtga gcccgccgtt   3360
gggcagaagc tagtgttcac ccaggcggct aaggccgcca accccggttc agtgacggtc   3420
catgaggcac agggcgctac ctacacagag actaccatca ttgccacggc agatgctcga   3480
ggcctcattc agtcgtcccg agctcatgcc attgttgcct tgacgcgcca cactgagaag   3540
tgcgtcatca ttgacgcacc aggcctgctt cgcgaggtgg gcatctccga tgcaatcgtt   3600
aataactttt tccttgctgg tggcgaaatt ggccaccagc gcccatctgt tatccctcgc   3660
ggcaatcctg acgccaatgt tgacaccttg gctgccttcc cgccgtcttg ccagattagc   3720
gccttccatc agttggctga ggagcttggc cacagacctg cccctgtcgc ggctgttcta   3780
ccgccctgcc ctgagcttga acagggcctt ctctacctgc cccaagaact caccacctgt   3840
gatagtgtcg taacatttga attaacagat attgtgcatt gtcgtatggc cgccccgagc   3900
cagcgcaagg ccgtgctgtc cacgctcgtg ggccgttatg gccgccgcac aaagctctac   3960
aatgcctccc actctgatgt tcgcgactct ctcgcccgtt ttatcccggc cattggcccc   4020
gtacaggtta caacctgtga attgtacgag ctagtggagg ccatggtcga gaagggccag   4080
gacggctccg ccgtccttga gctcgacctt tgtagccgcg acgtgtccag gatcaccttc   4140
```

-continued ttccagaaag attgtaataa attcaccacg ggggagacca tcgcccatgg taaagtgggc 4200
cagggcattt cggcctggag taagaccttc tgtgcccttt tcggcccctg gttccgtgct 4260
attgagaagg ctatcctggc cctgctccct cagggtgtgt tttatgggga tgcctttgat 4320
gacaccgtct tctcggcggc tgtggccgca gcaaaggcat ccatggtgtt tgagaatgac 4380
ttttctgagt ttgattccac ccagaataat tttttccttgg gcctagagtg tgctattatg 4440
gaggagtgtg ggatgccgca gtggctcatc cgcttgtacc accttataag gtctgcgtgg 4500
attctgcagg ccccgaagga gtccctgcga gggttttgga agaaacactc cggtgagccc 4560
ggcacccttc tgtggaatac tgtctggaac atggccgtta tcacccactg ttatgatttc 4620
cgcgatctgc aggtggctgc ctttaaaggt gatgattcga tagtgctttg cagtgagtac 4680
cgtcagagcc caggggctgc tgtcctgatt gctggctgtg gcctaaagtt gaaggtggat 4740
ttccgtccga ttggtctgta tgcaggtgtt gtggtggccc ccggccttgg cgcgcttcct 4800
gatgtcgtgc gcttcgccgg tcggcttact gagaagaatt ggggccctgg ccccgagcgg 4860
gcggagcagc tccgcctcgc tgtgagtgat tttctccgca agctcacgaa tgtagctcag 4920
atgtgtgtgg atgttgtctc tcgtgtttat ggggtttccc ctgggctcgt tcataacctg 4980
attggcatgc tacaggctgt tgctgatggc aaggctcatt tcactgagtc agtgaagcca 5040
gtgcttgacc tgacaaattc aattctgtgt cgggtggaat ga 5082

<210> SEQ ID NO 6
<211> LENGTH: 5076
<212> TYPE: DNA
<213> ORGANISM: Hepatitis E Virus

<400> SEQUENCE: 6
atggaggccc accagttcat taaggctcct ggcatcacta ctgctattga gcaagcagct 60
ctagcagcgg ccaactccgc ccttgcgaat gctgtggtgg tccggccttt cctttcccat 120
cagcaggttg agatccttat aaatctcatg caacctcggc agctggtgtt tcgtcctgag 180 gtttttttgga atcacccgat tcaacgtgtt atacataatg agcttgagca gtattgccgt 240
gctcgctcgg gtcgctgcct tgagattgga gcccacccac gctccattaa tgataatcct 300
aatgtcctcc atcgctgctt tctccacccc gtcggccggg atgttcagcg ctggtacaca 360
gccccgacta ggggacctgc ggcgaactgt cgccgctcgg cacttcgtgg tctgccacca 420
gccgaccgca cttactgttt tgatggcttt gccggctgcc gttttgccgc cgagactggt 480
gtggctctct attctctcca tgacttgcag ccggctgatg ttgccgaggc gatggctcgc 540
cacggcatga cccgccttta tgcagctttc cacttgcctc cagaggtgct cctgcctcct 600
ggcacctacc ggacatcatc ctacttgctg atccacgatg gtaagcgcgc ggttgtcact 660
tatgagggtg acactagcgc cggttacaat catgatgttg ccaccctccg cacatggatc 720
aggacaacta aggttgtggg tgaacaccct ttggtgatcg agcgggtgcg gggtattggc 780
tgtcactttg tgttgttgat cactgcggcc cctgagccct ccccgatgcc ctacgttcct 840
tacccgcgtt cgacggaggt ctatgtccgg tctatctttg ggcccggcgg gtccccgtcg 900
ctgttcccga ccgcttgtgc tgtcaagtcc acttttcacg ccgtccccac gcacatctgg 960
gaccgtctca tgctctttgg ggccaccctc gacgaccagg ccttttgctg ctccaggctt 1020
atgacgtacc ttcgtggcat tagctataag gtaactgtgg gtgccctggt cgctaatgaa 1080
ggctggaatg ccaccgagga tgcgctcact gcagttatta cggcggctta cctcacaata 1140

```
tgtcatcagc gttatttgcg gacccaggcg atttctaagg gcatgcgccg gcttgagctt   1200
gaacatgctc agaaatttat ttcacgcctc tacagctggc tatttgagaa gtcaggtcgt   1260
gattacatcc caggccgcca gctgcagttc tacgctcagt gccgccgctg gttatctgcc   1320
gggttccatc tcgacccccg caccttagtt tttgatgagt cagtgccttg tagctgccga   1380
accaccatcc ggcggatcgc tggaaaattt tgctgtttta tgaagtggct cggtcaggag   1440
tgttcttgtt tcctccagcc cgccgagggg ctggcgggcg accaaggtca tgacaatgag   1500
gcctatgaag gctctgatgt tgatactgct gagcctgcca ccctagacat tacaggctca   1560
tacatcgtgg atggtcggtc tctgcaaact gtctatcaag ctctcgacct gccagctgac   1620
ctggtagctc gcgcagcccg actgtctgct acagttactg ttactgaaac ctctggccgt   1680
ctggattgcc aaacaatgat cggcaataag acttttctca ctacctttgt tgatggggca   1740
cgccttgagg ttaacgggcc tgagcagctt aacctctctt ttgacagcca gcagtgtagt   1800
atggcagccg gcccgttttg cctcacctat gctgccgtag atggcgggct ggaagttcat   1860
ttttccaccg ctggcctcga gagccgtgtt gttttccccc ctggtaatgc cccgactgcc   1920
ccgccgagtg aggtcaccgc cttctgctca gctctttata ggcacaaccg gcagagccag   1980
cgccagtcgg ttattggtag tttgtggctg caccctgaag gtttgctcgg cctgttcccg   2040
ccccttttcac ccgggcatga gtggcggtct gctaacccat tttgcggcga gagcacgctc   2100
tacacccgca cttggtccac aattacagac acacccttaa ctgtcgggct aatttccggt   2160
catttggatg ctgctcccca ctcggggggg ccacctgcta ctgccacagg ccctgctgta   2220
ggctcgtctg actctccaga ccctgacccg ctacctgatg ttacagatgg ctcacgcccc   2280
tctggggccc gtccggctgg ccccaacccg aatggcgttc cgcagcgccg cttactacac   2340
acctaccctg acggcgctaa gatctatgtc ggctccattt tcgagtctga gtgcacctgg   2400
cttgtcaacg catctaacgc cggccaccgc cctggtggcg ggctttgtca tgcttttttt   2460
cagcgttacc ctgattcgtt tgacgccacc aagtttgtga tgcgtgatgg tcttgccgcg   2520
tataccctta caccccggcc gatcattcat gcggtggccc cggactatcg attggaacat   2580
aaccccaaga ggctcgaggc tgcctaccgc gagacttgcg cccgccgagg cactgctgcc   2640
tatccactct taggcgctgg catttaccag gtgcctgtta gtttgagttt tgatgcctgg   2700
gagcggaacc accgcccgtt tgacgagctt tacctaacag agctggcggc tcggtggttt   2760
gaatccaacc gccccggtca gcccacgttg aacataactg aggataccgc ccgtgcggcc   2820
aacctggccc tggagcttga ctccgggagt gaagtaggcc gcgcatgtgc cgggtgtaaa   2880
gtcgagcctg gcgttgtgcg gtatcagttt acagccggtg tccccggctc tggcaagtca   2940
aagtccgtgc aacaggcgga tgtggatgtt gttgttgtgc ccactcgcga gcttcggaac   3000
gcttggcggc gccggggctt tgcggcattc actccgcaca ctgcggcccg tgtcactagc   3060
ggccgtaggg ttgtcattga tgaggcccct tcgctccccc cacacttgct gcttttacat   3120
atgcagcgtg ctgcatctgt gcacctcctt ggggacccga atcagatccc cgccatagat   3180
tttgagcaca ccggtctgat tccagcaata cggccggagt tggtcccgac ttcatggtgg   3240
catgtcaccc accgttgccc tgcagatgtc tgtgagttag tccgtggtgc ttaccctaaa   3300
atccagacta caagtaaggt gctccgttcc cttttctggg gagagccagc tgtcggccag   3360
aagctagtgt tcacacaggc tgctaaggcc gcgcaccccg gatctataac ggtccatgag   3420
gcccagggtg ccacttttac cactacaact ataattgcaa ctgcagatgc ccgtggcctc   3480
atacagtcct cccgggctca cgctatagtt gctctcacta ggcatactga aaaatgtgtt   3540
```

```
atacttgact ctcccggcct gttgcgtgag gtgggtatct cagatgccat tgttaataat   3600
ttcttccttt cgggtggcga ggttggtcac cagagaccat cggtcattcc gcgaggcaac   3660
cctgaccgca atgttgacgt gcttgcggcg tttccacctt catgccaaat aagcgccttc   3720
catcagcttg ctgaggagct gggccaccgg ccggcgccgg tggcggctgt gctacctccc   3780
tgccctgagc ttgagcaggg ccttctctat ctgccacagg agctagcctc ctgtgacagt   3840
gttgtgacat ttgagctaac tgacattgtg cactgccgca tggcggcccc tagccaaagg   3900
aaagctgttt tgtccacgct ggtaggccgg tatggcagac gcacaaggct ttatgatgcg   3960
ggtcacaccg atgtccgcgc ctcccttgcg cgctttattc ccactctcgg gcgggttact   4020
gccaccacct gtgaactctt tgagcttgta gaggcgatgg tggagaaggg ccaagacggt   4080
tcagccgtcc tcgagttgga tttgtgcagc cgagatgtct cccgcataac ctttttccag   4140
aaggattgta acaagttcac gaccggcgag acaattgcgc atggcaaagt cggtcagggt   4200
atcttccgct ggagtaagac gttttgtgcc ctgtttggcc cctggttccg tgcgattgag   4260
aaggctattc tatccctttt accacaagct gtgttctacg gggatgctta tgacgactca   4320
gtattctctg ctgccgtggc tggcgccagc catgccatgg tgtttgaaaa tgatttttct   4380
gagtttgact cgactcagaa taacttttcc ctaggtcttg agtgcgccat tatggaagag   4440
tgtggtatgc cccagtggct tgtcaggttg taccatgccg tccggtcggc gtggatcctg   4500
caggccccaa aagagtcttt gagagggttc tggaagaagc attctggtga gccgggcagc   4560
ttgctctgga atacggtgtg gaacatggca atcattgccc attgctatga gttccgggac   4620
ctccaggttg ccgccttcaa gggcgacgac tcggtcgtcc tctgtagtga ataccgccag   4680
agcccaggcg ccggttcgct tatagcaggc tgtggtttga agttgaaggc tgacttccgg   4740
ccgattgggc tgtatgccgg ggttgtcgtc gccccggggc tcggggccct acccgatgtc   4800
gttcgattcg ccggacggct ttcggagaag aactgggggc ctgatccgga gcgggcagag   4860
cagctccgcc tcgccgtgca ggatttcctc cgtaggttaa cgaatgtggc ccagatttgt   4920
gttgaggtgg tgtctagagt ttacggggtt tccccgggtc tggttcataa cctgataggc   4980
atgctccaga ctattggtga tggtaaggcg cattttacag agtctgttaa gcctatactt   5040
gaccttacac actcaattat gcaccggtct gaatga                             5076
```

<210> SEQ ID NO 7
<211> LENGTH: 5298
<212> TYPE: DNA
<213> ORGANISM: Hepatitis E Virus

<400> SEQUENCE: 7

```
atggaggccc accagttcat taaggctcct ggcattacta ctgccattga gcaggctgct     60
ctggctgcgg ccaattccgc cttggcgaat gctgtggtgg ttcggccgtt tttatcccgt    120
ctacaaactg agattcttat caatttgatg caaccccggc agttggtttt ccgccctgaa    180
gtgctttgga atcatcctat ccagcgggtc atacacaatg aactagaaca gtactgccgg    240
gcccgtgctg gccgctgttt ggaggtcgga gcccatccga gatctattaa tgataacccc    300
aacgtcttgc accggtgctt ccttagaccg gttggcaggg atgttcagcg ctggtactct    360
gcccccaccc gtggccctgc ggccaattgc cgccgctccg cgctgcgtgg ccttcccccc    420
gttgaccgca cctactgttt tgatggattc tcccgctgtg cttttgctgc agagaccggt    480
gtggcccttt actctttgca tgacctttgg ccagctgatg ttgcagaggc gatggcccgt    540
```

-continued

```
catgggatga cacggttgta tgccgcacta catcttcctc ctgaggtgct gctaccaccc    600
ggcacctatc acacaacttc gtatctcctg attcacgacg gcgatcgcgc cgttgtaacc    660
tatgagggcg ataccagtgc gggctataac catgatgttt ccatacttcg tgcgtggatc    720
cgtactacta aaatagttgg tgaccacccg ttggttatag agcgtgtgcg ggccattggt    780
tgtcatttcg tgctgttgct caccgcggcc cctgagccgt cacctatgcc ttatgtcccc    840
taccctcgtt caacggaggt gtatgttcgg tctatatttg gccctggcgg ctctccatct    900
ttgtttccgt cagcctgctc tactaaatct accttccacg ctgtcccggt ccatatctgg    960
gatcggctca tgctctttgg tgccaccctg gatgatcagg cgttctgttg ttcacgactc   1020
atgacttacc tccgtggtat tagctacaag gtcactgttg gtgcgcttgt tgctaatgag   1080
gggtggaacg cctctgaaga tgctcttact gcagtgatca ctgcggctta tctgactatc   1140
tgccatcagc gctacctccg tacccaggcg atatccaagg gcatgcgccg gttggaggtt   1200
gagcatgccc agaaatttat cacaagactc tacagttggc tatttgagaa gtctggccgt   1260
gattacatcc ccggccgcca gctccagttt tatgcacagt gccgacggtg gctatctgca   1320
ggattccatc tggaccccag ggtgcttgtt tttgatgaat cagtgccatg tcgttgtagg   1380
acgttcctga agaaagtcgc gggtaaattc tgctgtttta tgcggtggtt agggcaggag   1440
tgcacctgct tcctggagcc agccgagggt ttagttggcg accatggcca tgacaatgag   1500
gcttatgaag gttctgaggt cgaccaggct gaacctgccc atcttgatgt ttcggggact   1560
tatgccgtcc acgggcacca gcttgtagcc ctctataggg cacttaatgt cccacatgat   1620
attgccgctc gagcttcccg attaacggct actgttgagc ttgttgcagg tccagaccgc   1680
ttggagtgcc gcactgtgct cggtaataag accttccgga cgacggtggt tgatggcgcc   1740
catcttgaag cgaatggccc agagcagtat gtcctgtcat ttgacgcctc ctgtcagtct   1800
atgggggccg ggtcgcacaa cctcacttat gagctcaccc ctgccggttt gcaggttagg   1860
atctcatcta acggtctgga ttgcactgct acattccccc ccggcggtgc ccctagcgcc   1920
gcgccagggg aggtggcagc cttctgtgct gccctttaca gatataacag gttcacccag   1980
cggcactcgc tgaccggtgg actatggtta caccctgagg gattgctggg tatcttccct   2040
ccattctccc ctgggcatat ctgggagtct gctaacccct tttgcgggga ggggactttg   2100
tatacccgga cctggtcaac atctggcttt tctagtgatt tctctccccc tgaggcggcc   2160
gcccctgctt cggctgctgc cccggggctg ccccacccta ccccgcctgc tagtgatatt   2220
tgggcgttac caccgccctc cgaggagtgc tacacgcgcc tggggcaacga cttccacacg  2280
aacaagcgcg tgtgcgagga gatcgccatt atccctagca aaaagccccg caacaagatg   2340
gcaggttatg tcacgcatct gatgaagcga attcagagag gcccagtaag aggtatctcc   2400
atcaagctgc aggaggaggc tcaggtcgat gcagcatctg tgccccttac cctcgtgcct   2460
gctgggtcgc ccagccctgt tgtgtcacct tccccaccac cacctccacc cgtgcgtaag   2520
ccatcaacac ccccgccttc tcgtacccgt cgcctcctct acacctaccc cgacggcgct   2580
aaggtgtatg cagggtcatt gtttgaatca gactgtgatt ggctggttaa cgcctcaaac   2640
ccgggccatc gccctggagg tggcctctgt cacgcctttc atcaacgttt tccggaggcg   2700
ttttatccga ctgaattcat tatgcgtgag ggcctagcgg catacaccct gaccccgcgc   2760
cctatcatcc acgcagtggc gcccgactac agggttgagc agaacccgaa gaggctcgag   2820
gcagcgtacc gggaaacttg ctcccgtcgt ggcaccgctg cttacccgct tttaggctcg   2880
ggcatatacc aggtccctgt cagcctcagt tttgatgcct gggaacgcaa tcatcgcccc   2940
```

```
ggcgatgagc tttacttgac tgagcccgct gcggcttggt ttgaggctaa taagccggcg   3000
cagccggcgc ttaccataac tgaggatacg gctcgtacgg ccagcctggc attagagatc   3060
gacgccgcta cagaggttgg ccgtgcttgt gccggctgca ctatcagtcc tgggattgtg   3120
cactatcagt ttaccgctgg ggtcccgggc tcgggcaagt caaggtccat acaacaggga   3180
gatgttgatg tggtggttgt gcccacccgg gagctccgta acagttggcg ccgccggggt   3240
ttcgcggctt tcacacctca cacagcggcc cgtgttacta acggccgccg cgttgtgatt   3300
gatgaggccc catctctccc gccacacctg ttgctgctac atatgcagcg ggcctcctcg   3360
gttcacctac tcggtgaccc aaatcagatc cctgctatcg attttgaaca cgccggcctg   3420
gtccccgcga tccgccccga gcttgcacca acgagctggt ggcacgtcac acaccgttgc   3480
ccggccgatg tgtgcgaact catacgcggg gcctacccca aaatccagac cacgagccgt   3540
gtgctacggt ccctgttttg gaatgaaccg gctatcggcc agaagttggt ttttacgcag   3600
gctgccaagg ccgctaaccc tggtgcgatt acggttcacg aagctcaggg tgccaccttc   3660
actgagacca cagttatagc cacggccgac gccaggggcc tcattcagtc atcccgggcc   3720
catgctatag ttgcacttac ccgccacacc gagaagtgcg tcattttgga tgctcccggc   3780
ctgctgcgtg aagtcggtat ctcggatgtg attgtcaata attttttcct tgcaggcgga   3840
gaggtcggcc atcaccgccc ttctgtgata ccccgcggta accccgatca gaacctcggg   3900
actttacaag ccttcccgcc gtcctgccag attagtgctt accaccagct ggctgaggaa   3960
ttaggccatc gccctgcccc tgttgccgcc gtcttgcccc cttgccccga gcttgagcag   4020
ggcctgcttt acatgccaca agagcttacc gtgtctgata gtgtgctggt ttttgagctc   4080
acggacatag tccactgccg catggccgct ccaagccagc gaaaggctgt tctttcaaca   4140
cttgtggggc ggtatggccg taggacgaag ttatatgagg cagcacattc agatgtccgt   4200
gagtccctag ccaggttcat ccccactatc gggcccgttc aggccaccac atgtgagttg   4260
tatgagttgg ttgaggccat ggtggagaag ggtcaggacg ggtcagccgt cttagagcta   4320
gatctctgca atcgtgatgt ctcgcgcatc acatttttcc aaaaggattg caacaagttt   4380
acaactggtg agactattgc ccatggcaag gttggtcagg gtatatcggc ctggagcaag   4440
acattctgcg ctttgtttgg cccgtggttc cgtgccattg agaaagaaat actggccctg   4500
ctcccgccta atgtctttta tggcgatgct tatgaggagt cagtgcttgc tgccgctgtg   4560
tcaggggcgg ggtcatgcat ggtatttgaa aatgactttt cggagtttga tagcacccag   4620
aacaacttct ctctcggcct tgagtgtgtg gttatggagg agtgcggcat gcctcaatgg   4680
ttaattaggt tgtatcacct ggtacggtca gcctggattc tgcaggcgcc aaaggagtct   4740
cttaagggtt tctggaagaa gcattctggt gagcccggta cccttctttg gaacaccgtt   4800
tggaacatgg caatcatagc acattgctac gagttccgtg actttcgtgt tgctgccttt   4860
aagggtgatg attcggtggt cctctgtagc gactaccggc agagccgcaa tgcggcagct   4920
ttgattgctg gctgtgggct taaattgaag gttgactatc gccccattgg gctgtatgct   4980
ggggtggtgg tggcccctgg cttggggaca ctgcctgatg tggtgcgttt tgctggtcgg   5040
ctgtccgaaa agaattgggg ccccggcccg gaacgtgctg agcagctacg tcttgctgtt   5100
tgtgatttcc ttcgagggtt gacgaacgtt gcgcaggtct gtgttgatgt tgtgtcccgt   5160
gtctatggag ttagccccgg gctggtacat aaccttattg gcatgttgca gaccattgcc   5220
gatggcaagg cccactttac agagactatt aaacctgttc ttgatcttac aaattccatc   5280
```

-continued atacagcggg tagaatga 5298

<210> SEQ ID NO 8
<211> LENGTH: 5109
<212> TYPE: DNA
<213> ORGANISM: Hepatitis E Virus

<400> SEQUENCE: 8
atggaggccc atcagttcat aaaggctcct ggcgtcacta ctgctatcga gcaggcagct 60
ctagcagcgg ccaactccgc cctggcgaat gctgtggtgg ttcggccttt cctttcccgg 120
ctacagacag agattttgat aaacctgatg cagccccggc agcttgtctt ccgacctgag 180
gttctgtgga atcacccaat ccagcgcgta atccacaacg agcttgagca gtactgtcga 240
gcccgtgccg gtcgctgcct tgaggtggga gcccatccgc gctccattaa tgataacccc 300
aatgttttgc accgttgctt tttgaaaccc cgtggtcgcg acgttcagcg gtggtacacc 360
gcccccaccc gcggccctgc agcgaattgc cgccgttcgg ctcttcgtgg acttccacct 420
gttgaccgga catactgttt tgatggtttt tctggatgta cgtttgctgc tgagactggg 480
gttgcccttt attcactgca cgatctgtgg cctgctgacg tcgcagaggc aatggcccgc 540
cacggtatga ctcggctgta tgcagccctt catctccccc cggaggtgtt acttcctcct 600
ggcacctatc ataccacatc atacctttta attcatgacg gcgatcgtgc tgtgattaca 660
tatgagggtg actcgagcgc agggtacaat catgatgtgt ctattctgcg cgcctggatc 720
cgcaccacta aagttaccgg cgaccacccg ttggtcattg agcgagtccg ggcggtaggg 780
tgtcactttg tgcttttgct cacagccgcg cctgaaccat cgccgatgcc ttatgtccca 840
taccctcgct ccactgaggt ctatgtccgg tccatttttg ggccaggcgg ctcgccctct 900
ctcttcccat ctgcctgctc gactaagtct acatttcatg ccgttcctgt gcatatctgg 960
gacaggctca tgctttttgg tgcgaccctt gatgaccagg ctttttgctg ctcgaggctt 1020
atgacgtacc ttcgtggtat tagttataag gttacagtcg gtgctcttgt tgctaacgaa 1080
ggctggaacg cctccgagga tgcactgact gctgtaatta ctgcagcata tctcaccatt 1140
tgtcatcaga ggtacctccg cacgcaggcc atttcgaaag gaatgaagag gttggagctt 1200
gaacatgcgc agaaatttat aacgcgcctt tatagttggc tgttcgagaa gtccggccgt 1260
gattacatcc ccggccgtca gttgcagttt tatgcccagt gccgccggtg gttatctgca 1320
ggctttcatc ttgacccacg tgtacttgtt tttgatgagg cagccccctg ccgttgtcgt 1380
aatttccttc ggaaagccgc ccacaagttt tgttgcttca tgcggtggtt aggtcaggat 1440
tgcacctgtt tcctccaacc tatcgaggga cgggttggcg agcagggtta tgataatgaa 1500
gcatttgaag ggtcggacgt cgaccctgct gaggaggcaa ctgtgagtat ctctgggtca 1560
tatattgtaa ctggtagcca gctacagcct ctatatcagg cgcttggtat cccctctgat 1620
cttgctgccc gtgccggccg gctcactgcc actgttgaag tttctgatgc aaatggccgc 1680
cttacctgca aaaccatcat gggcaataaa actttctcaa cagtcttcac tgatggcgcc 1740
cagctggagg ccaacgggcc ggagcagtat gtgctgtcat tcgacccgat taaacaaact 1800
atggccgccg gcccgcataa tcttagttat accttgacat ctgcaggcct tgaaatacat 1860
gtcgtctccg ccgggcttga ttgtaaggcc gtctttccgt ccggggttgc gaccccgtct 1920
gcccccgggg aggtgtctgc cttctgttca gcattgtaca gatttaaccg ctgtgtccag 1980
cggcactccc tcattggggg tgtgtggtac caccctgagg ggctagtcgg cctgttcccg 2040
ccgttttccc ccggccatag ctgggagtct gctaacccct tttgcgggga gagtaccctt 2100

```
tatacccgta cctggtcggt atcgggattt tccagctgtt tttccccact tgaaccgggg   2160
gccccggacc cgccccctct tgttgagact gacacgccta cagttgttga tactctgcct   2220
ccagttgttt cagtacccct tgagcaaata gtacttccac cagactctgt agataaggca   2280
gccggcccga ccgcatctag cgcccctgtt gtaccgccag caccagtgca gtctgtagtt   2340
caaccatctg ggcctcgccg gcggctgctt catacttatc ctgatggctc gaaggtgtat   2400
gctggctccc tttttgagtc cgactgtact tggctggtta acgcatctaa ccctggccac   2460
cgccctggtg gcggcctctg ccatgcgttt taccaacggt tcccagagtc atttgatccc   2520
gctgagtttg ttatgtcaga tgggtttgca gcctacaccc tgtctccccg gcccattatt   2580
catgctgttg ctcctgacta tcgggttgaa cataacccta agaggcttga ggccgcctat   2640
cgggagacgt gctctcgtct cgggactgca gcttaccctt tacttggcgc cggtatatat   2700
aaggtgcctg ttgggctgag cttcgatgcc tgggaacgta accaccggcc cggggatgag   2760
ctgtatctga ctgagccagc cgtagcttgg tttgaggcaa accggcctac tctcccagct   2820
cttaccatca ctgaggatac cgcgcgtacg gcgaacctgg cattggagct agactccgcc   2880
actgaagtcg gccgggcgtg tgctggctgc cgtgtagagc ccggtgtcgt ccattatcag   2940
tttacagcag gtgtccccgg atcaggtaaa tcccggtcag tccagcaggg ggaggtggat   3000
gtggtagtgg taccaactcg tgagctgcgc aattcgtggc ggcgccgcgg gttcgcagct   3060
tatacacccc acaccgcagc tcgtgtcacc cgtggtcgta gggttgttat tgatgaggcc   3120
ccgtcgctcc ctccacactt gcttttgctg catatgcagc gggcctcctc agtccatctc   3180
ttaggtgatc ctaatcaaat ccctgccatt gactttgagc acgccggcct tgttccagct   3240
attcgaccgg agttggtccc gacaaaatgg tggcacgtta ctcatagatg cccagccgat   3300
gtctgtgagt taattcgtgg tgcgtaccca aagatccaga ctgtgagccg cgtactccgc   3360
tctctgttct ggggggagcc ccccgtgggt cagaagctgg tgttcaccca ggcggcgaag   3420
gccgccaacc ctggtgcgat tacagtccac gaggcccagg gtgccacatt cactgagact   3480
acaattatcg ccacggcgga cgcccgtggg ctgattcagt cctccagggc ccatgcgatt   3540
gtggctctga cccgccacac agagaaatgt gtggtcgttg acgccccggg cctcctccgc   3600
gaggttggta tctctgacgc tattgttaat aatttcttcc tttccggcgg tcaggttggt   3660
cagcaccgcc cgtcagtcat accacgcggc actattgatt gtaatgttga tacacttgat   3720
gcattcccgc cctcctgtca gtttagtgcc taccaccagc ttgccgagga gcttggccat   3780
cgaccggccc cgattgctgc tgtcttacct ccctgcccgg agcttgaaca gggcctgctt   3840
tatatgcctc aggagctcac tacatcggac agtgtgctaa catttgagct tacagatata   3900
gtgcactgcc gtatggcggc gcctagtcag cgcaaggcag tcctgtcgac tcttgtcggt   3960
aggtatggcc gccgtacgaa gctgtatgaa gctgctcatg cagatgttcg tgggtctctg   4020
aatcatttta tccccgagct ccgccctatc agcgtcacta cctgcgagct ctatgagctt   4080
gtagaggcca tggttgagaa aggccaggac ggctccgcgg ttctggagct cgacttgtgc   4140
agccgtgatg tctcgcgaat aacatttttc cagaaagact gcaataagtt tacaactggc   4200
gaaacaatag cgcatggcaa agttgggcag gggatatctg catggagtaa aacctttttgc   4260
gccctgtttg gcccctggtt ccgtgctatt gagaaagaga ttctagctgt gcttgcgcct   4320
aacgtatttt atggtgatgc atatgaggac acagttttgg ccgctgccgt cgcaggagcc   4380
tccggctgta aggtttttga gaatgatttt tcagagtttg atagtaccca aaataatttc   4440
```

tcgcttgggc tggagtgtat aattatggag gagtgtggca tgccgcagtg gatgattcgc 4500
ctctaccatc tcgtccgctc cgcctgggtc ctccaggccc cgaaggagtc cttgcggggt 4560
ttttggaaga aacactctgg tgaacccggt actctgctct ggaacactgt ctggaatatg 4620
gcagttatag cccactgtta tgagttccgt gacctaaaag ttgcggcgtt taagggggat 4680
gattctgttg tgctctgtag cgactatcgg cagagccgtg atgcagctgc cttgattgcg 4740
ggctgtgggt tgaagcttaa ggtggacttt aggcctattg ggctgtatgc tggtgttgtt 4800
gtggccccag gtttaggaac cctacctgat gttgttaggt ttgctgggcg actctcagag 4860
aaaaactggg ggcccggttt ggagagggca gagcagctac ggctggctgt ttgtgacttt 4920
ctgcgaaggt taacgaatgt ggctcaggtt tgtgtggatg ttgtctcgca agtatatggt 4980
gttagccctg gcttggtaca taacctgatt gggatgctcc agactattgc tgatggtaag 5040
gcccatttta ccgaaacagt taaacctgtc cttgatttga ccaactccat catatatcgg 5100
gtggattga 5109

<210> SEQ ID NO 9
<211> LENGTH: 1983
<212> TYPE: DNA
<213> ORGANISM: Hepatitis E Virus

<400> SEQUENCE: 9
atgcgccctc ggcctatttt gctgttgctc ctcatgtttc tgcctatgct gcccgcgcca 60
ccgcccggtc agccgtctgg ccgccgtcgt gggcggcgca gcggcggttc cggcggtggt 120
ttctggggtg accgggttga ttctcagccc ttcgcaatcc cctatattca tccaaccaac 180
cccttcgccc ccgatgtcac cgctgcggcc ggggctggac ctcgtgttcg ccaacccgcc 240
cgaccactcg gctccgcttg gcgtgaccag gcccagcgcc ccgccgctgc ctcacgtcgt 300
agacctacca cagctggggc cgcgccgcta accgcggtcg ctccggccca tgacaccccg 360
ccagtgcctg atgttgactc ccgcggcgcc atcctgcgcc ggcagtataa cctatcaaca 420
tctcccctca cctcttccgt ggccaccggc acaaatttgg ttctttacgc cgctcctctt 480
agcccgcttc taccctcca ggacggcacc aatactcata taatggctac agaagcttct 540
aattatgccc agtaccgggt tgctcgtgcc acaattcgct accgcccgct ggtccccaac 600
gctgttggtg gctacgctat ctccatttcg ttctggccac agaccaccac caccccgacg 660
tccgttgaca tgaattcaat aacctcgacg gatgtccgta ttttagtcca gcccggcata 720
gcctccgagc ttgttattcc aagtgagcgc ctacactatc gcaaccaagg ttggcgctct 780
gttgagacct ccggggtggc ggaggaggag gccacctctg gtcttgtcat gctctgcata 840
catggctcac ctgtaaattc ttatactaat acaccctata ccggtgccct cgggctgttg 900
gactttgccc tcgaacttga gttccgcaac ctcacccccg gtaataccaa tacgcgggtc 960
tcgcgttact ccagcactgc ccgtcaccgc cttcgtcgcg gtgcagatgg gactgccgag 1020
ctcaccacca cggctgctac tcgcttcatg aaggacctct attttactag tactaatggt 1080
gttggtgaga tcggccgcgg gatagcgctt accctgttta accttgctga caccctgctt 1140
ggcggtctac cgacagaatt gatttcgtcg gctggtggcc agctgttcta ctctcgcccc 1200
gtcgtctcag ccaatggcga gccgactgtt aagctgtata catctgtgga gaatgctcag 1260
caggataagg gtattgcaat cccgcatgac atcgacctcg gggaatcccg tgtagttatt 1320
caggattatg acaaccaaca tgagcaggac cgaccgacac cttccccagc cccatcgcgt 1380 ccttttttctg tcctccgagc taatgatgtg ctttggcttt ctctcaccgc tgccgagtat 1440

-continued

```
gaccagtcca cttacggctc ttcgaccggc ccagtctatg tctctgactc tgtgaccttg   1500

gttaatgttg cgaccggcgc gcaggccgtt gcccggtcac tcgactggac caaggtcaca   1560

cttgatggtc gcccccttc caccatccag cagtattcaa agaccttctt tgtcctgccg   1620

ctccgcggta agctctcctt ttgggaggca ggaactacta aagccgggta cccttataat   1680

tataacacca ctgctagtga ccaactgctc gttgagaatg ccgctgggca tcgggttgct   1740

atttccacct acactactag cctgggtgct ggccccgtct ctatttccgc ggttgctgtt   1800

ttagcccccc actctgtgct agcattgctt gaggatacca tggactaccc tgcccgcgcc   1860

catactttcg atgacttctg cccggagtgc cgcccccttg gcctccaggg ctgtgctttt   1920

cagtctactg tcgctgagct tcagcgcctt aagatgaagg tgggtaaaac tcgggagtta   1980

tag                                                                1983
```

<210> SEQ ID NO 10
<211> LENGTH: 1980
<212> TYPE: DNA
<213> ORGANISM: Hepatitis E Virus

<400> SEQUENCE: 10

```
atgcgcccta ggcctctttt gctgttgttc ctcttgtttc tgcctatgtt gcccgcgcca     60

ccgaccggtc agccgtctgg ccgccgtcgt gggcggcgca gcggcggtac cggcggtggt    120

ttctggggtg accgggttga ttctcagccc ttcgcaatcc cctatattca tccaaccaac    180

ccctttgccc cagacgttgc cgctgcgtcc gggtctggac ctcgccttcg ccaaccagcc    240

cggccacttg gctccacttg gcgagatcag gcccagcgcc cctccgctgc ctcccgtcgc    300

cgacctgcca cagccggggc tgcggcgctg acggctgtgg cgcctgccca tgacacctca    360

cccgtcccgg acgttgattc tcgcggtgca attctacgcc gccagtataa tttgtctact    420

tcacccctga catcctctgt ggcctctggc actaatttag tcctgtatgc agcccccctt    480

aatccgcctc tgccgctgca ggacggtact aatactcaca ttatggccac agaggcctcc    540

aattatgcac agtaccgggt tgcccgcgct actatccgtt accggcccct agtgcctaat    600

gcagttggag gctatgctat atccatttct ttctggcctc aaacaaccac aacccctaca    660

tctgttgaca tgaattccat tacttccact gatgtcagga ttcttgttca acctggcata    720

gcatctgaat tggtcatccc aagcgagcgc cttcactacc gcaatcaagg ttggcgctcg    780

gttgagacat ctggtgttgc tgaggaggaa gccacctccg gtcttgtcat gttatgcata    840

catggctctc cagttaactc ctataccaat accccttata ccggtgccct tggcttactg    900

gactttgcct tagagcttga gtttcgcaat ctcaccacct gtaacaccaa tacacgtgtg    960

tcccgttact ccagcactgc tcgtcactcc gcccgagggg ccgacgggac tgcggagctg   1020

accacaactg cagccaccag gttcatgaaa gatctccact ttaccggcct taatggggta   1080

ggtgaagtcg gccgcgggat agctctaaca ttacttaacc ttgctgacac gctcctcggc   1140

gggctcccga cagaattaat ttcgtcggct ggcgggcaac tgttttattc ccgcccggtt   1200

gtctcagcca atggcgagcc aaccgtgaag ctctatacat cagtggagaa tgctcagcag   1260

gataagggtg ttgctatccc ccacgatatc gatcttggtg attcgcgtgt ggtcattcag   1320

gattatgaca accagcatga gcaggatcgg cccaccccgt cgcctgcgcc atctcggcct   1380

ttttctgttc tccgagcaaa tgatgtactt tggctgtccc tcactgcagc cgagtatgac   1440

cagtccactt acgggtcgtc aactggcccg gtttatatct cggacagcgt gactttggtg   1500
```

-continued

```
aatgttgcga ctggcgcgca ggccgtagcc cgatcgcttg actggtccaa agtcaccctc   1560

gacgggcggc ccctcccgac tgttgagcaa tattccaaga cattctttgt gctccccctt   1620

cgtggcaagc tctcctttg ggaggccggc acaacaaaag caggttatcc ttataattat   1680

aatactactg ctagtgacca gattctgatt gaaaatgctg ccggccatcg ggtcgccatt   1740

tcaacctata ccaccaggct tggggccggt ccggtcgcca tttctgcggc cgcggttttg   1800

gctccacgct ccgccctggc tctgctggag gatacttttg attatccggg gcgggcgcac   1860

acatttgatg acttctgccc tgaatgccgc gctttaggcc tccagggttg tgctttccag   1920

tcaactgtcg ctgagctcca gcgccttaaa gttaaggtgg gtaaaactcg ggagttgtag   1980
```

<210> SEQ ID NO 11
<211> LENGTH: 1983
<212> TYPE: DNA
<213> ORGANISM: Hepatitis E Virus

<400> SEQUENCE: 11

```
atgtgcccta gggttgttct gctgctgttc ttcgtgtttc tgcctatgct gcccgcgcca     60

ccggccggcc agccgtctgg ccgtcgtcgt gggcggcgca gcggcggtgc cggcggtggt    120

ttctggggtg acagggttga ttctcagccc ttcgccctcc cctatattca tccaaccaac    180

cccttcgccg ccgatatcgt ttcacaatcc ggggctggaa ctcgccctcg gcagccgccc    240

cgcccccttg gctccgcttg gcgtgaccag tcccagcgcc cctccgctgc cccccgccgt    300

cgatctgccc cagctggggc tgcgccgttg actgctgtat caccagcccc tgacacagcc    360

cctgtacctg atgttgattc acgtggtgct attctgcgtc ggcagtataa tttgtccacg    420

tccccgctca cgtcatctgt tgcttcgggt accaatttgg ttctctacgc tgccccgcta    480

aatcccctct tgcccctcca ggatggcacc aacacccata tcatggctac tgaggcatcc    540

aactatgctc agtaccgggt cgttcgagct acgatccgct accgcccgct ggtgccgaat    600

gctgttggtg gttatgctat ttctatttct ttttggcctc aaactacaac taccoctact    660

tctgttgata tgaattctat tacttccact gatgttagga ttttggtcca gcccggtatt    720

gcctccgagt tagtcatccc tagtgagcgc cttcattatc gcaatcaagg ctggcgctct    780

gttgagacca caggtgtggc tgaggaggag gctacctccg gtctggtaat gctttgcatt    840

catggctctc ctgttaactc ttatactaat acaccttaca ctggtgcgtt ggggctcctt    900

gattttgcac tagagcttga attcaggaat ttgacacccg ggaacaccaa cacccgtgtt    960

tcccggtata ccagcacagc ccgtcatcgg ttgcgtcgcg gtgctgatgg gaccgctgag   1020

cttactacca cagcagccac acgatttatg aaggatctgc atttcactgg cactaatggc   1080

gttggtgagg tgggtcgcgg tatcgccctg acactgttca atcttgctga tacgcttcta   1140

ggtggtttac cgacagaatt gatttcgtcg gctgggggtc agttgttcta ctcccgccct   1200

gttgtctcgg ccaatggcga gccgacagtg aagttataca catctgtgga gaatgcgcag   1260

caagacaagg gcattaccat cccacacgat atagatttgg gtgactcccg tgtggttatt   1320

caggattatg ataatcagca cgagcaagac cgacccacgc cgtcacctgc cccctcacgc   1380

cctttctcag tccttcgcgc taacgatgtt ttgtggctct ccctcactgc cgctgagtac   1440

gatcaggcta cgtatgggtc gtctaccaac cctatgtatg tctctgatac agttaccttt   1500

gtcaatgtgg ccactggtgc tcaggctgtt gcccgctctc ttgattggtc taaagttact   1560

ttggatggtc gcccccttac taccattcag cagtattcta agacatttta tgttctcccg   1620

ctccgcggga agctgtcctt ttgggaggct ggcacaacta gggccggcta cccatataac   1680
```

tataacacca ctgctagtga tcaaattctg attgagaatg cggccggcca tcgtgtcgct 1740
atctccacct acactaccag cctgggtgcc ggccctgcct cgatctccgc ggtgggtgta 1800
ttagccccac actcggccct tgctgttctt gaggacactg ttgattaccc tgctcgtgct 1860
cacacttttg atgatttctg cccggagtgt cgtaccctag gtttgcaggg ttgtgcattc 1920
cagtccacta ttgctgagct tcagcgcctt aaaacggagg taggcaaaac ccgggagtct 1980
taa 1983

<210> SEQ ID NO 12
<211> LENGTH: 2016
<212> TYPE: DNA
<213> ORGANISM: Hepatitis E Virus

<400> SEQUENCE: 12
atgttctttt gctctttgca tggagatgcc gccatgcgct ctcgggctct tctgtttttg 60
ctcctcgtgt ttttgcctat gctgcccgcg ccaccggccg gtcagtcgtc tggccgtcgc 120
cgcgggcggc gcagcggcgg taccggcggt ggtttctggg gtgaccgggt tgattctcag 180
cccttcgccc tccccctatat tcatccaacc aatcccttcg catccgacat tccaaccgca 240
accggggctg gagctcgccc tcggcagcca gcccgtccac tcggctccgc ttggcgcgac 300
caatcccagc gccccgccgc tcctgcccgt cgccgacctg ccccagctgg ggcttcgccg 360
ctaacagctg ttgccccagc cccgacact gccccggttc ccgacgtgga ctcccgtggt 420
gctatattgc gccgccagta caacttgtcc acgtcaccgc ttacgtccac tatcgctact 480
ggcactaatc ttgtgctata tgctgcccca ctgagccctc tgctccctct ccaggatggg 540
actaatactc atatcatggc cactgaggcc tctaactatg ctcagtatcg cgttgtccgt 600
gccactattc ggtaccggcc tctggtgccg aatgcggttg gcgggtacgc catatccatc 660
tccttttggc ctcagacaac aaccaccccg acctccgtcg acatgaattc catcacctct 720
accgatgtcc gtatcctcgt tcagcctggt atagcctctg agcttgtgat ccctagtgag 780
cgcctgcatt atcgcaatca gggttggcgc tcggttgaga cttctggtgt tgcggaggag 840
gaggctacct ctggccttgt tatgctctgt attcatggat ctcctgtaaa ttcctacact 900
aatacaccct atactggtgc tctcggcttg ctcgattttg cgcttgagct tgaatttcgt 960
aatttgacac ctggcaatac gaatacgcgc gtctctcgtt attctagtag tgcgcgccac 1020
aagttacgcc gagggcctga tggcactgcc gagttgacca ccactgctgc tacacgtttc 1080
atgaaagatc tccattttac cgggactaat ggtgttggtg aggttggccg tggtattgcg 1140
ctaactctgt ttaatcttgc tgatacgctt ctcggcgggc tcccgacaga attgatttcg 1200
tcggccggag gccaattgtt ttactcacgc cccgtcgtct cagccaatgg cgagccgaca 1260
gtgaaactct acacctcagt tgagaatgcc cagcaggaca agggtatagc cattccacat 1320
gatattgacc ttggtgagtc ccgagttgtg attcaggatt atgataatca acacgagcaa 1380
gaccgcccca cccccttcccc tgccccctca cgtcctttct cagttcttcg tgctaatgat 1440
gtgctttggc tttcattgac ggctgctgaa tacgatcaaa ctacttatgg ttcttccact 1500
aatcctatgt atgtttctga cactgtgaca tttgttaatg tagcgaccgg tgcccagggg 1560
gtttctcgtt ccctggactg gtctaaagtc accctcgatg gtcggccgct tacaacaatt 1620
cagcagtatt ctaagacctt ctttgtccta cctcttcgtg gtaagctctc tttctgggag 1680
gctggcacta ctaaagctgg ctacccttat aattataaca ctactgccag tgatcagatc 1740

-continued

| | |
|---|---|
| ttaattgaaa atgcacctgg tcaccgagtc tgtatttcca cctatactac taatcttggt | 1800 |
| tccggccctg tctctatttc tgccgttggt gtcctcgcac cccattctgt gctggccgct | 1860 |
| ttggaggata ccgttgatta ccctgctcgt gctcatactt tcgatgattt ctgccctgag | 1920 |
| tgccgtgcgc tcggtctcca gggctgcgct tttcaatcga ctgtcgctga gctgcagcgt | 1980 |
| cttaaaatga aggtgggtaa aacccgggag tattga | 2016 |

METHODS AND COMPOSITIONS FOR INHIBITING HEPATITIS E VIRUS

RELATED APPLICATION(S)

This application is the U.S. National Stage of International Application No. PCT/US2017/052769, filed on Sep. 21, 2017, published in English, which claims the benefit of U.S. Provisional Application No. 62/398,297, filed Sep. 22, 2016. The entire teachings of the above Applications are incorporated herein by reference.

INCORPORATION BY REFERENCE OF MATERIAL IN ASCII TEXT FILE

This application incorporates by reference the Sequence Listing contained in the following ASCII text file:

a) File name: 53911003002_Seq_Listing.txt; created May 7, 2019, 42 KB in size.

BACKGROUND

Hepatitis E, transmitted by the hepatitis E virus (HEV), is the leading cause of enterically-transmitted viral hepatitis globally and a major public health threat in developing countries. In the general population, HEV-associated mortality is roughly 1%. However, the risk to pregnant women is significantly higher, reaching as high as 25% amongst women with HEV infections during their third trimester, resulting in 70,000 deaths and 3,000 stillbirths every year. While most HEV infections occur in developing countries, recent epidemiological studies have found a high seroprevalence of anti-HEV antibodies in industrialized countries (Dalton, H. R., et al. *Lancet Infect Dis* 8, 698-709 (2008)), suggesting exposure to the virus from travel to HEV endemic areas or from contact with pigs, a major reservoir of HEV. In a majority of cases, HEV causes an acute infection, but amongst immunocompromised—patients notably organ transplant recipients (Schildgen, O., et al. *N Engl J Med* 358, 2521-2522; author reply 2522 (2008); Kamar, N. et al. *N Engl J Med* 358, 811-817 (2008)) and individuals co-infected with HIV (Dalton, H. R., et al. *N Engl J Med* 361, 1025-1027 (2009))—HEV can progress to chronicity.

Pegylated interferon (IFN) and the nucleoside analogue ribavirin (RBV) have been used to treat HEV infection, but the use of these drugs is not recommended in certain patient groups, including pregnant women and organ transplant recipients. Although a vaccine for preventing HEV infection has been developed, it is not available in most countries Zhang, J. et al. *N Engl J Med* 372, 914-922 (2015)). Moreover, HEV isolates resistant to RBV have been identified (Debing, Y. et al. *Gastroenterology* 147, 1008-1011 e1007; quiz e1015-1006, doi:10.1053/j.gastro.2014.08.040 (2014)).

Accordingly, there is a significant unmet need for an anti-HEV therapeutic having broad applicability and/or enhanced efficacy.

SUMMARY OF THE INVENTION

In one aspect, the present invention provides a method of inhibiting hepatitis E virus (HEV) release from a cell that is infected with an HEV, comprising contacting the cell with an agent that inhibits one or more activities of HEV open reading frame 3 (ORF3) protein, wherein the one or more ORF3 activities are selected from, e.g., ion channel activity, multimerization activity, and/or viroporin activity.

In another aspect, the present invention also provides a method of treating a HEV infection in a subject in need thereof, comprising administering to the subject an effective amount of an agent that inhibits one or more activities of HEV ORF3 protein, wherein the one or more activities are selected from, e.g., ion channel activity, multimerization activity, and/or viroporin activity.

In other aspects, the present invention provides a method of identifying an agent that inhibits HEV infectivity, wherein the method comprises: a) introducing into a cell culture 1) a nucleic acid that comprises an HEV open reading frame 2 (ORF2) nucleotide sequence, 2) a nucleic acid that comprises an HEV ORF3 nucleotide sequence, and 3) a nucleic acid that i) comprises a reporter gene and an HEV ORF1 nucleotide sequence and ii) lacks HEV ORF2 and ORF3 nucleotide sequences. The method also comprises contacting the cell culture in step a) with an agent to be tested for anti-HEV activity, and further, harvesting the cell culture media from the cell culture that has been contacted with the agent. The harvest media is combined with a naïve cells in cell culture. The method further comprises measuring a level of activity of the reporter gene in the naïve cell culture; and comparing the level of reporter activity in the naïve cell culture measured in step e) to a reference activity level, wherein a decrease in measured activity level as compared to the reference activity level indicates that the agent inhibits HEV infectivity.

The methods described herein facilitate the identification of new HEV therapeutics and provide new therapeutic approaches to the treatment of hepatitis E in HEV-infected patients.

BRIEF DESCRIPTION OF THE DRAWINGS

The patent or application file contains at least one drawing executed in color. Copies of this patent or patent application publication with color drawings will be provided by the Office upon request and payment of the necessary fee.

FIG. 1A is a schematic representation of the predicted transmembrane topology (THMM Server v. 2.0) of HEV ORF3 protein (Kernow C1/p6). FIG. 1B shows HEV ORF3 protein associates with the ER membrane. HepG2C3A cells lentivirally transduced with HEV ORF3-HA were stained with anti-HA and anti-calnexin antibodies. Nuclei were stained with Hoechst dye. Shown are representative images of at least triplicate experiments. FIG. 1C shows results of a co-immunoprecipitation assay of FLAG-ORF3 and ORF3-HA in HepG2C3A cells. Cells were transduced with FLAG-ORF3 and/or ORF3-HA lentivirus and lysed 72 hours post-transduction. Cell lysates were subjected to immunoprecipitation with an anti-FLAG antibody. FIG. 1D is a Western Blot of cell lysates from cells lentivirally transduced to express ORF3-HA or mock transduced, analyzed by blotting with an anti-HA antibody. The monomer and oligomers are indicated with arrowhead and arrows, respectively.

FIG. 2A shows infection kinetics of transcomplemented HEV in HepG2C3A cells. Cell culture supernatants from naïve HepG2C3A, or HepG2C3A cells transduced with HEV ORF2 or/and ORF3 were collected 5 days post-transfection with rHEVΔORF2/3[Gluc] RNA. Naïve HepG2C3A cells were incubated with these supernatants. After 12 hours, cells were washed and Gaussia luciferase (Glue) activity quantified in the cell culture supernatants at the indicated time points. In FIG. 2B, 5 days following transfection of rHEVΔORF2/3[Gluc] RNA into HepG2C3A, or HepG2C3A cells transduced with HEV ORF2 or/and ORF3, lysates were used to infect naïve HepG2C3A cells. Gluc activity was measured in the supernatants 4 days post-infection. Shown are averages and standard deviations of triplicate measurements of three independent experiments.

FIG. 3A shows that IAV M2 can substitute ORF3 function. Cell culture supernatants from naïve HepG2C3A, or HepG2C3A cells transduced with HEV ORF2 and ORF3, M2 or M2(A30P), were collected 5 days post-transfection with rHEVΔORF2/3[Gluc] RNA. Naïve HepG2C3A cells were incubated with these supernatants. After 12 hours, cells were washed and Gaussia luciferase activity quantified in the cell culture supernatants 4 days later. Data represent the mean±SD (n=6-9). FIG. 3B shows current-voltage relationship of *X. laevis* oocytes expressing HEV ORF3, IAV M2, IAV M2(A30P) or control oocytes. During the current recording, the oocytes were bathed in Ringer solution. The standard voltage-clamp protocol consisted of rectangular voltage pulses from −90 to +60 mV in 10-mV increments applied from a holding voltage of −60 mV. Each point represents the steady-state current (average current between 4000-5000 ms) at the corresponding voltage step. Data represent the mean±SD (n=5).

FIG. 4A shows the identification via alanine scanning mutagenesis of positions within HEV ORF3 involved in the release of infectious virions. HEV ORF3 mutants generated by changing triplets of amino acids to alanines across the entire ORF3 protein were lentivirally delivered to HepG2C3A cells expressing ORF2. Dually transduced cells were subsequently transfected with rHEVΔORF2/3[Gluc] RNA. Five days post-transfection supernatants were collected and used to infect naïve HepG2C3A cells. Gaussia luciferase activity was quantified in the producer cells (bottom panel) and in the cell culture supernatant 4 days post-infection (top panel). The putative transmembrane regions (TM) are underlined. The asterisk marks the serine residue of ORF3, which can be phosphorylated. The two boxes mark the PXXP motifs within ORF3. In FIG. 4B, HepG2C3A cells lentivirally transduced with HA-tagged wild-type or the indicated ORF3 mutant were stained with anti-HA and anti-calnexin antibodies. Nuclei were stained with Hoechst dye. Shown are representative images of triplicate experiments. FIG. 4C shows a current-voltage relationship of *X. laevis* oocytes expressing HEV wild-type or the indicated ORF3 mutants. Experiments were conducted as detailed in FIGS. 3A and 3B. Data represent the mean±SD (n=5).

FIG. 5A is a schematic representation of the wild-type HEV and rHEVΔORF2/3[Gluc] genomes and the bicistronic lentiviral constructs for expressing ORF2 and ORF3. FIG. 5B is a schematic representation of the transcomplementation system for packaging HEV virions. FIG. 5C is a representative flowcytometry plot demonstrating efficient ORF2 and ORF3 expression. HepG2C3A cells were transduced with LVX-ORF2-IRES-zsGreen and/or LEX-ORF3-IRES-mCherry or not transduced. Flowcytometric analysis was performed 4 days following transduction to quantify the frequencies of ORF2 and/or ORF3 expressing cells.

FIG. 6A is a schematic representation of the bicistronic lentiviral constructs for expressin HEV ORF2, ORF3, IAV M2 and IAV M2(A30P). FIG. 6B shows representative flowcytometry plots demonstrating efficient ORF2 and ORF3, IAV M2 or M2(A30P) expression. HepG2C3A cells were transduced with LVX-ORF2-IRES-zsGreen and/or LEX-[ORF3 or M2 or M2(A30P)]-IRES-mCherry or not transduced. Flowcytometric analysis was performed 4 days following transduction to quantify the frequencies of ORF2 and/or ORF3 and M2 expressing cells. FIG. 6C is a schematic representation of SP6 driven constructs used for in vitro transcription of HEV ORF3, IAV M2 and IAV M2(A30P) mRNAs. FIG. 6D shows that HEV ORF3 expressed in *X. laevis* oocytes localizes to the plasma membrane. Water-injected and HEV ORF3 mRNA-injected oocytes were immunolabeled with polyclonal ORF3 antibody and analyzed by confocal microscopy.

In FIG. 7A the cell lysates from HepG2C3A cells lentivirally transduced to express HA-tagged wild-type ORF3, the indicated alanine mutants of ORF3, or mock transduced were analyzed by Western blot with anti-HA or anti-actin antibodies. In FIG. 7B, HepG2C3A cells were lentivirally transduced with HA-tagged wild-type or the indicated ORF3 mutants and stained with anti-HA and anti-calnexin antibodies. Nuclei were stained with Hoechst dye. Shown are representative images of at least triplicate experiments.

FIGS. 8A-8C illustrate ion channel activity of different ORF3 mutants. FIG. 8A shows that wild-type or alanine mutants of HEV ORF3 expressed in *X. laevis* oocytes localize to the plasma membrane. Water-injected and HEV ORF3 mRNA-injected oocytes were immunolabeled with polyclonal ORF3 antibody and analyzed by confocal microscopy. FIG. 8B shows current-voltage relationship of *X. laevis* oocytes expressing HEV wild-type or the indicated ORF3 mutants. Experiments were conducted as detailed in FIGS. 3A and 3B. Data represent the mean±SD (n=5). FIG. 8C summarizes the features of triple alanine ORF3 mutants that do not support HEV release.

FIG. 10A is a schematic of transcomplementation platform. FIG. 10B indicates that transfection of rHEVΔORF2/3[Gluc] leads to equivalent HEV genome replication in ORF2/3 and non-expressing cells. Supernatants from ORF2/3 and non-expressing HepG2C3A cells that were transfected with rHEVΔORF2/3[Gluc] were used to infect naïve HepG2C3A. Infectious virions were released only in the presence of ORF2/3 in the producer cell.

FIGS. 12A-12C show an experimental overview of testing of known ion channel inhibitors for activity against HEV ORF3. FIG. 12A is a table indicating the seven ion channel inhibitors tested. FIG. 12B shows that HepG2C3a cells transduced with HEV ORF2 and HEV ORF3 were transfected with a recombinant HEV construct, rHEVΔORF2/3 [Gluc], expressing HEV ORF1 and a secreted Gaussia luciferase (Gluc) reporter gene. It was hypothesized that treatment with viroporin inhibitors would result in reduced release of infectious virions into supernatant from these "producer" HepG2C3a cells. FIG. 12C describes an experimental design for testing ion channel inhibitors: A single clone-derived cell line highly expressing ORF2 and ORF3 (named HepG2C3a 1F4) was used as a producer cell line to generate infectious virions. The 1F4 cells were pre-treated with each drug in three dilutions for 4-6 hours, and then transfected with rHEVΔORF2/3[Gluc]. The medium from these cells containing progeny virions was collected after 5 days and used to infect naïve HepG2C3a cells. The cells were infected for 12 hours and subsequently washed three times with PBS. On day 5 post-infection, Gluc levels were measured in the supernatant of these cells as a proxy for infection level.

DETAILED DESCRIPTION OF THE INVENTION

Figure 1A:
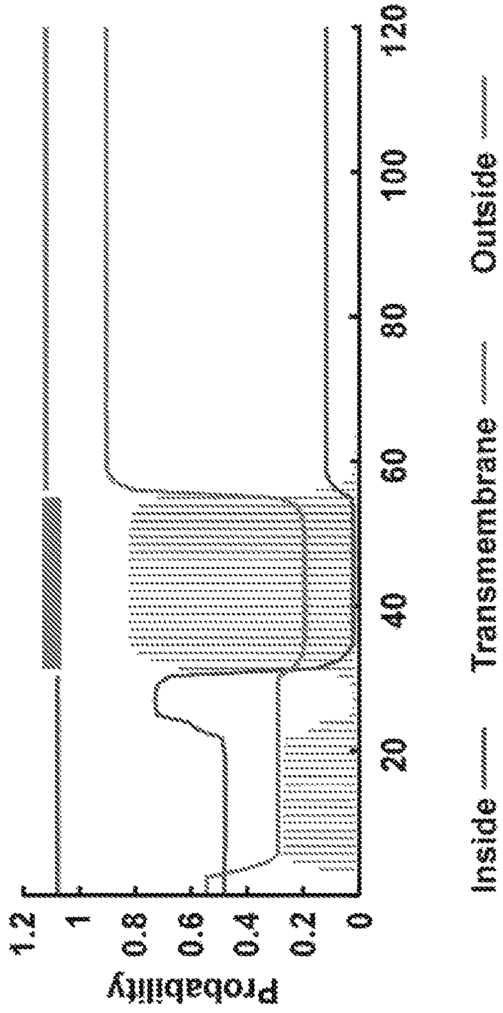
FIGS. 1A-1D demonstrate that ORF3 is a predicted transmembrane protein that associates with ER membranes and can form harm-oligomers.

A description of example embodiments of the invention follows.

HEV is a quasi-enveloped, positive(+)-sense, single-stranded RNA virus of the Hepeviridae family with three open reading frames (ORB). ORF1 encodes a non-structural polyprotein comprised of a methyltransferase, papain-like cysteine protease, RNA helicase, and RNA-dependent RNA polymerase (Cao and Meng, *Emerging microbes & infections* 1, e17, doi:10.1038/emi.2012.7 (2012)). ORF2 encodes the viral capsid protein and is involved in virion assembly, interaction with the host cell, and immunogenicity. It contains three glycosylation sites necessary for formation of infectious particles (Ahmad, I. et al., *Virus research* 161, 47-58, (2011)). In contrast, ORF3 and its corresponding function(s) have been largely elusive. The smallest ORF of the HEV genome, ORF3 is translated from a subgenomic RNA into a protein of 113-155 amino acids.

The present invention is based, in part, on the identification of a previously unknown HEV ORF3 function. As described herein, ORF3 forms multimedia complexes associated with intracellular endoplasmic reticulum (ER)-derived membranes via homophilic interactions, which complexes possess ion channel and/or viroporin function. To date, viroporins have been identified in nine different viruses, including six enveloped viruses (HCV, HIV, IAV, rotavirus, Alpha-/Sindbisviruses and Coronaviruses) but only in three non-enveloped viruses (simian virus 40 (SV40), coxsackie B virus (CBV) and polio virus (reviewed in Sze, C. W. & Tan, Y. J. *Viruses* 7, 3261-3284 (2015)). For both enveloped and non-enveloped viruses, viroporin function is frequently linked to virus release, but the underlying mechanism remains incompletely understood.

As demonstrated herein, the function of HEV ORF3 can be maintained by expressing the well-characterized viroporin influenza A virus (IAV) M2 protein. Further evidence of ORF3's ion channel function has been demonstrated by its ability to increase the flux of cations when expressed in *Xenopus laevis* oocytes. Furthermore, using alanine scanning mutagenesis, amino acid positions in ORF3 that are important for its formation of multimedia complexes, ion channel activity, and release of infectious particles have been identified.

Methods of Regulating ORF3 Activity

In one aspect, the present invention provides a method of inhibiting HEV release from a cell that is infected with an HEV, comprising contacting the cell with an agent that inhibits one or more activities of HEV ORF3 protein, wherein the one or more ORF3 activities are selected from ion channel activity, multimerization activity, or viroporin activity, or a combination thereof.

As used herein, the phrase "inhibiting HEV release" refers to inhibiting HEN/release completely or partially from an infected cell.

As used herein, the phrase "HEV ORF3 protein" refers to a protein encoded by the third open reading frame of a HEV genome. As used herein, "HEV genome" refers to the genome of any one of the various HEV genotypes or quasispecies. As those of skill in the art would appreciate, the methods described herein can be used to inhibit an ORF3 protein of any genotype or quasispecies of HEV. In some embodiments, an ORF3 protein possesses any one or more of ion channel activity, multimerization activity, or viroporin activity. Examples of HEV ORF3 proteins are shown in Table 1 below.

TABLE 1

Examples of ORF3 protein sequences

| | |
|---|---|
| Genotype 3<br>GenBank: AFD33685.1 | MGSPCALGLFCCCSSCFCLCCPRERPASRLAVVVGGAAAVPA<br>VVSGVTGLILSPSPSPIFIQPTPSPPISFHNPGLELALGSRPAPLAP<br>LGVTSPSAPPLPPAVDLPQLGLRR (SEQ ID NO: 1) |
| Genotype 1<br>ID: P69616 | MGSRPCALGLFCCCSSCFCLCCPRHRPVSRLAAVVGGAAAVP<br>AVVSGVTGLILSPSQSPIFIQPTPSPPMSPLRPGLDLVFANPPDH<br>SAPLGVTRPSAPPLPHVVDLPQLGPRR (SEQ ID NO: 2) |
| Genotype 2<br>ID: Q03499 | MGSPPCALGLFCCCSSCFCLCCPRHRPVSRLAAVVGGAAAVP<br>AVVSGVTGLILSPSQSPIFIQPTPLPQTLPLRPGLDLAFANQPGH<br>LAPLGEIRPSAPPLPPVADLPQPGLRR (SEQ ID NO: 3) |
| Genotype 4<br>ID: BAG32135.1 | MEMPPCALGLFCFCSSCFCLCCPRHRPVSRLAVAAGGAAAVP<br>AVVSGVTGLILSPSPSPIFIQPIPSHPTFQPQPGLELALGSQPVHS<br>APLGATNPSAPPLLPVADLPQLGLRR (SEQ ID NO: 4) |

In some embodiment, the HEV ORF3 protein comprises the sequence set forth in SEQ ID NO: 1. However, one of skill in the art would appreciate that the present method can be used to inhibit the activity (e.g., ion channel activity, multimerization activity, or viropotin activity, or a combination thereof) of an HEV ORF3 protein. Thus, in certain embodiments, the HEV ORF3 protein comprises a sequence that is at least 70%, at least 75%, at least 80%, at least 85%, at least 90%, at least 95%, at least 98%, or at least 99% identical to SEQ ID NO: 1.

In various embodiments, the HEV protein comprises the sequence set forth in any one of SEQ ID NOs: 2-4. In certain embodiments, the HEV ORF3 protein comprises a sequence that is at least 70%, at least 75%, at least 80%, at least 85%, at least 90%, or at least 95% identical to any one or SEQ ID NOs: 2-4.

Various suitable agents can be used in the present invention. In some embodiments, the agent is a small molecule. Examples of small molecules include organic compounds, organometallic compounds, inorganic compounds, and salts of organic, organometallic and inorganic compounds. Atoms in a small molecule are typically linked together via covalent and/or ionic bonds. The arrangement of atoms in a small organic molecule may represent a chain (e.g. a carbon-carbon chain or a carbon-heteroatom chain), or may represent a ring containing carbon atoms, e.g. benzene or a polycyclic system, or a combination of carbon and heteroatoms, i.e., heterocycles such as a pyrimidine or quinazoline. Small molecule inhibitors generally have a molecular weight that is less than about 5,000 daltons. For example, such small molecules can be less than about 1000 daltons, less than about 750 daltons or even less than about 500 daltons. Small molecules and other non-peptidic ORF3 inhibitors can be found in nature (e.g., identified, isolated, purified) and/or produced synthetically (e.g., by traditional organic synthesis, bio-mediated synthesis, or a combination thereof). See e.g. Ganesan, Drug Discov. Today 7(1): 47-55 (January 2002); Lou, Drug Discov. Today, 6(24): 1288-1294 (December 2001). Examples of naturally occurring small molecules include, but are not limited to, hormones, neurotransmitters, nucleotides, amino acids, sugars, lipids, and their derivatives.

In some embodiments, the agent can bind to one or more regions of the ORF3 protein. For example, the agent can bind to (or make contact with) the ORF3 protein at any one or more residues selected from the residues at positions 11-13, 29-40, 59-61, 71-73, 80-85, 86-89, or 95-98 of SEQ ID NO: 1.

As those of skill in the art would appreciate, in certain embodiments, the agent can bind to one or more regions of an ORF3 protein comprising any one of SEQ ID NOs: 2-4, wherein the one or more regions correspond to (e.g., possess equivalent functions to) any one or more residues selected from the residues at positions 11-13, 29-40, 59-61, 71-73, 80-85, 86-89, or 95-98 of SEQ ID NO: 1.

In certain embodiments, the agent binds to a channel-forming region of an ORF3 protein. In other embodiments, the agent inhibits ORF3 protein ion channel activity, for example, by binding to a region of ORF3 protein comprising, e.g., amino acid positions 11-13 or 59-61, or both, of SEQ ID NO: 1.

In some embodiments, the agent is contacted with a cell that is infected with HEV to inhibit HEV release from the cell. The present method is suitable for any cell that is infected with an HEV. Examples of such cells include hepatocytes and gastrointestinal cells, as well as cells derived from hepatocytes or gastrointestinal cells.

In another aspect, the present invention also provides a method of treating a HEV infection in a subject in need thereof. In some embodiments, the method comprises administering to the subject an effective amount of an agent that inhibits one or more activities of a HEV ORF3 protein, wherein the one or more activities are selected from ion channel activity, multimerization activity, or viroporin activity, or a combination thereof.

As used herein, the terms "treat," "treating," or "treatment," refer to counteracting a medical condition (e.g., a condition related to HEV infection) to the extent that the medical condition is improved according to a clinically-acceptable standard.

As used herein, "subject" refers to a mammal (e.g., human, non-human primate, cow, sheep, goat, horse, swine, dog, cat, rabbit, guinea pig, rat, mouse). In a particular embodiment, the subject is a human. A "subject in need thereof" refers to a subject (e.g., patient) who has, or is at risk for developing, a disease or condition that can be treated (e.g., improved, ameliorated, prevented) by an agent that inhibits one or more ORF3 protein activities selected from ion channel activity, multimerization activity, or viroporin activity, or a combination thereof. In certain embodiments, the subject is a pregnant female. In other embodiments, the subject is immunocompromised. In some embodiments, the immunocompromised subject is a subject who has undergone an organ transplant or a subject infected with human immunodeficiency virus (HIV), or both. In certain embodiments, the subject is an immunocompromised pregnant female.

An agent that inhibits one or more activities of HEV ORF3 protein (and thereby treats a condition related to HEV infection) can be administered to a subject in need thereof by a variety of routes of administration including, for example, oral, dietary, topical, transdermal, or parenteral (e.g., intra-arterial, intravenous, intramuscular, subcutaneous injection, intradermal injection) routes of administration, depending on the agent. Administration can be local or systemic. The chosen mode of administration can vary depending on the particular agent selected. The actual dose of a therapeutic agent and treatment regimen can be determined by a skilled physician, taking into account the nature of the condition being treated, and patient characteristics.

As defined herein, an "effective amount" refers to an amount of an agent that, when administered to a subject, is sufficient to achieve a desired therapeutic effect (treats a condition related to HEV infection) in the subject under the conditions of administration, such as an amount sufficient to inhibit one or more activities of HEV ORF3 protein (e.g., ion channel activity, multimerization activity, or viroporin activity) in the subject. Various methods of assessing the effectiveness of the agent for treating a condition related to HEV infection are known in the art. For example, the titer can be measured in the sera of a patient according to methods known in the art. Measuring the titer can provide an indication of infectivity. Other methods of assessing infectivity of HEV from patient sera are known in the art.

An effective amount of the agent to be administered can be determined by a clinician of ordinary skill using the guidance provided herein and other methods known in the art, and is dependent on several factors including, for example, the particular agent chosen, the subject's age, sensitivity, tolerance to drugs and overall well-being. For example, suitable dosages for a small molecule can be from about 0.001 mg/kg to about 100 mg/kg, from about 0.01 mg/kg to about 100 mg/kg, from about 0.01 mg/kg to about 10 mg/kg, from about 0.01 mg/kg to about 1 mg/kg body weight per treatment. Determining the dosage for a particular agent, patient and stage of HEV infection is well within the abilities of one of skill in the art.

An agent that inhibits one or more activities of HEV ORF3 protein (e.g., ion channel activity, multimerization activity, or viroporin activity) can be administered in a single dose or as multiple doses, for example, in an order and on a schedule suitable to achieve a desired therapeutic effect (e.g., treatment of a condition related to HEV infection). Suitable dosages and regimens of administration can be determined by a clinician of ordinary skill.

In some embodiments, the method comprises administering an effective amount of an agent that inhibits one or more activities of a HEV ORF3 protein (e.g., ion channel activity, multimerization activity, or viroporin activity) in combination with one or more additional therapeutic agents (e.g., additional agents that treat a condition related to HEV infection). Such agents are known in the art and include, for example, interferon (e.g., pegylated interferon) or ribavirin. Thus, in some embodiments, the method further comprises administering an effective amount of interferon or ribavirin, or both, to the subject. As those of skill in the art would appreciate, combination therapies that include agents known to have a negative side effect to a subset of subjects would typically not be administered to that subset of subjects. For example, a combination therapy that includes interferon or ribavirin, or both, would typically not be adminstered to pregnant females and/or immunocomprised subjects.

When administered in a combination therapy, the agent can be administered before, after or concurrently with the other therapy (e.g., administration of interferon or ribavirin, or both). When co-administered simultaneously (e.g., concurrently), the agent and other therapy can be in separate formulations or the same formulation. Alternatively, the agent and other therapy can be administered sequentially, as separate compositions, within an appropriate time frame as determined by a skilled clinician (e.g., a time sufficient to allow an overlap of the pharmaceutical effects of the therapies).

In some embodiments the agent can be administered to a subject in a composition or formulation comprising the agent and one or more pharmaceutically acceptable carriers or excipients. Suitable pharmaceutical carriers typically will contain inert ingredients that do not interact with the agent or nucleic acid. Suitable pharmaceutical carriers for parenteral administration include, for example, sterile water, physiological saline, bacteriostatic saline (saline containing about 0.9% mg/ml benzyl alcohol), phosphate-buffered saline, Hank's solution, Ringer's lactate and the like. Formulations can also include small amounts of substances that enhance the effectiveness of the active ingredient (e.g., emulsifying agents, solubilizing agents, pH buffering agents, wetting agents). Methods of encapsulation compositions (such as in a coating of hard gelatin or cyclodextran) are known in the art. For inhalation, the agent can be solubilized and loaded into a suitable dispenser for administration (e.g., an atomizer or nebulizer or pressurized aerosol dispenser).

The agent can be administered as a neutral compound or as a salt or ester. Pharmaceutically acceptable salts include those formed with free amino groups such as those derived from hydrochloric, phosphoric, acetic, oxalic or tartaric acids, and those formed with free carboxyl groups such as those derived from sodium, potassium, ammonium, calcium, ferric hydroxides, isopropylamine, triethylamine, 2-ethylamino ethanol, histidine, procaine, etc. Salts of compounds containing an amine or other basic group can be obtained, for example, by reacting with a suitable organic or inorganic acid, such as hydrogen chloride, hydrogen bromide, acetic acid, perchloric acid and the like. Compounds with a quaternary ammonium group also contain a counteranion such as chloride, bromide, iodide, acetate, perchlorate and the like. Salts of compounds containing a carboxylic acid or other acidic functional group can be prepared by reacting with a suitable base, for example, a hydroxide base. Salts of acidic functional groups contain a countercation such as sodium or potassium.

In some embodiments, pharmaceutical compositions comprising an agent that inhibits one or more activities of a HEV ORF3 protein (e.g., ion channel activity, multimerization activity, or viroporin activity) can also include one or more other therapeutic agents (e.g., interferon or ribavirin, or both) known to treat a condition related to HEV infection.

Standard pharmaceutical formulation techniques can be employed, such as those described in Remington's Pharmaceutical Sciences, Mack Publishing Company, Easton, Pa. Suitable pharmaceutical carriers for parenteral administration include, for example, sterile water, physiological saline, bacteriostatic saline (saline containing about 0.9% mg/ml benzyl alcohol), phosphate-buffered saline, Hank's solution, Ringer's lactate and the like. Formulations can also include small amounts of substances that enhance the effectiveness of the active ingredient (e.g., emulsifying, solubilizing, pH buffering, wetting agents). Methods of encapsulation compositions (such as in a coating of hard gelatin or cyclodextran) are known in the art. For inhalation, the agent can be solubilized and loaded into a suitable dispenser for administration (e.g., an atomizer or nebulizer or pressurized aerosol dispenser).

Methods of Identifying Agents that Inhibit HEV Infectivity

As described herein, the present invention also relates to a system (e.g., a transcomplementation system) that enables the identification of agents that inhibit various aspects of the HEV lifecycle, and which can lead to the identification of agents that inhibit HEV infectivity.

Thus, in other aspects, the present invention also provides a method of identifying an agent that inhibits HEV infectivity, also referred to herein as a transcomplementation method. In some embodiments, the method comprises introducing into a cell culture 1) a nucleic acid that comprises an HEV open reading frame 2 (ORF2) nucleotide sequence, 2) a nucleic acid that comprises an HEV ORF3 nucleotide sequence, and 3) a nucleic acid that i) comprises a reporter gene and an HEV ORF1 nucleotide sequence and ii) lacks HEV ORF2 and ORF3 nucleotide sequences. The method further comprises, in a subsequent step, contacting the cell culture with an agent to be tested for anti-HEV activity. In some embodiments, the method comprises harvesting the cell culture media from the cell culture that has been contacted with the agent, combining the harvested media with a naïve cell culture, and measuring a level of activity of the reporter gene in the naïve cell culture. In various embodiments, the method also comprises comparing the level of reporter activity measured in the naïve cell culture to a reference activity level, wherein a decrease in the measured activity level as compared to the reference activity level indicates that the agent inhibits HIV infectivity.

As used herein, an agent that "inhibits HEV infectivity" refers to an agent that causes a reduction (completely or partially) in HEV function. A reduction in HEV function can result from a variety of inhibitory effects of an agent in any one or more phases of the HEV lifecycle. Generally, the present invention is suitable for identifying an agent that inhibits, e.g., HEV release from a cell, HEV replication, or HEV assembly, or a combination thereof. In certain embodiments, the agent inhibits ORF1 protein activity, ORF2 protein activity, or ORF3 protein activity, or a combination thereof, thereby inhibiting HEV infectivity.

The term "nucleic acid" refers to a polymer having multiple nucleotide monomers. A nucleic acid can be single- or double-stranded, and can be DNA (e.g., cDNA or genomic DNA), RNA, or hybrid polymers (e.g., DNA/RNA). Nucleic acids can be chemically or biochemically modified and/or can contain non-natural or derivatized nucleotide bases. Nucleic acids can also include, for example, conformationally restricted nucleic acids (e.g., "locked nucleic acids" or "LNAs," such as described in Nielsen et at, J. Viomol. Struct. Dyn. 17:175-91, 1999), morpholinos, glycol nucleic acids (GNA) and threose nucleic acids (TNA).

Methods of introducing nucleic acids into a cell are well known in the art, and include, for example, transduction, transfection, transformation, and the like. As those of skill in the art would appreciate, the method selected will depend on the particular context (e.g., the nucleic acid to be introduced and/or the cells to be used for introducing the nucleic acid) to achieve, e.g., high efficiency. In certain embodiments, the different nucleic acid components (e.g., the nucleic acid that comprises an HEV ORF2 nucleotide sequence; the nucleic acid that comprises an HEV ORF3 nucleotide sequence; and the nucleic acid that i) comprises a reporter gene and an HEV ORF1 nucleotide sequence and ii) lacks HEV ORF2 and ORF3 nucleotide sequences) to be introduced into a cell culture in the transcomplementation system can be introduced by different methods. For example, nucleic acid(s) encoding ORF2 and ORF3 can be transduced into the cell culture using a viral vector (e.g., lentivirus), and the nucleic acid comprising the reporter gene and ORF1 can be transfected (e.g., by other non-viral means). As those of skill in the art would appreciate, a variety of combinations (e.g., transduction, transfection, transformation) can be used to introduce the nucleic acids into cells.

ORF1 and ORF2 nucleotide sequences within a HEV genome that are involved in ORF1 and ORF2 function are known and/or ascertainable in the art. See, e.g., Cao, D. and Meng, X. J. *Emerging microbes & infections* 1, e17, doi: 10.1038/emi.2012.7 (2012); and Ahmad, I., et al., *Virus research* 161(1): 47-58 (2011). Tables 2 and 3 below provide examples of ORF1 and ORF2 nucleotide sequences that can be used in the present invention.

TABLE 2

| Examples of ORF1 Nucleotide Sequences | |
|---|---|
| Genotype 1 | ATGGAGGCCCATCAGTTTATCAAGGCTCCTGGCATCACTAC |
| ID AF444002.1 | TGCTATTGAGCAGGCTGCTCTAGCAGCGGCCAACTCTGCCC |
| | TTGCGAATGCTGTGGTAGTTAGGCCTTTTCTCTCTCACCAG |
| | CAGATTGAGATCCTTATTAACCTAATGCAACCTCGCCAGCT |
| | TGTTTTCCGCCCCGAGGTTTTCTGGAACCATCCCATCCAGC |
| | GTGTTATCCATAATGAGCTGGAGCTTTACTGTCGCGCCCGC |
| | TCCGGCCGCTGCCTTGAAATTGGTGCCCACCCCCGCTCAAT |
| | AAATGACAATCCTAATGTGGTCCACCGTTGCTTCCTCCGTC |
| | CTGCCGGGCGTGATGTTCAGCGTTGGTATACTGCCCCTACC |
| | CGCGGGCCGGCTGCTAATTGCCGGCGTTCCGCGCTGCGCGG |
| | GCTCCCCGCTGCTGACCGCACTTACTGCTTCGACGGGTTTT |
| | CTGGCTGTAACTTTCCCGCCGAGACGGGCATCGCCCTCTAT |
| | TCTCTCCATGATATGTCACCATCTGATGTCGCCGAGGCTAT |
| | GTTCCGCCATGGTATGACGCGGCTTTACGCTGCCCTCCACC |
| | TCCCGCCTGAGGTCCTGTTGCCCCCTGGCACATACCGCACC |
| | GCGTCGTACTTGCTGATCCATGACGGCAGGCGCGTTGTGGT |
| | GACGTATGAGGGTGACACTAGTGCTGGTTATAACCACGAT |
| | GTTTCCAACCTGCGCTCCTGGATTAGAACCACTAAGGTTAC |
| | CGGAGACCACCCTCTCGTCATCGAGCGGGTTAGGGCCATTG |
| | GCTGCCACTTTGTCCTTTTACTCACGGCTGCCCCGGAGCCA |
| | TCACCTATGCCGTATGTCCCTTACCCCCGGTCTACCGAGGT |
| | CTATGTCCGATCGATCTTCGGCCCGGGTGGTACCCCCTCCC |
| | TATTTCCAACCTCATGCTCCACCAAGTCGACCTTCCATGCT |
| | GTCCCTGGCCATATCTGGGACCGTCTCATGTTGTTCGGGGC |
| | CACCCTAGATGACCAAGCCTTTTGCTGCTCCCGCCTAATGA |
| | CTTACCTCCGCGGCATTAGCTACAAGGTTACTGTGGGCACC |
| | CTTGTTGCCAATGAAGGCTGGAACGCCTCTGAGGACGCTCT |
| | TACAGCTGTCATCACTGCCGCCTACCTTACCATCTGCCACC |
| | AGCGGTACCTCCGCACTCAGGCTATATCTAAGGGGATGCGT |
| | CGCCTGGAGCGGGAGCATGCTCAGAAGTTTATAACACGCC |
| | TCTACAGTTGGCTCTTTGAGAAGTCCGGCCGTGATTATATC |
| | CCCGGCCGTCAGTTGGAGTTCTACGCTCAGTGTAGGCGCTG |
| | GCTCTCGGCCGGCTTTCATCTTGACCCACGGGTGTTGGTTTT |
| | TGATGAGTCGGCCCCCTGCCACTGTAGGACTGCGATTCGTA |
| | AGGCGGTCTCAAAGTTTTGCTGCTTTATGAAGTGGCTGGGC |
| | CAGGAGTGCACCTGTTTTCTACAACCTGCAGAAGGCGTCGT |
| | TGGCGACCAGGGCCATGACAACGAGGCCTATGAGGGGTCT |
| | GATGTTGACCCTGCTGAATCCGCTATTAGTGACATATCTGG |
| | GTCCTACGTAGTCCCTGGCACTGCCCTCCAACCGCTTTACC |
| | AAGCCCTTGACCTCCCCGCTGAGATTGTGGCTCGTGCAGGC |
| | CGGCTGACCGCCACAGTAAAGGTCTCCCAGGTCGACGGGC |
| | GGATCGATTGTGAGACCCTTCTCGGTAATAAAACCTTCCGC |
| | ACGTCGTTTGTTGACGGGGCGGTTTTAGAGACTAATGGCCC |
| | AGAGCGCCACAATCTCTCTTTTGATGCCAGTCAGAGCACTA |
| | TGGCGGCCGGCCCTTTCAGTCTCACCTATGCCGCCTCTGCT |
| | GCTGGGCTGGAGGTGCGCTATGTCGCCGCCGGGCTTGACC |
| | ACCGGGCGGTTTTTGCCCCCGGCGTTTCACCCCGGTCAGCC |
| | CCTGGCGAGGTCACCGCCTTCTGTTCTGCCCTATACAGGTT |

TABLE 2-continued

| Examples of ORF1 Nucleotide Sequences |
| --- |
| TAATCGCGAGGCCCAGCGCCTTTCGCTGACCGGTAATTTTT<br>GGTTCCATCCTGAGGGGCTCCTTGGCCCCTTTGCCCCGTTTT<br>CCCCCGGGCATGTTTGGGAGTCGGCTAATCCATTCTGTGGC<br>GAGAGCACACTTTACACCCGCACTTGGTCGGAGGTTGATGC<br>TGTTCCTAGTCCAGCCCAGCCCGACTTAGGTTTTACATCTG<br>AGCCTTCTATACCTAGTAGGGCCGCCACACCTACCCCGGCG<br>GCCCCTCTACCCCCCCCTGCACCGGATCCTTCCCCTACTCTC<br>TCTGCTCCGGCGCGTGGTGAGCCGGCTCCTGGCGCTACCGC<br>CGGGGCCCCAGCCATAACCCACCAGACGGCCCGGCATCGC<br>CGCCTGCTCTTTACCTACCCGGATGGCTCTAAGGTGTTCGC<br>CGGCTCGCTGTTTGAGTCGACATGTACCTGGCTCGTTAACG<br>CGTCTAATGTTGACCACCGCCCTGGCGGTGGGCTCTGTCAT<br>GCATTTTACCAGAGGTACCCCGCCTCCTTTGATGCTGCCTC<br>TTTTGTGATGCGCGACGGCGCGGCCGCCTACACATTAACCC<br>CCCGGCCAATAATTCATGCCGTCGCTCCTGATTATAGGTTG<br>GAACATAACCCAAAGAGGCTTGAGGCTGCCTAGCGGGAGA<br>CTTGCTCCCGCCTCGGTACCGCTGCATACCCACTCCTCGGG<br>ACCGGCATATACCAGGTGCCGATCGGTCCCAGTTTTGACGC<br>CTGGGAGCGGAATCACCGCCCCGGGGACGAGTTGTACCTT<br>CCTGAGCTTGCTGCCAGATGGTTCGAGGCCAATAGGCCGA<br>CCTGCCCAACTCTCACTATAACTGAGGATGTTGCGCGGACA<br>GCAAATCTGGCTATCGAACTTGACTCAGCCACAGACGTCG<br>GCCGGGCCTGTGCCGGCTGTCGAGTCACCCCCGGCGTTGTG<br>CAGTACCAGTTTACCGCAGGTGTGCCTGGATCCGGCAAGTC<br>CCGCTCTATTACCCAAGCCGACGTGGACGTTGTCGTGGTCC<br>CGACCCGGGAGTTGCGTAATGCCTGGCGCCGCCGCGGCTTC<br>GCTGCTTTCACCCCGCACACTGCGGCTAGAGTCACCCAGGG<br>GCGCCGGGTTGTCATTGATGAGGCCCCGTCCCTTCCCCCTC<br>ATTTGCTGCTGCTCCACATGCAGCGGGCCGCCACCGTCCAC<br>CTTCTTGGCGACCCGAATCAGATCCCAGCCATCGATTTTGA<br>GCACGCCGGGCTCGTTCCCGCCATCAGGCCCGATTTGGCCC<br>CCACCTCCTGGTGGCATGTTAGCCATCGCTGCCCTGCGGAT<br>GTATGTGAGCTAATCCGCGGCGCATACCCTATGATTCAGAC<br>CACTAGTCGGGTCCTCCGGTCGTTGTTCTGGGGTGAGCCCG<br>CCGTTGGGCAGAAGCTAGTGTTCACCCAGGCGGCTAAGGC<br>CGCCAACCCCGGTTCAGTGACGGTCCATGAGGCACAGGGC<br>GCTACCTACACAGAGACTACCATCATTGCCACGGCAGATG<br>CTCGAGGCCTCATTCAGTCGTCCCGAGCTCATGCCATTGTT<br>GCCTTGACGCGCCACACTGAGAAGTGCGTCATCATTGACGC<br>ACCAGGCCTGCTTCGCGAGGTGGGCATCTCCGATGCAATCG<br>TTAATAACTTTTTCCTTGCTGGTGGCGAAATTGGCCACCAG<br>CGCCCATCTGTTATCCCTCGCGGCAATCCTGACGCCAATGT<br>TGACACCTTGGCTGCCTTGCCGCCGTCTTGGGAGATTAGCG<br>CCTTCCATCAGTTGGCTGAGGAGCTTGGCCACAGACCTGCC<br>CCTGTGGCGGCTGTTCTACCGCCCTGCCCTGAGCTTGAACA<br>GGGCCTTCTCTACCTGCCCCAAGAACTCACCACCTGTGATA<br>GTGTCGTAACATTTGAATTAACAGATATTGTGCATTGTCGT<br>ATGGCCGCCCCGAGCCAGCGCAAGGCGGTGGTGTCCACGC<br>TCGTGGGCCGTTATGGCCGCCGCACAAAGCTCTACAATGCC<br>TCCCACTCTGATGTTCGCGACTCTCTCGCCCGTTTTATCCCG<br>GCCATTGGCCCCGTACAGGTTACAAGCTGTGAATTGTACGA<br>GCTAGTGGAGGCCATGGTCGAGAAGGGCCAGGACGGCTCC<br>GCCGTCCTTGACCTCGAGCTTTGTAGCCGCGACGTGTCCAG<br>GATCACCTTCTTCCAGAAAGATTGTAATAAATTCACCACGG<br>GGGAGACCATCGCCCATGGTAAAGTGGGCCAGGGCATTTC<br>GGCCTGGAGTAAGACCTTCTGTGCCCTTTTCGGCCCCTGGT<br>TCCGTGCTATTGAGAAGGCTATCCTGGCCCTGCTCCCTCAG<br>GGTGTGTTTTATGGGGATGCCTTTGATGACACCGTCTTCTC<br>GGCGGCTGTGGCCGCAGCAAAGGCATCCATGGTGTTTGAG<br>AATGACTTTTCTGAGTTTGATTCCACCCAGAATAATTTTTCC<br>TTGGGCCTAGAGTGTGGTATTATGGAGGAGTGTGGGATGCC<br>GCAGTGGCTCATCCGCTTGTACCACCTTATAAGGTCTGCGT<br>GGATTCTGCAGGCCCCGAAGGAGTCCCTGCGAGGGTTTTG<br>GAAGAAACACTCCGGTGAGCCCGGCACCCTTCTGTGGAAT<br>ACTGTCTGGAACATGGCCGTTATCACCCACTGTTATGATTT<br>CCGCGATCTGCAGGTGGCTGCCTTTAAAGGTGATGATTCGA<br>TAGTGCTTTGCAGTGAGTACCGTCAGAGCCCAGGGGCTGCT<br>GTCCTGATTGCTGGCTGTGGCCTAAAGTTGAAGGTGGATTT<br>CCGTCCGATTGGTCTGTATGCAGGTGTTGTGGTGGCCCCCG<br>GCCTTGGCGCGCTTCCTGATGTCGTGCGCTTCGCCGGTCGG<br>CTTACTGAGAAGAATTGGGGCCCTGGCCCCGAGCGGGCGG<br>AGCAGCTCCGCCTCGCTGTGAGTGATTTTCTCCGCAAGCTC<br>ACGAATGTAGCTCAGATGTGTGTGGATGTTGTCTCTCGTGT<br>TTATGGGGTTTCCCCTGGGCTCGTTCATAACCTGATTGGCA<br>TGCTAGAGGCTGTTGCTGATGGCAAGGCTCATTTCACTGAG<br>TCAGTGAAGCCAGTGCTTGACCTGACAAATTCAATTCTGTG<br>TCGGGTGGAATGA (SEQ ID NO: 5) |

TABLE 2-continued

| Examples of ORF1 Nucleotide Sequences | |
|---|---|
| Genotype 2 | ATGGAGGCCCACCAGTTCATTAAGGCTCCTGGCATCACTAC |
| AAA45730.1 | TGCTATTGAGCAAGCAGCTCTAGCAGCGGCCAACTCCGCCC |
| | TTGCGAATGCTGTGGTGGTCCGGCCTTTCCTTTCCCATCAG |
| | CAGGTTGAGATCCTTATAAATCTCATGCAACCTCGGCAGCT |
| | GGTGTTTCGTCCTGAGGTTTTTTGGAATCACCCGATTCAAC |
| | GTGTTATACATAATGAGCTTGAGCAGTATTGCCGTGCTCGC |
| | TCGGGTCGCTGCCTTGAGATTGGAGCCCACCCACGCTCCAT |
| | TAATGATAATCCTAATGTCCTCCATCGCTGCTTTCTCCACCC |
| | CGTCGGCCGGGATGTTCAGCGCTGGTACACAGCCCCGACT |
| | AGGGGACCTGCGGCGAACTGTCGCCGCTCGGCACTTCGTG |
| | GTCTGCCACCAGCCGACCGCACTTACTGTTTTGATGGCTTT |
| | GCCGGCTGCCGTTTTGCCGCCGAGACTGGTGTGGCTCTCTA |
| | TTCTCTCCATGACTTGCAGCCGGCTGATGTTGCCGAGGCGA |
| | TGGCTCGCCACGGCATGACCCGCCTTTATGCAGCTTTCCAC |
| | TTGCCTCCAGAGGTGCTCCTGCCTCCTGGCACCTACCGGAC |
| | ATCATCCTACTTGCTGATCCACGATGGTAAGCGCGCGGTTG |
| | TCACTTATGAGGGTGACACTAGCGCCGGTTACAATCATGAT |
| | GTTGCCACCCTCCGCACATGGATCAGGACAACTAAGGTTGT |
| | GGGTGAACACCCTTTGGTGATCGAGCGGGTGCGGGGTATT |
| | GGCTGTCACTTTGTGTTGTTGATCACTGCGGCCCCTGAGCC |
| | CTCCCCGATGCCCTACGTTCCTTACCCGCGTTCGACGGAGG |
| | TCTATGTCCGGTCTATCTTTGGGCCCGGCGGGTCCCCGTCG |
| | CTGTTCCCGACCGCTTGTGCTGTCAAGTCCACTTTTCACGCC |
| | GTCCCCACGCACATCTGGGACCGTCTCATGCTCTTTGGGGC |
| | CACCCTCGACGACCAGGCCTTTTGCTGCTCCAGGCTTATGA |
| | CGTACCTTCGTGGCATTAGCTATAAGGTAACTGTGGGTGCC |
| | CTGGTCGCTAATGAAGGCTGGAATGCCACCGAGGATGCGC |
| | TCACTGCAGTTATTACGGCGGCTTACCTCACAATATGTCAT |
| | CAGCGTTATTTGCGGACCCAGGCGATTTCTAAGGGCATGCG |
| | CCGGCTTGAGCTTGAACATGCTCAGAAATTTATTTCACGCC |
| | TCTACAGCTGGCTATTTGAGAAGTCAGGTCGTGATTACATC |
| | CCAGGCCGCCAGCTGCAGTTCTACGCTCAGTGCCGCCGCTG |
| | GTTATCTGCCGGGTTCCATCTCGACCCCCGCACCTTAGTTTT |
| | TGATGAGTCAGTGCCTTGTAGCTGCCGAACCACCATCCGGC |
| | GGATCGCTGGAAAATTTTGCTGTTTTATGAAGTGGCTCGGT |
| | CAGGAGTGTTCTTGTTTCCTCCAGCCCGCCGAGGGGCTGGC |
| | GGGCGACCAAGGTCATGACAATGAGGCCTATGAAGGCTCT |
| | GATGTTGATACTGCTGAGCCTGCCACCCTAGACATTACAGG |
| | CTCATACATCGTGGATGGTCGGTCTCTGCAAACTGTCTATC |
| | AAGCTCTCGACCTGCCAGCTGACCTGGTAGCTCGCGCAGCC |
| | CGACTGTCTGCTACAGTTACTGTTACTGAAACCTCTGGCCG |
| | TCTGGATTGCCAAACAATGATCGGCAATAAGACTTTTCTCA |
| | CTACCTTTGTTGATGGGGCACGCCTTGAGGTTAACGGGCCT |
| | GAGCAGCTTAACCTCTCTTTTGACAGCCAGCAGTGTAGTAT |
| | GGCAGCCGGCCCGTTTTGCCTCACCTATGCTGCCGTAGATG |
| | GCGGGCTGGAAGTTCATTTTTCCACCGCTGGCCTCGAGAGC |
| | CGTGTTGTTTTCCCCCCTGGTAATGCCCCGACTGCCCCGCC |
| | GAGTGAGGTCACCGCCTTCTGCTCAGCTCTTTATAGGCACA |
| | ACCGGCAGAGCCAGCGCCAGTCGGTTATTGGTAGTTTGTGG |
| | CTGCACCCTGAAGGTTTGCTCGGCCTGTTCCCGCCCTTTTCA |
| | CCCGGGCATGAGTGGCGGTCTGCTAACCCATTTTGCGGCGA |
| | GAGCACGCTCTACACCCGCACTTGGTCCACAATTACAGACA |
| | CACCCTTAACTGTCGGGCTAATTTCCGGTCATTTGGATGCT |
| | GCTCCCCACTCGGGGGGGCCACCTGCTACTGCCACAGGCCC |
| | TGCTGTAGGCTCGTCTGACTCTCCAGACCCTGACCCGCTAC |
| | CTGATGTTACAGATGGCTCACGCCCCTCTGGGGCCCGTCCG |
| | GCTGGCCCCAACCCGAATGGCGTTCCGCAGCGCCGCTTACT |
| | ACACACCTACCCTGACGGCGCTAAGATCTATGTCGGCTCCA |
| | TTTTcGAGTCTGAGTGCACCTGGCTTGTCAACGCATCTAAC |
| | GCCGGCCACCGCCCTGGTGGCGGGCTTTGTCATGCTTTTTT |
| | TCAGCGTTACCCTGATTCGTTTGACGCCACCAAGTTTGTGA |
| | TGCGTGATGGTCTTGCCGCGTATACCCTTACACCCCGGCCG |
| | ATCATTCATGCGGTGGCCCCGGACTATCGATTGGAACATAA |
| | CCCcAAGAGGCTCGAGGCTGCCTACCGCGAGACTTGCGCC |
| | CGCCGAGGCACTGCTGCCTATCCACTCTTAGGCGCTGGCAT |
| | TTACCAGGTGCCTGTTAGTTTGAGTTTTGATGCCTGGGAGC |
| | GGAACCACCGCCCGTTTGACGAGCTTTACCTAACAGAGCTG |
| | GCGGCTCGGTGGTTTGAATCCAACCGCCCCGGTCAGCCCAC |
| | GTTGAACATAACTGAGGATACCGCCCGTGCGGCCAACCTG |
| | GCCCTGGAGCTTGACTCCGGGAGTGAAGTAGGCCGCGCAT |
| | GTGCCGGGTGTAAAGTCGAGCCTGGCGTTGTGCGGTATCA |
| | GTTTACAGCCGGTGTGCCCGGCTCTGGCAAGTCAAAGTCCG |
| | TGCAACAGGCGGATGTGGATGTTGTTGTTGTGCCCACTCGC |
| | GAGCTTCGGAACGCTTGGCGGCGCCGGGGCTTTGCGGCATT |
| | CACTCCGCACACTGCGGCCCGTGTCACTAGCGGCCGTAGG |
| | GTTGTCATTGATGAGGCCCCTTCGCTCCCCCCACACTTGCT |
| | GCTTTTACATATGCAGCGTGCTGCATCTGTGCACCTCCTTG |
| | GGGACCCGAATCAGATCCCCGCCATAGATTTTGAGCACAC |

TABLE 2-continued

| Examples of ORF1 Nucleotide Sequences | |
|---|---|
| | CGGTCTGATTCCAGCAATACGGCCGGAGTTGGTCCCGACTT |
| | CATGGTGGCATGTCACCCACCGTTGCCCTGCAGATGTCTGT |
| | GAGTTAGTCCGTGGTGCTTACCCTAAAATCCAGACTACAAG |
| | TAAGGTGCTCCGTTCCCTTTTCTGGGGAGAGCCAGCTGTCG |
| | GCCAGAAGCTAGTGTTCACACAGGCTGCTAAGGCCGCGCA |
| | CCCCGGATCTATAACGGTCCATGAGGCCCAGGGTGCCACTT |
| | TTACCACTACAACTATAATTGCAACTGCAGATGCCCGTGGC |
| | CTCATACAGTCCTCCCGGGCTCACGCTATAGTTGCTCTCAC |
| | TAGGCATACTGAAAAATGTGTTATACTTGACTCTCCCGGCC |
| | TGTTGCGTGAGGTGGGTATCTCAGATGCCATTGTTAATAAT |
| | TTCTTCCTTTCGGGTGGCGAGGTTGGTCACCAGAGACCATC |
| | GGTCATTCCGCGAGGCAACCCTGACCGCAATGTTGACGTGC |
| | TTGCGGCGTTTCCACCTTCATGCCAAATAAGCGCCTTCCAT |
| | CAGCTTGCTGAGGAGCTGGGCCACCGGCCGGCGCCGGTGG |
| | CGGCTGTGCTACCTCCCTGCCCTGAGCTTGAGCAGGGCCTT |
| | CTCTATCTGCCACAGGAGCTAGCCTCCTGTGACAGTGTTGT |
| | GACATTTGAGCTAACTGACATTGTGCACTGCCGCATGGCGG |
| | CCCCTAGCCAAAGGAAAGCTGTTTTGTCCACGCTGGTAGGC |
| | CGGTATGGCAGACGCACAAGGCTTTATGATGCGGGTCACA |
| | CCGATGTCCGCGCCTCCCTTGCGCGCTTTATTCCCACTCTCG |
| | GGCGGGTTACTGCCACCACCTGTGAACTCTTTGAGCTTGTA |
| | GAGGCGATGGTGGAGAAGGGCCAAGACGGTTCAGCCGTCC |
| | TCGAGTTGGATTTGTGCAGCCGAGATGTCTCCCGCATAACC |
| | TTTTTCCAGAAGGATTGTAACAAGTTCACGACCGGCGAGAC |
| | AATTGCGCATGGCAAAGTCGGTCAGGGTATCTTCCGCTGGA |
| | GTAAGACGTTTTGTGCCCTGTTTGGCCCCTGGTTCCGTGCG |
| | ATTGAGAAGGCTATTCTATCCCTTTTACCACAAGCTGTGTT |
| | CTACGGGGATGCTTATGACGACTCAGTATTCTCTGCTGCCG |
| | TGGCTGGCGCCAGCCATGCCATGGTGTTTGAAAATGATTTT |
| | TCTGAGTTTGACTCGACTCAGAATAACTTTTCCCTAGGTCTT |
| | GAGTGCGCCATTATGGAAGAGTGTGGTATGCCCCAGTGGC |
| | TTGTCAGGTTGTACCATGCCGTCCGGTCGGCGTGGATCCTG |
| | CAGGCCCCAAAAGAGTCTTTGAGAGGGTTCTGGAAGAAGC |
| | ATTCTGGTGAGCCGGGCAGCTTGCTCTGGAATACGGTGTGG |
| | AACATGGCAATCATTGCCCATTGCTATGAGTTCCGGGACCT |
| | CCAGGTTGCCGCCTTCAAGGGCGACGACTCGGTCGTCCTCT |
| | GTAGTGAATACCGCCAGAGCCCAGGCGCCGGTTCGCTTAT |
| | AGCAGGCTGTGGTTTGAAGTTGAAGGCTGACTTCCGGCCG |
| | ATTGGGCTGTATGCCGGGGTTGTCGTCGCCCCGGGGCTCGG |
| | GGCCCTACCCGATGTCGTTCGATTCGCCGGACGGCTTTCGG |
| | AGAAGAACTGGGGGCCTGATCCGGAGCGGGCAGAGCAGCT |
| | CCGCCTCGCCGTGCAGGATTTCCTCCGTAGGTTAACGAATG |
| | TGGCCCAGATTTGTGTTGAGGTGGTGTCTAGAGTTTACGGG |
| | GTTTCCCCGGGTCTGGTTCATAACCTGATAGGCATGCTCCA |
| | GACTATTGGTGATGGTAAGGCGCATTTTACAGAGTCTGTTA |
| | AGCCTATACTTGACCTTACACACTCAATTATGCACCGGTCT |
| | GAATGA (SEQ ID NO: 6) |
| Genotype 3 | ATGGAGGCCCACCAGTTCATTAAGGCTCCTGGCATTACTAC |
| JQ679013.1 | TGCCATTGAGCAGGCTGCTCTGGCTGCGGCCAATTCCGCCT |
| | TGGCGAATGCTGTGGTGGTTCGGCCGTTTTTATCCCGTCTA |
| | CAAACTGAGATTCTTATCAATTTGATGCAACCCCGGCAGTT |
| | GGTTTTCCGCCCTGAAGTGCTTTGGAATCATCCTATCCAGC |
| | GGGTCATACACAATGAACTAGAACAGTACTGCCGGGCCCG |
| | TGCTGGCCGCTGTTTGGAGGTCGGAGCCCATCCGAGATCTA |
| | TTAATGATAACCCCAACGTCTTGCACCGGTGCTTCCTTAGA |
| | CCGGTTGGCAGGGATGTTCAGCGCTGGTACTCTGCCCCCAC |
| | CCGTGGCCCTGCGGCCAATTGCCGCCGCTCCGCGCTGCGTG |
| | GCCTTCCCCCCGTTGACCGCACCTACTGTTTTGATGGATTCT |
| | CCCGCTGTGCTTTTGCTGCAGAGACCGGTGTGGCCCTTTAC |
| | TCTTTGCATGACCTTTGGCCAGCTGATGTTGCAGAGGCGAT |
| | GGCCCGTCATGGGATGACACGGTTGTATGCCGCACTACATC |
| | TTCCTCCTGAGGTGCTGCTACCACCCGGCACCTATCACACA |
| | ACTTCGTATCTCCTGATTCACGACGGCGATCGCGCCGTTGT |
| | AACCTATGAGGGCGATACCAGTGCGGGCTATAACCATGAT |
| | GTTTCGATACTTCGTGCGTGGATCCGTACTACTAAAATAGT |
| | TGGTGACCACCCGTTGGTTATAGAGCGTGTGCGGGCCATTG |
| | GTTGTCATTTCGTGCTGTTGCTCACCGCGGCCCCTGAGCCG |
| | TCACCTATGCCTTATGTCCCCTACCCTCGTTCAACGGAGGT |
| | GTATGTTCGGTCTATATTTGGCCCTGGCGGCTCTCCATCTTT |
| | GTTTCCGTCAGCCTGCTCTACTAAATCTACCTTCCACGCTGT |
| | CCCGGTCCATATCTGGGATCGGCTCATGCTCTTTGGTGCCA |
| | CCCTGGATGATCAGGCGTTCTGTTGTTCACGACTCATGACT |
| | TACCTCCGTGGTATTAGCTACAAGGTCACTGTTGGTGCGCT |
| | TGTTGCTAATGAGGGGTGGAACGCCTCTGAAGATGCTCTTA |
| | CTGCAGTGATCACTGCGGCTTATCTGACTATCTGCCATCAG |
| | CGCTACCTCCGTACCCAGGCGATATCCAAGGGCATGCGCC |
| | GGTTGGAGGTTGAGCATGCCCAGAAATTTATCACAAGACT |

TABLE 2-continued

| Examples of ORF1 Nucleotide Sequences |
| --- |
| CTACAGTTGGCTATTTGAGAAGTCTGGCCGTGATTACATCC<br>CCGGCCGCCAGCTCCAGTTTTATGCACAGTGCCGACGGTGG<br>CTATCTGCAGGATTCCATCTGGACCCCAGGGTGCTTGTTTT<br>TGATGAATCAGTGCCATGTCGTTGTAGGACGTTCCTGAAGA<br>AAGTCGCGGGTAAATTCTGCTGTTTTATGCGGTGGTTAGGG<br>CAGGAGTGCACCTGCTTCCTGGAGCCAGCCGAGGGTTTAGT<br>TGGCGACCATGGCCATGACAATGAGGCTTATGAAGGTTCT<br>GAGGTCGACCAGGCTGAACCTGCCCATCTTGATGTTTCGGG<br>GACTTATGCCGTCCACGGGCACCAGCTTGTAGCCCTCTATA<br>GGGCACTTAATGTCCCACATGATATTGCCGCTCGAGCTTCC<br>CGATTAACGGCTACTGTTGAGCTTGTTGCAGGTCCAGACCG<br>CTTGGAGTGCCGCACTGTGCTCGGTAATAAGACCTTCCGGA<br>CGACGGTGGTTGATGGCGCCCATCTTGAAGCGAATGGCCC<br>AGAGCAGTATGTCCTGTCATTTGACGCCTCCTGTCAGTCTA<br>TGGGGGCCGGGTCGCACAACCTCACTTATGAGCTCACCCCT<br>GCCGGTTTGCAGGTTAGGATCTCATCTAACGGTCTGGATTG<br>CACTGCTACATTCCCCCCCGGCGGTGCCCCTAGCGCCGCGC<br>CAGGGGAGGTGGCAGCCTTCTGTGCTGCCCTTTACAGATAT<br>AACAGGTTCACCCAGCGGCACTCGCTGACCGGTGGACTAT<br>GGTTACACCCTGAGGGATTGCTGGGTATCTTCCCTCCATTC<br>TCCCCTGGGCATATCTGGGAGTCTGCTAACCCCTTTTGCGG<br>GGAGGGGACTTTGTATACCCGGACCTGGTCAACATCTGGCT<br>TTTCTAGTGATTTCTCTCCCCCTGAGGCGGCCGCCCCTGCTT<br>CGGCTGCTGCCCCGGGGCTGCCCCACCCTACCCCGCCTGCT<br>AGTGATATTTGGGCGTTACCACCGCCCTCCGAGGAGTGCTA<br>CACGCGCCTGGGCAACGACTTCCACACGAACAAGCGCGTG<br>TGCGAGGAGATCGCCATTATCCCTAGCAAAAAGCCCCGCA<br>ACAAGATGGCAGGTTATGTCACGCATCTGATGAAGCGAAT<br>TCAGAGAGGCCCAGTAAGAGGTATGTGCATCAAGCTGCAG<br>GAGGAGGCTCAGGTCGATGCAGCATCTGTGCCCCTTACCCT<br>CGTGCCTGCTGGGTCGCCCAGCCCTGTTGTGTCACCTTCCC<br>CACCACCACCTCCACCCGTGCGTAAGCCATCAACACCCCCG<br>CCTTCTCGTACCCGTCGCCTCCTCTACACCTACCCCGACGG<br>CGCTAAGGTGTATGCAGGGTCATTGTTTGAATCAGACTGTG<br>ATTGGCTGGTTAACGCCTCAAACCCGGGCCATCGCCCTGGA<br>GGTGGCCTCTGTCACGCCTTTCATCAACGTTTTCCGGAGGC<br>GTTTTATCCGACTGAATTCATTATGCGTGAGGGCCTAGCGG<br>CATACACCCTGACCCCGCGCCCTATCATCCACGCAGTGGCG<br>CCCGACTACAGGGTTGAGCAGAACCCGAAGAGGCTCGAGG<br>CAGCGTACCGGGAAACTTGCTCCCGTCGTGGCACCGCTGCT<br>TACCCGCTTTTAGGCTCGGGCATATACCAGGTCCCTGTCAG<br>CCTCAGTTTTGATGCCTGGGAACGCAATCATCGCCCCGGCG<br>ATGAGCTTTACTTGACTGAGCCCGCTGCGGCTTGGTTTGAG<br>GCTAATAAGCCGGCGCAGCCGGCGCTTACCATAACTGAGG<br>ATACGGCTCGTACGGCCAGCCTGGCATTAGAGATCGACGC<br>CGCTACAGAGGTTGGCCGTGCTTGTGCCGGCTGCACTATCA<br>GTCCTGGGATTGTGCACTATCAGTTTACCGCTGGGGTCCCG<br>GGCTCGGGCAAGTCAAGGTCCATACAACAGGGAGATGTTG<br>ATGTGGTGGTTGTGCCCACCCGGGAGCTCCGTAACAGTTGG<br>CGCCGCCGGGGTTTCGCGGCTTTCACACCTCACACAGCGGC<br>CCGTGTTACTAACGGCCGCCGCGTTGTGATTGATGAGGCCC<br>CATCTCTCCCGCCACACCTGTTGCTGCTACATATGCAGCGG<br>GCCTCCTCGGTTCACCTACTCGGTGACCCAAATCAGATCCC<br>TGCTATCGATTTTGAACACGCCGGCCTGGTCCCCGCGATCC<br>GCCCCGAGCTTGCACCAACGAGCTGGTGGCACGTCACACA<br>CCGTTGCCCGGCCGATGTGTGCGAACTCATACGCGGGGCCT<br>ACCCCAAAATCCAGACCACGAGCCGTGTGCTACGGTCCCT<br>GTTTTGGAATGAACCGGCTATCGGCCAGAAGTTGGTTTTTA<br>CGCAGGCTGCCAAGGCCGCTAACCCTGGTGCGATTACGGTT<br>CACGAAGCTCAGGGTGCCACCTTCACTGAGACCACAGTTAT<br>AGCCACGGCCGACGCCAGGGGCCTCATTCAGTCATCCCGG<br>GCCCATGCTATAGTTGCACTTACCCGCCACACCGAGAAGTG<br>CGTCATTTTGGATGCTCCCGGCCTGCTGCGTGAAGTCGGTA<br>TCTCGGATGTGATTGTCAATAATTTTTTCCTTGCAGGCGGA<br>GAGGTCGGCCATCACCGCCCTTCTGTGATACCCCGCGGTAA<br>CCCCGATCAGAACCTCGGGACTTTACAAGCCTTCCCGCCGT<br>CCTGCCAGATTAGTGCTTACCACCAGCTGGCTGAGGAATTA<br>GGCCATCGCCCTGCCCCTGTTGCCGCCGTCTTGCCCCCTTG<br>CCCCGAGCTTGAGCAGGGCCTGCTTTACATGCCACAAGAG<br>CTTACCGTGTCTGATAGTGTGCTGGTTTTTGAGCTCACGGA<br>CATAGTCCACTGCCGCATGGCCGCTCCAAGCCAGCGAAAG<br>GCTGTTCTTTCAACACTTGTGGGGCGGTATGGCCGTAGGAC<br>GAAGTTATATGAGGCAGCACATTCAGATGTCCGTGAGTCCC<br>TAGCCAGGTTCATCCCCACTATCGGGCCCGTTCAGGCCACC<br>ACATGTGAGTTGTATGAGTTGGTTGAGGCCATGGTGGAGA<br>AGGGTCAGGACGGGTCAGCCGTCTTAGAGCTAGATCTCTG<br>CAATCGTGATGTCTCGCGCATCACATTTTTCCAAAAGGATT<br>GCAACAAGTTTACAACTGGTGAGACTATTGCCCATGGCAA |

TABLE 2-continued

| Examples of ORF1 Nucleotide Sequences | |
|---|---|
| | GGTTGGTCAGGGTATATCGGCCTGGAGCAAGACATTCTGC<br>GCTTTGTTTGGCCCGTGGTTCCGTGCCATTGAGAAAGAAAT<br>ACTGGCCCTGCTCCCGCCTAATGTCTTTTATGGCGATGCTT<br>ATGAGGAGTCAGTGCTTGCTGCCGCTGTGTCAGGGGCGGG<br>GTCATGCATGGTATTTGAAAATGACTTTTCGGAGTTTGATA<br>GCACCCAGAACAACTTCTCTCTCGGCCTTGAGTGTGTGGTT<br>ATGGAGGAGTGCGGCATGCCTCAATGGTTAATTAGGTTGTA<br>TCACCTGGTACGGTCAGCCTGGATTCTGCAGGCGCCAAAG<br>GAGTCTCTTAAGGGTTTCTGGAAGAAGCATTCTGGTGAGCC<br>CGGTACCCTTCTTTGGAACACCGTTTGGAACATGGCAATCA<br>TAGCACATTGCTACGAGTTCCGTGACTTTCGTGTTGCTGCC<br>TTTAAGGGTGATGATTCGGTGGTCCTCTGTAGCGACTACCG<br>GCAGAGCCGCAATGCGGCAGCTTTGATTGCTGGCTGTGGG<br>CTTAAATTGAAGGTTGACTATCGCCCCATTGGGCTGTATGC<br>TGGGGTGGTGGTGGCCCCTGGCTTGGGGACACTGCCTGATG<br>TGGTGCGTTTTGCTGGTCGGCTGTCCGAAAAGAATTGGGGC<br>CCCGGCCCGGAACGTGCTGAGCAGCTACGTCTTGCTGTTTG<br>TGATTTCCTTCGAGGGTTGACGAACGTTGCGCAGGTCTGTG<br>TTGATGTTGTGTCCCGTGTCTATGGAGTTAGCCCCGGGCTG<br>GTACATAACCTTATTGGCATGTTGCAGACCATTGCCGATGG<br>CAAGGCCCACTTTACAGAGACTATTAAACCTGTTCTTGATC<br>TTACAAATTCCATCATACAGCGGGTAGAATGA (SEQ ID NO:<br>7) |
| Genotype 4<br>BAG32133.1 | ATGGAGGCCCATCAGTTCATAAAGGCTCCTGGCGTCACTAC<br>TGCTATCGAGCAGGCAGCTCTAGCAGCGGCCAACTCCGCC<br>CTGGCGAATGCTGTGGTGGTTCGGCCTTTCCTTTCCCGGCT<br>ACAGACAGAGATTTTGATAAACCTGATGCAGCCCCGGCAG<br>CTTGTCTTCCGACCTGAGGTTCTGTGGAATCACCCAATCCA<br>GCGCGTAATCCACAACGAGCTTGAGCAGTACTGTCGAGCC<br>CGTGCCGGTCGCTGCCTTGAGGTGGGAGCCCATCCGCGCTC<br>CATTAATGATAACCCCAATGTTTTGCACCGTTGCTTTTTGA<br>AACCCCGTGGTCGCGACGTTCAGCGGTGGTACACCGCCCCC<br>ACCCGCGGCCCTGCAGCGAATTGCCGCCGTTCGGCTCTTCG<br>TGGACTTCCACCTGTTGACCGGACATACTGTTTTGATGGTT<br>TTTCTGGATGTACGTTTGCTGCTGAGACTGGGGTTGCCCTTT<br>ATTCACTGCACGATCTGTGGCCTGCTGACGTCGCAGAGGCA<br>ATGGCCCGCCACGGTATGACTCGGCTGTATGCAGCCCTTCA<br>TCTCCCCCCGGAGGTGTTACTTCCTCCTGGCACCTATCATA<br>CCACATCATACCTTTTAATTCATGACGGCGATCGTGCTGTG<br>ATTACATATGAGGGTGACTCGAGCGCAGGGTACAATCATG<br>ATGTGTCTATTCTGCGCGCCTGGATCCGCACCACTAAAGTT<br>ACCGGCGACCACCCGTTGGTCATTGAGCGAGTCCGGGCGG<br>TAGGGTGTCACTTTGTGCTTTTGCTCACAGCCGCGCCTGAA<br>CCATCGCCGATGCCTTATGTCCCATACCCTCGCTCCACTGA<br>GGTCTATGTCCGGTCCATTTTTGGGCCAGGCGGCTCGCCCT<br>CTCTCTTCCCATCTGCCTGCTCGACTAAGTCTACATTTCATG<br>CCGTTCCTGTGCATATCTGGGACAGGCTCATGCTTTTTGGT<br>GCGACCCTTGATGACCAGGCTTTTTGCTGCTCGAGGCTTAT<br>GACGTACCTTCGTGGTATTAGTTATAAGGTTACAGTCGGTG<br>CTCTTGTTGCTAACGAAGGCTGGAACGCCTCCGAGGATGCA<br>CTGACTGCTGTAATTACTGCAGCATATCTCACCATTTGTCA<br>TCAGAGGTACCTCCGCACGCAGGCCATTTCGAAAGGAATG<br>AAGAGGTTGGAGCTTGAACATGCGCAGAAATTTATAACGC<br>GCCTTTATAGTTGGCTGTTCGAGAAGTCCGGCCGTGATTAC<br>ATCCCCGGCCGTCAGTTGCAGTTTTATGCCCAGTGCCGCCG<br>GTGGTTATCTGCAGGCTTTCATCTTGACCCACGTGTACTTGT<br>TTTTGATGAGGCAGCCCCCTGCCGTTGTCGTAATTTCCTTCG<br>GAAAGCCGCCCACAAGTTTTGTTGCTTCATGCGGTGGTTAG<br>GTCAGGATTGCACCTGTTTCCTCCAACCTATCGAGGGACGG<br>GTTGGCGAGCAGGGTTATGATAATGAAGCATTTGAAGGGT<br>CGGACGTCGACCCTGCTGAGGAGGCAACTGTGAGTATCTCT<br>GGGTCATATATTGTAACTGGTAGCCAGCTACAGCCTCTATA<br>TCAGGCGCTTGGTATCCCCTCTGATCTTGCTGCCCGTGCCG<br>GCCGGCTCACTGCCACTGTTGAAGTTTCTGATGCAAATGGC<br>CGCCTTACCTGCAAAACCATCATGGGCAATAAAACTTTCTC<br>AACAGTCTTCACTGATGGCGCCCAGCTGGAGGCCAACGGG<br>CCGGAGCAGTATGTGCTGTCATTCGACCCGATTAAACAAAC<br>TATGGCCGCCGGCCCGCATAATCTTAGTTATACCTTGACAT<br>CTGCAGGCCTTGAAATACATGTCGTCTCCGCCGGGCTTGAT<br>TGTAAGGCCGTCTTTCCGTCCGGGGTTGCGACCCCGTCTGC<br>CCCCGGGGAGGTGTCTGCCTTCTGTTCAGCATTGTACAGAT<br>TTAACCGCTGTGTCCAGCGGCACTCCCTCATTGGGGGTGTG<br>TGGTACCACCCTGAGGGGCTAGTCGGCCTGTTCCCGCCGTT<br>TTCCCCCGGCCATAGCTGGGAGTCTGCTAACCCCTTTTGCG<br>GGGAGAGTACCCTTTATACCCGTACCTGGTCGGTATCGGGA<br>TTTTCCAGCTGTTTTTCCCCACTTGAACCGGGGGCCCCGGA<br>CCCGCCCCCTCTTGTTGAGACTGACACGCCTACAGTTGTTG |

TABLE 2-continued

| Examples of ORF1 Nucleotide Sequences |
|---|
| ATACTCTGCCTCCAGTTGTTTCAGTACCCCTTGAGCAAATA<br>GTACTTCCACCAGACTCTGTAGATAAGGCAGCCGGCCCGA<br>CCGCATCTAGCGCCCCTGTTGTACCGCCAGCACCAGTGCAG<br>TCTGTAGTTCAACCATCTGGGCCTCGCCGGCGGCTGCTTCA<br>TACTTATCCTGATGGCTCGAAGGTGTATGCTGGCTCCCTTTT<br>TGAGTCCGACTGTACTTGGCTGGTTAACGCATCTAACCCTG<br>GCCACCGCCCTGGTGGCGGCCTCTGCCATGCGTTTTACCAA<br>CGGTTCCCAGAGTCATTTCATCCCGCTGAGTTTGTTATGTC<br>AGATGGGTTTGCAGCCTACACCCTGTCTCCCCGGCCCATTA<br>TTCATGCTGTTGCTCCTGACTATCGGGTTGAACATAACCCT<br>AAGAGGCTTGAGGCCGCCTATCGGGAGACGTGCTCTCGTCT<br>CGGGACTGCAGCTTACCCTTTACTTGGCGCCGGTATATATA<br>AGGTGCCTGTTGGGCTGAGCTTCGATGCCTGGGAACGTAAC<br>CACCGGCCCGGGGATGAGCTGTATCTGACTGAGCCAGCCG<br>TAGCTTGGTTTGAGGCAAACCGGCCTACTCTCCCAGCTCTT<br>ACCATCACTGAGGATACCGCGCGTACGGCGAACCTGGCAT<br>TGGAGCTAGACTCCGCCACTGAAGTCGGCCGGGCGTGTGC<br>TGGCTGCCGTGTAGAGCCCGGTGTCGTCCATTATCAGTTTA<br>CAGCAGGTGTCCCCGGATCAGGTAAATCCCGGTCAGTCCA<br>GCAGGGGGAGGTGGATGTGGTAGTGGTACCAACTCGTGAG<br>CTGCGCAATTCGTGGCGGCGCCGCGGGTTCGCAGCTTATAC<br>ACCCCACACCGCAGCTCGTGTCACCCGTGGTCGTAGGGTTG<br>TTATTGATGAGGCCCCGTCGCTCCCTCCACACTTGCTTTTGC<br>TGCATATGCAGCGGGCCTCCTCAGTCCATCTCTTAGGTGAT<br>CCTAATCAAATCCCTGCCATTGACTTTGAGCACGCCGGCCT<br>TGTTCCAGCTATTCGACCGGAGTTGGTCCCGACAAAATGGT<br>GGCACGTTACTCATAGATGCCCAGCCGATGTCTGTGAGTTA<br>ATTCGTGGTGCGTACCCAAAGATCCAGACTGTGAGCCGCGT<br>ACTCCGCTCTCTGTTCTGGGGGGAGCCCCCCGTGGGTCAGA<br>AGCTGGTGTTCACCCAGGCGGCGAAGGCCGCCAACCCTGG<br>TGCGATTACAGTCCACGAGGCCCAGGGTGCCACATTCACTG<br>AGACTACAATTATCGCCACGGCGGACGCCCGTGGGCTGAT<br>TCAGTCCTCCAGGGCCCATGCGATTGTGGCTCTGACCCGCC<br>ACACAGAGAAATGTGTGGTCGTTGACGCCCCGGGCCTCCTC<br>CGCGAGGTTGGTATCTCTGACGCTATTGTTAATAATTTCTTC<br>CTTTCCGGCGGTCAGGTTGGTCAGCACCGCCCGTCAGTCAT<br>ACCACGCGGCACTATTGATTGTAATGTTGATACACTTGATG<br>CATTCCCGCCCTCCTGTCAGTTTAGTGCCTACCACCAGCTT<br>GCCGAGGAGCTTGGCCATCGACCGGCCCCGATTGCTGCTGT<br>CTTACCTCCCTGCCCGGAGCTTGAACAGGGCCTGCTTTATA<br>TGCCTCAGGAGCTCACTACATCGGACAGTGTGCTAACATTT<br>GAGCTTACAGATATAGTGCACTGCCGTATGGCGGCGCCTA<br>GTCAGCGCAAGGCAGTCCTGTCGACTCTTGTCGGTAGGTAT<br>GGCCGCCGTACGAAGCTGTATGAAGCTGCTCATGCAGATG<br>TTCGTGGGTCTCTGAATCATTTTATCCCCGAGCTCCGCCCTA<br>TCAGCGTCACTACCTGCGAGCTCTATGAGCTTGTAGAGGCC<br>ATGGTTGAGAAAGGCCAGGACGGCTCCGCGGTTCTGGAGC<br>TCGACTTGTGCAGCCGTGATGTCTCGCGAATAACATTTTTC<br>CAGAAAGACTGCAATAAGTTTACAACTGGCGAAACAATAG<br>CGCATGGCAAAGTTGGGCAGGGGATATCTGCATGGAGTAA<br>AACCTTTTGCGCCCTGTTTGGCCCCTGGTTCCGTGCTATTGA<br>GAAAGAGATTCTAGCTGTGCTTGCGCCTAACGTATTTTATG<br>GTGATGCATATGAGGACACAGTTTTGGCCGCTGCCGTCGCA<br>GGAGCCTCCGGCTGTAAGGTTTTTGAGAATGATTTTTCAGA<br>GTTTGATAGTACCCAAAATAATTTCTCGCTTGGGCTGGAGT<br>GTATAATTATGGAGGAGTGTGGCATGCCGCAGTGGATGAT<br>TCGCCTCTACCATCTCGTCCGCTCCGCCTGGGTCCTCCAGG<br>CCCCGAAGGAGTCCTTGCGGGGTTTTTGGAAGAAACACTCT<br>GGTGAACCCGGTACTCTGCTCTGGAACACTGTCTGGAATAT<br>GGCAGTTATAGCCCACTGTTATGAGTTCCGTGACCTAAAAG<br>TTGCGGCGTTTAAGGGGGATGATTCTGTTGTGCTCTGTAGC<br>GACTATCGGCAGAGCCGTGATGCAGCTGCCTTGATTGCGG<br>GCTGTGGGTTGAAGGTTAAGGTGGACTTTAGGCCTATTGGG<br>CTGTATGCTGGTGTTGTTGTGGCCCCAGGTTTAGGAACCCT<br>ACCTGATGTTGTTAGGTTTGCTGGGCGACTCTCAGAGAAAA<br>ACTGGGGGCCCGGTTTGGAGAGGGCAGAGCAGCTACGGCT<br>GGCTGTTTGTGACTTTCTGCGAAGGTTAACGAATGTGGCTC<br>AGGTTTGTGTGGATGTTGTCTCGCAAGTATATGGTGTTAGC<br>CCTGGCTTGGTACATAACCTGATTGGGATGCTCCAGACTAT<br>TGCTGATGGTAAGGCCCATTTTACCGAAACAGTTAAACCTG<br>TCCTTGATTTGACCAACTCCATCATATATCGGGTGGATTGA<br>(SEQ ID NO: 8) |

TABLE 3

| Examples of ORF2 Nucleotide Sequences | |
|---|---|
| Genotype 1<br>AAL50056.1 | ATGCGCCCTCGGCCTATTTTGCTGTTGCTCCTCATGTTTCTG<br>CCTATGCTGCCCGCGCCACCGCCCGGTCAGCCGTCTGGCCG<br>CCGTCGTGGGCGGCGCAGCGGCGGTTCCGGCGGTGGTTTCT<br>GGGGTGACCGGGTTGATTCTCAGCCCTTCGCAATCCCCTAT<br>ATTCATCCAACCAACCCCTTCGCCCCCGATGTCACCGCTGC<br>GGCCGGGGCTGGACCTCGTGTTCGCCAACCCGCCCGACCA<br>CTCGGCTCCGCTTGGCGTGACCAGGCCCAGCGCCCCGCCGC<br>TGCCTCACGTCGTAGACCTACCACAGCTGGGGCCGCGCCGC<br>TAACCGCGGTCGCTCCGGCCCATGACACCCCGCCAGTGCCT<br>GATGTTGACTCCGGCGGCGCCATCCTGCGCCGGCAGTATAA<br>CCTATCAACATCTCCCCTCACCTCTTCCGTGGCCACCGGCA<br>CAAATTTGGTTCTTTACGCCGCTCCTCTTAGCCCGCTTCTAC<br>CCCTCCAGGACGGCACCAATACTCATATAATGGCTACAGA<br>AGCTTCTAATTATGCCCAGTACCGGGTTGCTCGTGCCACAA<br>TTCGCTACCGCCCGCTGGTCCCCAACGCTGTTGGTGGCTAC<br>GCTATCTCCATTTCGTTCTGGCCACAGACCACCACCACCCC<br>GACGTCCGTTGACATGAATTCAATAACCTCGACGGATGTCC<br>GTATTTTAGTCCAGCCCGGCATAGCCTCCGAGCTTGTTATT<br>CCAAGTGAGCGCCTACACTATCGCAACCAAGGTTGGCGCT<br>CTGTTGAGACCTCCGGGGTGGCGGAGGAGGAGGCCACCTC<br>TGGTCTTGTCATGCTCTGCATACATGGCTCACCTGTAAATT<br>CTTATACTAATACACCCTATACCGGTGCCCTCGGGCTGTTG<br>GACTTTGCCCTCGAACTTGAGTTCCGCAACCTCACCCCCGG<br>TAATACCAATACGCGGGTCTCGCGTTACTCCAGCACTGCCC<br>GTCACCGCCTTCGTCGCGGTGCAGATGGGACTGCCGAGCTC<br>ACCACCACGGCTGCTACTCGCTTCATGAAGGACCTCTATTT<br>TACTAGTACTAATGGTGTTGGTGAGATCGGCCGCGGGATA<br>GCGCTTACCCTGTTTAACCTTGCTGACACCCTGCTTGGCGG<br>TCTACCGACAGAATTGATTTCGTCGGCTGGTGGCCAGCTGT<br>TCTACTCTCGCCCCGTCGTCTCAGCCAATGGCGAGCCGACT<br>GTTAAGCTGTATACATCTGTGGAGAATGCTCAGCAGGATA<br>AGGGTATTGCAATCCCGCATGACATCGACCTCGGGGAATC<br>CCGTGTAGTTATTCAGGATTATGACAACCAACATGAGCAG<br>GACCGACCGACACCTTCCCCAGCCCCATCGCGTCCTTTTTC<br>TGTCCTCCGAGCTAATGATGTGCTTTGGCTTTCTCTCACCGC<br>TGCCGAGTATGACCAGTCCACTTACGGCTCTTCGACCGGCC<br>CAGTCTATGTCTCTGACTCTGTGACCTTGGTTAATGTTGCG<br>ACCGGCGCGCAGGCCGTTGCCCGGTCACTCGACTGGACCA<br>AGGTCACACTTGATGGTCGCCCCCTTTCCACCATCCAGCAG<br>TATTCAAAGACCTTCTTTGTCCTGCCGCTCCGCGGTAAGCT<br>CTCCTTTTGGGAGGCAGGAACTACTAAAGCCGGGTACCCTT<br>ATAATTATAACACCACTGCTAGTGACCAACTGCTCGTTGAG<br>AATGCCGCTGGGCATCGGGTTGCTATTTCCACCTACACTAC<br>TAGCCTGGGTGCTGGCCCCGTCTCTATTTCCGCGGTTGCTG<br>TTTTAGCCCCCACTCTGTGCTAGCATTGCTTGAGGATACC<br>ATGGACTACCCTGCCCGCGCCCATACTTTCGATGACTTCTG<br>CCCGGAGTGCCGCCCCCTTGGCCTCCAGGGCTGTGCTTTTC<br>AGTCTACTGTCGCTGAGCTTCAGCGCCTTAAGATGAAGGTG<br>GGTAAAACTCGGGAGTTATAG (SEQ ID NO: 9) |
| Genotype 2<br>AAA45732.1 | ATGCGCCCTAGGCCTCTTTTGCTGTTGTTCCTCTTGTTTCTG<br>CCTATGTTGCCCGCGCCACCGACCGGTCAGCCGTCTGGCCG<br>CCGTCGTGGGCGGCGCAGCGGCGGTACCGGCGGTGGTTTC<br>TGGGGTGACCGGGTTGATTCTCAGCCCTTCGCAATCCCCTA<br>TATTCATCCAACCAACCCCTTTGCCCCAGACGTTGCCGCTG<br>CGTCCGGGTCTGGACCTCGCCTTCGCCAACCAGCCCGGCCA<br>CTTGGCTCCACTTGGCGAGATCAGGCCCAGCGCCCCTCCGC<br>TGCCTCCCGTCGCCGACCTGCCACAGCCGGGGCTGCGGCGC<br>TGACGGCTGTGGCGCCTGCCCATGACACCTCACCCGTCCCG<br>GACGTTGATTCTCGCGGTGCAATTCTACGCCGCCAGTATAA<br>TTTGTCTACTTCACCCCTGACATCCTCTGTGGCCTCTGGCAC<br>TAATTTAGTCCTGTATGCAGCCCCCCTTAATCCGCCTCTGCC<br>GCTGCAGGACGGTACTAATACTCACATTATGGCCACAGAG<br>GCCTCCAATTATGCACAGTACCGGGTTGCCCGCGCTACTAT<br>CCGTTACCGGCCCCTAGTGCCTAATGCAGTTGGAGGCTATG<br>CTATATCCATTTCTTTCTGGCCTCAAACAACCACAACCCCT<br>ACATCTGTTGACATGAATTCCATTACTTCCACTGATGTCAG<br>GATTCTTGTTCAACCTGGCATAGCATCTGAATTGGTCATCC<br>CAAGCGAGCGCCTTCACTACCGCAATCAAGGTTGGCGCTC<br>GGTTGAGACATCTGGTGTTGCTGAGGAGGAAGCCACCTCC<br>GGTCTTGTCATGTTATGCATACATGGCTCTCCAGTTAACTC<br>CTATACCAATACCCCTTATACCGGTGCCCTTGGCTTACTGG<br>ACTTTGCCTTAGAGCTTGAGTTTCGCAATCTCACCACCTGT<br>AACACCAATACACGTGTGTCCCGTTACTCCAGCACTGCTCG<br>TCACTCCGCCCGAGGGGCCGACGGGACTGCGGAGCTGACC<br>ACAACTGCAGCCACCAGGTTCATGAAAGATCTCCACTTTAC<br>CGGCCTTAATGGGGTAGGTGAAGTCGGCCGCGGGATAGCT<br>CTAACATTACTTAACCTTGCTGACACGCTCCTCGGCGGGCT |

TABLE 3-continued

| Examples of ORF2 Nucleotide Sequences | |
|---|---|
| | CCCGACAGAATTAATTTCGTCGGCTGGCGGGCAACTGTTTT |
| | ATTCCCGCCCGGTTGTCTCAGCCAATGGCGAGCCAACCGTG |
| | AAGCTCTATACATCAGTGGAGAATGCTCAGCAGGATAAGG |
| | GTGTTGCTATCCCCCACGATATCGATCTTGGTGATTCGCGT |
| | GTGGTCATTCAGGATTATGACAACCAGCATGAGCAGGATC |
| | GGCCCACCCCGTCGCCTGCGCCATCTCGGCCTTTTTCTGTTC |
| | TCCGAGGAAATGATGTACTTTGGCTGTCCCTCACTGCAGCC |
| | GAGTATGACCAGTCCACTTACGGGTCGTCAACTGGCCCGGT |
| | TTATATCTCGGACAGCGTGACTTTGGTGAATGTTGCGACTG |
| | GCGCGCAGGCCGTAGCCCGATCGCTTGACTGGTCCAAAGT |
| | CACCCTCGACGGGCGGCCCCTCCCGACTGTTGAGCAATATT |
| | CCAAGACATTCTTTGTGCTCCCCCTTCGTGGCAAGCTCTCCT |
| | TTTGGGAGGCCGGCACAACAAAAGCAGGTTATCCTTATAA |
| | TTATAATACTACTGCTAGTGACCAGATTCTGATTGAAAATG |
| | CTGCCGGCCATCGGGTCGCCATTTCAACCTATACCACCAGG |
| | CTTGGGGCCGGTCCGGTCGCCATTTCTGCGGCCGCGGTTTT |
| | GGCTCCACGCTCCGCCCTGGCTCTGCTGGAGGATACTTTTG |
| | ATTATCCGGGGCGGGCGCACACATTTGATGACTTCTGCCCT |
| | GAATGCCGCGCTTTAGGCCTCCAGGGTTGTGCTTTCCAGTC |
| | AACTGTCGCTGAGCTCCAGCGCCTTAAAGTTAAGGTGGGTA |
| | AAACTCGGGAGTTGTAG (SEQ ID NO: 10) |
| Genotype 3 | ATGTGCCCTAGGGTTGTTCTGCTGCTGTTCTTCGTGTTTCTG |
| AFD33684.1 | CCTATGCTGCCCGCGCCACCGGCCGGCCAGCCGTCTGGCCG |
| | TCGTCGTGGGCGGCGCAGCGGCGGTGCCGGCGGTGGTTTCT |
| | GGGGTGACAGGGTTGATTCTCAGCCCTTCGCCCTCCCCTAT |
| | ATTCATCCAACCAACCCCTTCGCCGCCGATATCGTTTCACA |
| | ATCCGGGGCTGGAACTCGCCCTCGGCAGCCGCCCCGCCCCC |
| | TTGGCTCCGCTTGGCGTGACCAGTCCCAGCGCCCCTCCGCT |
| | GCCCCCCGCCGTCGATCTGCCCCAGCTGGGGCTGCGCCGTT |
| | GACTGCTGTATCACCAGCCCCTGACACAGCCCCTGTACCTG |
| | ATGTTGATTCACGTGGTGCTATTCTGCGTCGGCAGTATAAT |
| | TTGTCCACGTCCCCGCTCACGTCATCTGTTGCTTCGGGTACC |
| | AATTTGGTTCTCTACGCTGCCCCGCTAAATCCCCTCTTGCCC |
| | CTCCAGGATGGCACCAACACCCATATCATGGCTACTGAGG |
| | CATCCAACTATGCTCAGTACCGGGTCGTTCGAGCTACGATC |
| | CGCTACCGCCCGCTGGTGCCGAATGCTGTTGGTGGTTATGC |
| | TATTTCTATTTCTTTTTGGCCTCAAACTACAACTACCCCTAC |
| | TTCTGTTGATATGAATTCTATTACTTCCACTGATGTTAGGAT |
| | TTTGGTCCAGCCCGGTATTGCCTCCGAGTTAGTCATCCCTA |
| | GTGAGCGCCTTCATTATCGCAATCAAGGCTGGCGCTCTGTT |
| | GAGACCACAGGTGTGGCTGAGGAGGAGGCTACCTCCGGTC |
| | TGGTAATGCTTTGCATTCATGGCTCTCCTGTTAACTCTTATA |
| | CTAATACACCTTACACTGGTGCGTTGGGGCTCCTTGATTTT |
| | GCACTAGAGCTTGAATTCAGGAATTTGACACCCGGGAACA |
| | CCAACACCCGTGTTTCCCGGTATACCAGCACAGCCCGTCAT |
| | CGGTTGCGTCGCGGTGCTGATGGGACCGCTGAGCTTACTAC |
| | CACAGCAGCCACACGATTTATGAAGGATCTGCATTTCACTG |
| | GCACTAATGGCGTTGGTGAGGTGGGTCGCGGTATCGCCCTG |
| | ACACTGTTCAATCTTGCTGATACGCTTCTAGGTGGTTTACC |
| | GACAGAATTGATTTCGTCGGCTGGGGGTCAGTTGTTCTACT |
| | CCCGCCCTGTTGTCTCGGCCAATGGCGAGCCGACAGTGAA |
| | GTTATACACATCTGTGGAGAATGCGCAGCAAGACAAGGGC |
| | ATTACCATCCCACACGATATAGATTTGGGTGACTCCCGTGT |
| | GGTTATTCAGGATTATGATAATCAGCACGAGCAAGACCGA |
| | CCCACGCCGTCACCTGCCCCCTCACGCCCTTTCTCAGTCCTT |
| | CGCGCTAACGATGTTTTGTGGCTCTCCCTCACTGCCGCTGA |
| | GTACGATCAGGCTACGTATGGGTCGTCTACCAACCCTATGT |
| | ATGTCTCTGATACAGTTACCTTTGTCAATGTGGCCACTGGT |
| | GCTCAGGCTGTTGCCCGCTCTCTTGATTGGTCTAAAGTTAC |
| | TTTGGATGGTCGCCCCCTTACTACCATTCAGCAGTATTCTA |
| | AGACATTTTATGTTCTCCCGCTCCGCGGGAAGCTGTCCTTTT |
| | GGGAGGCTGGCACAACTAGGGCCGGCTACCCATATAACTA |
| | TAACACCACTGCTAGTGATCAAATTCTGATTGAGAATGCGG |
| | CCGGCCATCGTGTCGCTATCTCCACCTACACTACCAGCCTG |
| | GGTGCCGGCCCTGCCTCGATCTCCGCGGTGGGTGTATTAGC |
| | CCCACACTCGGCCCTTGCTGTTCTTGAGGACACTGTTGATT |
| | ACCCTGCTCGTGCTCACACTTTTGATGATTTCTGCCCGGAG |
| | TGTCGTACCCTAGGTTTGCAGGGTTGTGCATTCCAGTCCAC |
| | TATTGCTGAGCTTCAGCGCCTTAAAACGGAGGTAGGCAAA |
| | ACCCGGGAGTCTTAA (SEQ ID NO: 11) |
| Genotype 4 | ATGTTCTTTTGCTCTTTGCATGGAGATGCCGCCATGCGCTCT |
| BAG32134.1 | CGGGCTCTTCTGTTTTTGCTCCTCGTGTTTTTGCCTATGCTG |
| | CCCGCGCCACCGGCCGGTCAGTCGTCTGGCCGTCGCCGCGG |
| | GCGGCGCAGCGGCGGTACCGGCGGTGGTTTCTGGGGTGAC |
| | CGGGTTGATTCTCAGCCCTTCGCCCTCCCCTATATTCATCCA |
| | ACCAATCCCTTCGCATCCGACATTCCAACCGCAACCGGGGC |

TABLE 3-continued

| Examples of ORF2 Nucleotide Sequences |
| --- |
| TGGAGCTGGCCCTCGGCAGCCAGCCCGTCCACTCGGCTCCG<br>CTTGGCGCGACCAATCCCAGCGCCCCGCCGCTCCTGCCCGT<br>CGCCGACCTGCCCCAGCTGGGGCTTCGCCGCTAACAGCTGT<br>TGCCCCAGCCCCCGACACTGCCCCGGTTCCCGACGTGGACT<br>CCCGTGGTGCTATATTGCGCCGCCAGTACAACTTGTCCACG<br>TCACCGCTTACGTCCACTATCGCTACTGGCACTAATCTTGT<br>GCTATATGCTGCCCCACTGAGCCCTCTGCTCCCTCTCCAGG<br>ATGGGACTAATACTCATATCATGGCCACTGAGGCCTCTAAC<br>TATGCTCAGTATCGCGTTGTCCGTGCCACTATTCGGTACCG<br>GCCTCTGGTGCCGAATGCGGTTGGCGGGTACGCCATATCCA<br>TCTCCTTTTGGCCTCAGACAACAACCACCCCGACCTCCGTC<br>GACATGAATTCCATCACCTCTACCGATGTCCGTATCCTCGT<br>TCAGCCTGGTATAGCCTCTGAGCTTGTGATCCCTAGTGAGC<br>GCCTGCATTATCGCAATCAGGGTTGGCGCTCGGTTGAGACT<br>TCTGGTGTTGCGGAGGAGGAGGCTACCTCTGGCCTTGTTAT<br>GCTCTGTATTCATGGATCTCCTGTAAATTCCTACACTAATA<br>CACCCTATACTGGTGCTCTCGGCTTGCTCGATTTTGCGCTTG<br>AGCTTGAATTTCGTAATTTGACACCTGGCAATACGAATACG<br>CGCGTCTCTCGTTATTCTAGTAGTGCGCGCCACAAGTTACG<br>CCGAGGGCCTGATGGCACTGCCGAGTTGACCACCACTGCT<br>GCTACACGTTTCATGAAAGATCTCCATTTTACCGGGACTAA<br>TGGTGTTGGTGAGGTTGGCCGTGGTATTGCGCTAACTCTGT<br>TTAATCTTGCTGATACGCTTCTCGGCGGGCTCCCGACAGAA<br>TTGATTTCGTCGGCCGGAGGCCAATTGTTTTACTCACGCCC<br>CGTCGTCTCAGCCAATGGCGAGCCGACAGTGAAACTCTAC<br>ACCTCAGTTGAGAATGCCCAGCAGGACAAGGGTATAGCCA<br>TTCCACATGATATTGACCTTGGTGAGTCCCGAGTTGTGATT<br>CAGGATTATGATAATCAACACGAGCAAGACCGCCCCACCC<br>CTTCCCCTGCCCCCTCACGTCCTTTCTCAGTTCTTCGTGCTA<br>ATGATGTGCTTTGGCTTTCATTGACGGCTGCTGAATACGAT<br>CAAACTACTTATGGTTCTTCCACTAATCCTATGTATGTTTCT<br>GACACTGTGACATTTGTTAATGTAGCGACCGGTGCCCAGGG<br>GGTTTCTCGTTCCCTGGACTGGTCTAAAGTCACCCTCGATG<br>GTCGGCCGCTTACAACAATTCAGCAGTATTCTAAGACCTTC<br>TTTGTCCTACCTCTTCGTGGTAAGCTCTCTTTCTGGGAGGCT<br>GGCACTACTAAAGCTGGCTACCCTTATAATTATAACACTAC<br>TGCCAGTGATCAGATCTTAATTGAAAATGCACCTGGTCACC<br>GAGTCTGTATTTCCACCTATACTACTAATCTTGGTTCCGGCC<br>CTGTCTCTATTTCTGCCGTTGGTGTCCTCGCACCCCATTCTG<br>TGCTGGCCGCTTTGGAGGATACCGTTGATTACCCTGCTCGT<br>GCTCATACTTTCGATGATTTCTGCCCTGAGTGCCGTGCGCT<br>CGGTCTCCAGGGCTGCGCTTTTCAATCGACTGTCGCTGAGC<br>TGCAGCGTCTTAAAATGAAGGTGGGTAAAACCCGGGAGTA<br>TTGA (SEQ ID NO: 12) |

In one embodiment, the present invention is suitable for identifying an agent that inhibits any one or more activities of HEV ORF3 protein (e.g., ion channel activity, multimerization activity, or viroporin activity), thereby reducing or preventing HEV egress from an infected cell and inhibiting HEV infectivity. In some embodiments, the agent can bind to one or more regions of the ORF3 protein. For example, the agent can bind to (or make contact with) the ORF3 protein at any one or more residues selected from the residues at positions 11-13, 29-40, 59-61, 71-73, 80-85, 86-89, or 95-98 of SEQ ID NO: 1. In certain embodiments, the agent can bind to one or more regions of an ORF3 protein comprising any one of SEQ ID NOs: 2-4, wherein the one or more regions correspond to (e.g., possess equivalent functions to) any one or more residues selected from the residues at positions 11-13, 29-40, 59-61, 71-73, 80-85, 86-89, or 95-98 of SEQ ID NO: 1.

In some embodiments, the agent is a small molecule, as described herein.

As described herein, in some embodiments, the method comprises introducing into a cell culture 1) a nucleic acid that comprises an HEV open reading frame 2 (ORF2) nucleotide sequence, 2) a nucleic acid that comprises an HEV ORF3 nucleotide sequence, and 3) a nucleic acid that i) comprises a reporter gene and an HEV ORF1 nucleotide sequence and ii) lacks HEV ORF2 and ORF3 nucleotide sequences. As described herein, various methods for introducing (e.g., transfecting, transducing, transforming) nucleic acids into cells of a cell culture are known in the art and can be used in the methods disclosed herein.

In some embodiments, the cell culture comprises, or is derived from, a hepatocyte. In certain embodiments, the cell culture comprises, or is derived from, a gastrointestinal cell. However, other suitable types of cells can also be used in the present transcomplementation system, as determined by those of skill in the art.

In some embodiments, the nucleic acids encoding ORF2 and ORF3 are introduced into the cells in the cell culture on a single vector. However, as will be apparent to those of skill in the art, ORF2 and ORF3 can be introduced into the cells in the cell culture on separate vectors. In various embodiments, the nucleic acid components introduced into the cells are introduced as an RNA molecule (e.g., in vitro-transcribed HEV RNA).

In certain embodiments, the nucleic acid that i) comprises ORF1 and a reporter gene and ii) lacks ORF2 and ORF3 is introduced as an RNA molecule (e.g., in vitro-transcribed HEV RNA). The nucleic acid can lack either all or a portion of the ORF2 and ORF3 sequences, provided no functional ORF2 and/or ORF3 proteins are expressed. In a particular embodiment, the nucleic acid lacks ORF2 and ORF3 nucleotide sequences entirely.

Any suitable reporter gene known in the art can be used in the present invention. In various embodiments, the reporter gene encodes, e.g., a fluorescent reporter, a bioluminescence reporter, a chemiluminescence reporter, or a selectable marker. An example of a bioluminescence reporter includes, e.g., a luciferase enzyme. Examples of selectable markers include, e.g., puromycin, blasticidin HSK-thymidine kinase, and the like.

In some embodiments, the method further comprises contacting the cell culture (i.e., the cells introduced with 1) a nucleic acid that comprises an HEV ORF2 nucleotide sequence, 2) a nucleic acid that comprises an HEV ORF3 nucleotide sequence, and 3) a nucleic acid that i) comprises a reporter gene and an HEV ORF1 nucleotide sequence and ii) lacks HEV ORF2 and ORF3 nucleotide sequences) with a candidate agent to be tested for anti-HEV activity (e.g., a reduction, completely or partially, in HEV function), as described herein. Generally, the candidate agent is contacted with the cell culture into which nucleic acid has been introduced by adding the candidate agent into the medium in which the cells are cultured. Methods of determining a suitable concentration range to be tested will depend on the agent to be tested, according to systematic methods typically used in the art.

In some embodiments, the method also comprises harvesting the cell culture media from the cell culture that has been contacted with the agent to collect the HEV released by the cells (e.g., transfected or transduced cells) into the cell culture media. In certain embodiments, it may be desirable to lyse the cells (e.g., transfected or transduced cells) to determine the proportion of HEV that did not properly release into the cell culture media.

In some embodiments, the method further comprises combining the harvested media (collected from the cell culture of the cells that have been, e.g., transduced or transfected) with a naïve cell culture to infect the naïve cell culture with the HEV released from the cells (e.g., transduced or transfected). The harvested media can be processed prior to combining (infecting) with the naïve cells to, e.g., filter or concentrate the collected HEV.

As used herein, a "naïve" cell culture refers to a cell culture comprised of cells that are not infected with HEV and/or have not been introduced with full-length or subgenomic variants (e.g., fragments) of the HEV genome. In certain embodiments, the naïve cells are of the same cell-type as the cells (e.g., transduced or transfected cells) from which the HEV has been obtained.

In some embodiments, the method further comprises measuring a level of activity of the reporter gene in the naïve cell culture. Methods of measuring the level of activity of reporter genes such as a fluorescent reporter, a bioluminescence reporter, a chemiluminescence reporter are readily available and well-known in the art. For example, as described herein, a luciferase assay can be performed to measure the level of activity of a luciferase gene, according to standard manufacturer's protocol.

In various embodiments, the method also comprises comparing the level of reporter activity measured in the naïve cell culture, also referred to herein as "the measured activity level," to a reference activity level, wherein a decrease in measured activity level as compared to the reference activity level indicates that the agent inhibits HEV infectivity. In some embodiments, the reference activity level is obtained from a naïve cell culture that has been infected with HEV particles harvested from cells that were not contacted with the agent to be tested for anti-HEV activity.

Alternatively, or in addition to measuring and comparing the level of reporter activity in the naïve cell culture to a reference level, the method comprises comparing the level of released HEV or component thereof (e.g., capsid protein) measured in the naïve cell culture to a reference level of released HEV or component thereof, wherein a decrease in measured HEV level as compared to the reference level indicates that the agent inhibits HEV infectivity. In some embodiments, the level of a released HEV can be measured by ELISA (e.g., by detecting the capsid protein with a capture antibody). In some embodiments, the reference level of released HEV is obtained from a naïve cell culture that has been infected with HEV particles harvested from cells that were not contacted with the agent to be tested for anti-HEV activity.

In certain embodiments, a decrease in measured activity level of at least 20%, at least 25%, at least 30%, at least 35%, at least 40%, at least 45%, at least 50%, at least 55%, at least 60%, at least 65%, at least 70%, at least 75%, at least 80%, at least 85%, at least 90%, at least 95, or 100% as compared to the reference level indicates that the agent inhibits HEV infectivity.

Unless defined otherwise, all technical and scientific terms used herein have the same meaning as commonly understood by one of ordinary skill in the art (e.g., in cell culture, molecular genetics, nucleic acid chemistry, hybridization techniques and biochemistry). Standard techniques are used for molecular, genetic and biochemical methods (see generally, Sambrook et al., Molecular Cloning: A Laboratory Manual, 2d ed. (1989) Cold Spring Harbor Laboratory Press, Cold Spring Harbor, N.Y. and Ausubel et al., Short Protocols in Molecular Biology (1999) 4th Ed, John Wiley & Sons, Inc. which are incorporated herein by reference) and chemical methods.

EXEMPLIFICATION

Materials and Methods

Cell Line and Animals

HEK293T cells (ATCC, Manassas, Va., USA) and HepG2C3A cells (ATCC) were maintained in Dulbecco's modified Eagle medium (DMEM) supplemented with 10% Fetal Bovine Serum (FBS) 50 IU/ml Penicillin and Streptomycin, in a humidified 5% CO2 incubator at 37° C. All experiments involving oocytes derived from *Xenopus laevis* were performed in accordance to protocols approved by the Institutional Animal Care and Use Committee at Rutgers University.

Plasmids Construction

To construct lentiviral construct that encoding Kernow C1/p6 ORF2 or Kernow C1/p6 ORF3, the Kernow C1/p6 ORF2 or Kernow C1/p6 ORF3 cDNA was amplified by PCR from HEV Kernow C1/p6 construct (a kind gift from Dr. Suzanne Emerson, NIH) and then cloned into pLVX-IRES-zsGreen1 or pLEX-IRIS-mCherry vectors using In-Fusion® HD Cloning Kit (Clontech, Mountain View, Calif., USA). To construct the pLEX-IAV M2-IRES-mCherry vector, cDNA encoding Influenza A virus M2 (A/Puerto Rico/8/34/Mount Sinai/Wi(H1N1)) was synthesized by IDT with gBlock, and then cloned into pLEX-IRES-mCherry vectors using In-Fusion® HID Cloning Kit (Clontech). IAV M2 mutants were generated by Quikchange (Stratagene) site-directed mutagenesis. All the constructs were verified by DNA sequencing analysis.

Generation of ORF3 alanine mutants. Kernow C1/p6 ORF3 alanine triplet mutants were synthesized by GenScript (Piscataway, N.J.) or by PCR amplification with primers containing the desired changes. Primary PCR products containing the engineered mutations were assembled and cloned into the pLEX-IRES-mCherry vector using In-Fusion® HD Cloning Kit (Clontech) in according to the instruction.

In Vitro Transcription (IVT) and Viral RNA Transfection

HEV Kernow-C1 p6/Gluc plasmid (genotype 3 subgenomic replicon expressing Gaussia luciferase; a gift from Dr. Suzanne Emerson, NIH) was linearized by MluI and the viral capped RNAs were transcribed in vitro from linearized plasmid using mMESSAGE mMACHINE® T7 Ultra Kit (Ambion, Austin Tex., USA). The IVT reaction mixture of 20 μl was assembled by adding DNA template (1 μg), T7 Reaction Buffer, T7 NTP/ARCA, GTP and T7 Enzyme Mix. The IVT reaction mixture was incubated at 37° C. for 3 hr. To remove the template DNA, 1 μl TURBO DNase (from MEGAscript® 17 Kit) was added to the IVT reaction mixture and incubated for 15 min at 37° C. Then, the viral RNA was purified using RNeasy Mini Kit (Qiagen, Hilden, Germany). Viral RNA was transfected into HepG2C3A cells using TransIT®-mRNA Transfection reagent (Minis Bio LLC, Madison, Wis., USA) in according to the instruction.

Gaussia Luciferase Assay

Gaussia luciferase activity was measured with the Renilla Luciferase Assay System (Promega, Madison, Wis., USA). Ten microlitres of harvested cell culture medium was added per well of a 96-well black, flat-bottom microplate (Corning, N.Y., USA), followed by the addition of Renilla luciferase assay substrate and the detection of luminescence using a Berthold luminometer.

Lentiviral Particles Production and Infection

VSV-G pseudotyped lentiviruses were produced by transient co-transfection of the 3rd generation packaging plasmids pMD2G, psPAX2 and transfer vector with X-tremeGENE™ HP DNA Transfection Reagent (Sigma-Aldrich, St. Louis, Mo., USA) into HEK293T cells. The media was changed 6 h post-transfection. Supernatants were collected at 48 and 72 hr after transfection, pooled, passed through a 0.45 μm filter and frozen at −80° C. For lentiviral transduction, $1\times10^5$ cells/well were seeded in 6 well tissue culture plates and infected the following day with lentiviruses. Cells were trypsinized and processed for FACS analysis after 3 days of infection to determine the transduction efficiency.

Co-Immunoprecipitation and Western Blot Assay

Cell lysates were prepared from $5\times10^6$ cells in a 10 mM Tris buffer (pH, 7.5) containing 0.1% NP-40 and 1 mM EDTA, along with a cocktail of protease and phosphatase inhibitors. Lysates were then incubated with Flag (M2, sigma) antibody (1 ug, at 4° C. for 6 hr), after which the immune-complexes were precipitated with protein A-sepharose. These immunoprecipitates were resolved on a 12% SDS-polyacrylamide gel, transferred onto a nitrocellulose membrane, and then analyzed by Western blot using anti-Flag (M2, Sigma) or anti-HA(Clone HA-7, Sigma) antibodies. Membranes were then washed three times with TBS-T for 15 min total. Membranes were incubated with goat anti-mouse DyLight800-conjugated antibody (Thermo Fisher Scientific) diluted 1:5000 for 30 min and washed with TBS-T three times for 5 min each. Membranes were visualized using the Odyssey® CLx Imaging System and images were processed using Image Studio Lite Ver5.0.

Cell Culture Derived HEV Generation and Infection

HEV Kemow C1/p6 viral RNA was generated with in vitro transcription kit and transfected into HepG2C3A cells as describe before. Medium was removed from transfected cells after 7 days post transfection and cells were trypsinized and centrifuged at 800 rpm for 5 min. PBS (1 ml) suspended the cell pellet and the sample was subjected to three rounds of freezing and thaw. Debris was removed by centrifugation at 13,200 rpm for 5 min and the supernatant was stocked at −80° C. As for the infection assay, the HepG2C3A cells were seeded into a 6-well plate, and cells were infected by HEV in the following day, medium was changed at 12 hs after the infection. After 6 days, cells were fixed and stained for immunofluorescence microscopy.

Confocal Microscopy

HepG2C3A cells were washed with PBS 3 days after lentiviral transduction with HA-tagged wild type or mutant ORF3 constructs, fixed with 4% paraformaldehyde (PFA) and then permeabilized with 0.3% Triton X-100. The cells were blocked with 2% bovine serum albumin (BSA) and immunolabeled with mouse anti-HA (Clone HA-7, Sigma) and rabbit anti-calnexin(Abcam, Cambridge, Mass., USA) antibodies for 1 h at room temperature. Cells were washed with phosphate-buffered saline (PBS) and incubated with Alexa Fluor 488-conjugated goat anti-mouse antibody (Thermo Fisher Scientific) or Alexa Fluor 647-conjugated goat anti-rabbit antibody (Thermo Fisher Scientific) for 1 h. Nuclei were stained with Hoechst dye. To observe the localization of ORF3 in the *Xenopus laevis* oocytes, the oocytes were collected at 48 hrs after ORF3 mRNA injection for immunostaining assay as described above, rabbit anti-ORF3 polyclonal antibody (a kind gift from Dr. Suzanne Emerson, NIH) and Alexa Fluor 555-conjugated goat anti-rabbit antibody (Thermo Fisher Scientific) were used. Images were taken using a Nikon A1 Spectral Confocal Microscope. ImageJ analysis was done using ImageJ software (National Institutes of Health).

Voltage Clamp Experiments

The ORF3 or M2 cDNA was cloned into pSP64-polyA vector with restriction sites for HindIII (5' end) and BamHI (3' end) enzymes. The plasmid was linearized by EcoRI digestion and transcribed in vitro to synthesized mRNA using the mMESSAGE mMACHINE high-yield capped RNA transcription SP6 kit (Ambion, USA). Healthy *Xenopus laevis* oocytes in stage V to VI were injected with 20 ng of mRNA per oocyte and incubated at 16° C. in an ND-96 solution. Two-electrode voltage clamp (OC-725C, Warner Instrument Corp.) was used to record the currents at 48 hr post of injection. The oocytes were first bathed in standard Ringer solution (115 mM NaCl, 2 mM KCl, 1.8 mM CaCl2 and 5 mM HEPS, pH7.4) at room temperature and impaled with microelectrodes filled with 3 M KCl. Currents were generated by applying the rectangular voltage protocol from −90 to +60 mV in 10 mV increments with a holding voltage of −60 mV. Current recording and analysis were performed by pClamp 10.3 software package (Axon Instruments).

Flow Cytometric Analysis

Expression of lentivirally-delivered transgenes was analyzed by flow cytometry. Kernow C1/p6 ORF2 or ORF3 (IAV M2 or its mutant) were transduced into target cells by bicistronic lentiviruses expressing zsGreen or mCherry. After 3 days transduction, cells were fixed in PEA 4%/PBS for 15 min, then washed with PBS. The efficiencies of transduction of Kenow C1/p6 ORF2 and ORF3 (IAV M2 or its mutant) were determined by simultaneous expression zsGreen and mCherry. All samples were analyzed on a BD LSRII flow cytometer using FlowJo Software (FlowJo, LLC, Ashland, Oreg., USA).

Quantification of Intracellular Virus infectivity

The Kernow C1/p6-ΔORF2/3[Gluc] RNA transfected HepG2C3A cells were cultured in the 12-well cell culture plate and cells were trypnized and washed with PBS, and then lysed by adding 1 ml H2O per well and put on the ice for 20 min, vortexing intermittently every 5 min. The samples were centrifuged at 13,000×g for 10 min to remove cellular debris, and 0.9 ml of the supernatant was collected and 0.1 ml of 10× concentrated PBS was added to infect cells.

Statistical Analysis

Student's t test was used to test for statistical significance of the differences between the different group parameters p values of less than 0.05 were considered statistically significant.

Results

Characterization of ORF3 as a Pore-Forming Protein

Figure 1B:
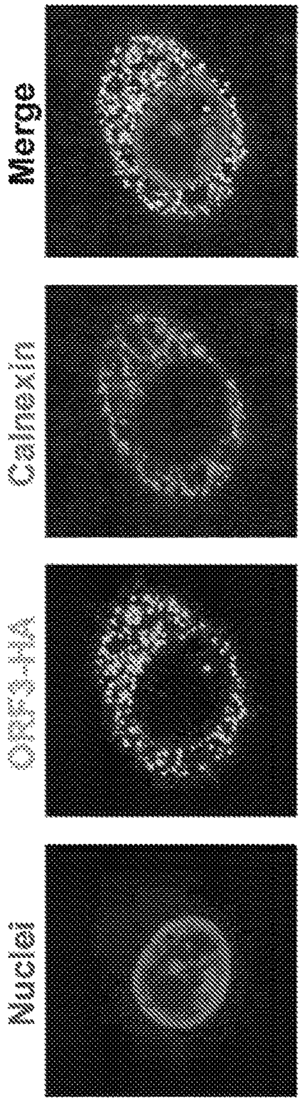
Figure 1C:
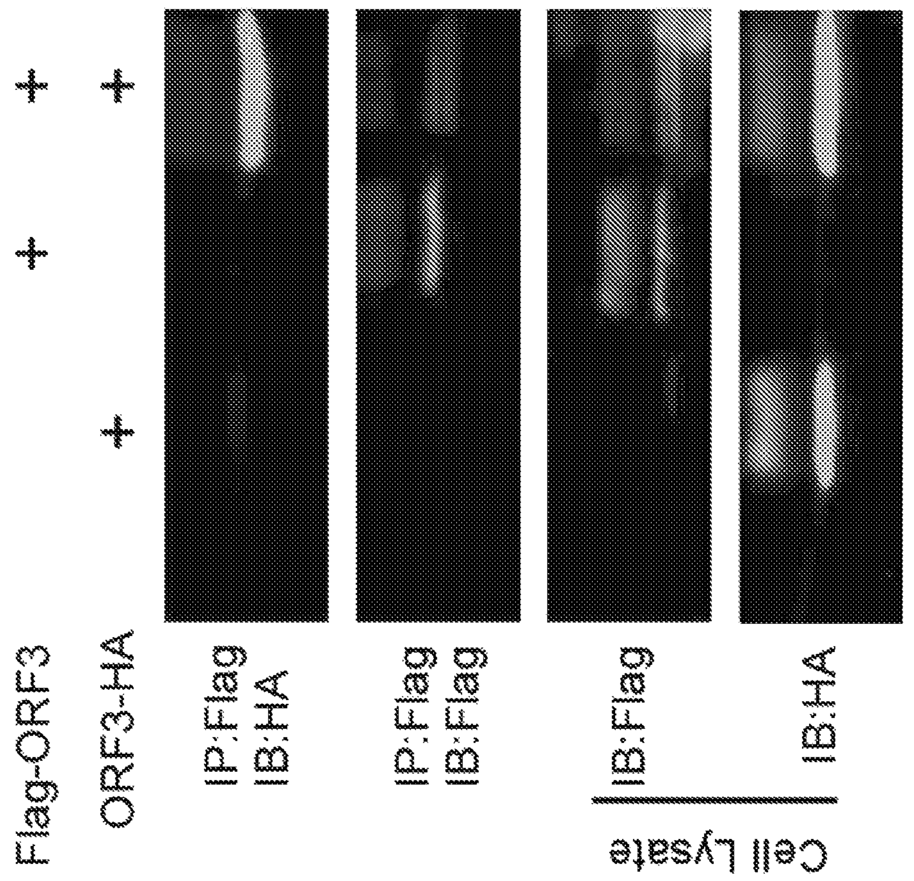
Figure 1D:
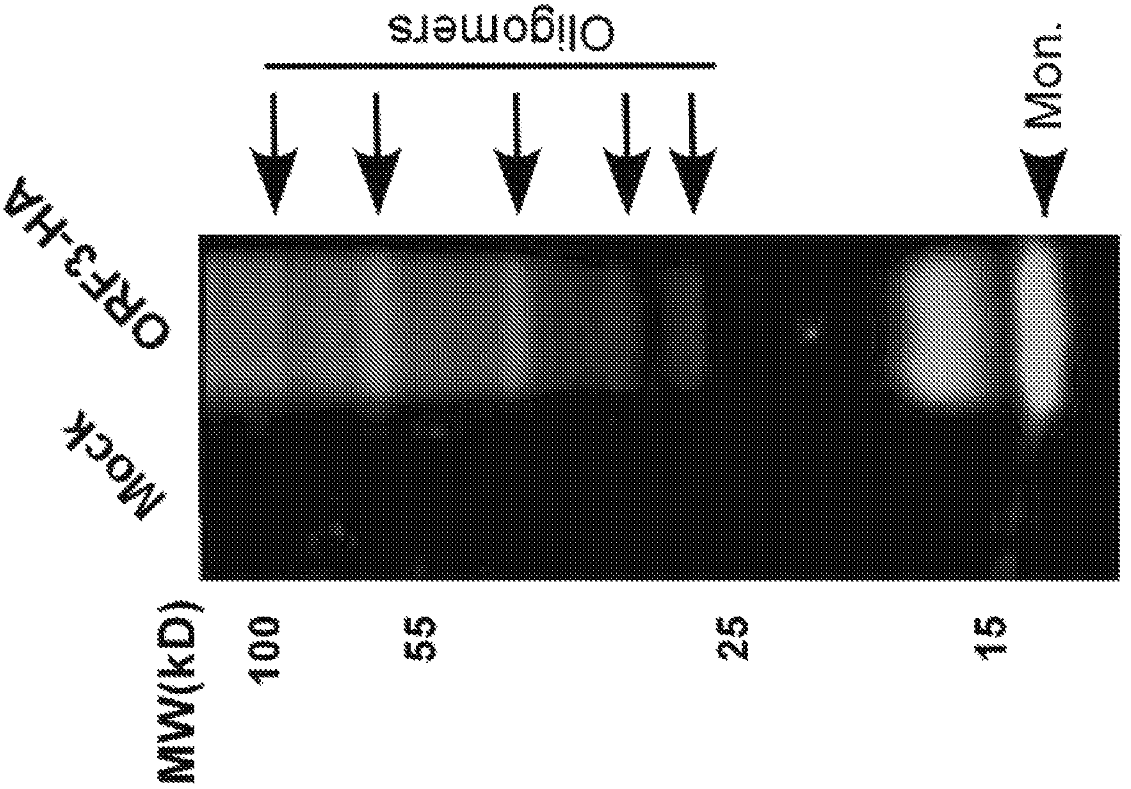

Bioinformatic analysis indicated that HEV ORF3 contained a putative transmembrane domain (FIG. 1A). This prediction was corroborated following expression of HEV ORF3 in HepG2C3A cells, a commonly used human hepatoma cell line permissive to HEV infection. In these cells, colocalization of ORF3 with the ER-associated protein calnexin was observed (FIG. 1B), suggesting ORF3 associates with intracellular membranes likely derived from the ER. Based on the punctate pattern in which ORF3 was expressed, it was determined whether the protein forms larger complexes. FLAG-tagged ORF3 immunoprecipitated with an anti-HA antibody in lysates derived from HepG2C3A cells co-expressing FLAG- and HA-tagged ORF3 (FIG. 1C). Additionally, larger protein complexes were observed in Western blots of HepG2C3A lysates even under denaturing conditions, suggesting multimerization (FIG. 1D). Collectively, these data confirm that HEN ORF3 is a transmembrane protein localized at ER membranes (Tyagi, S., et al. *J Biol Chem* 279, 29308-29319 (2004)) and forms multimedia complexes, likely through homophilic interactions.

Figure 2A:
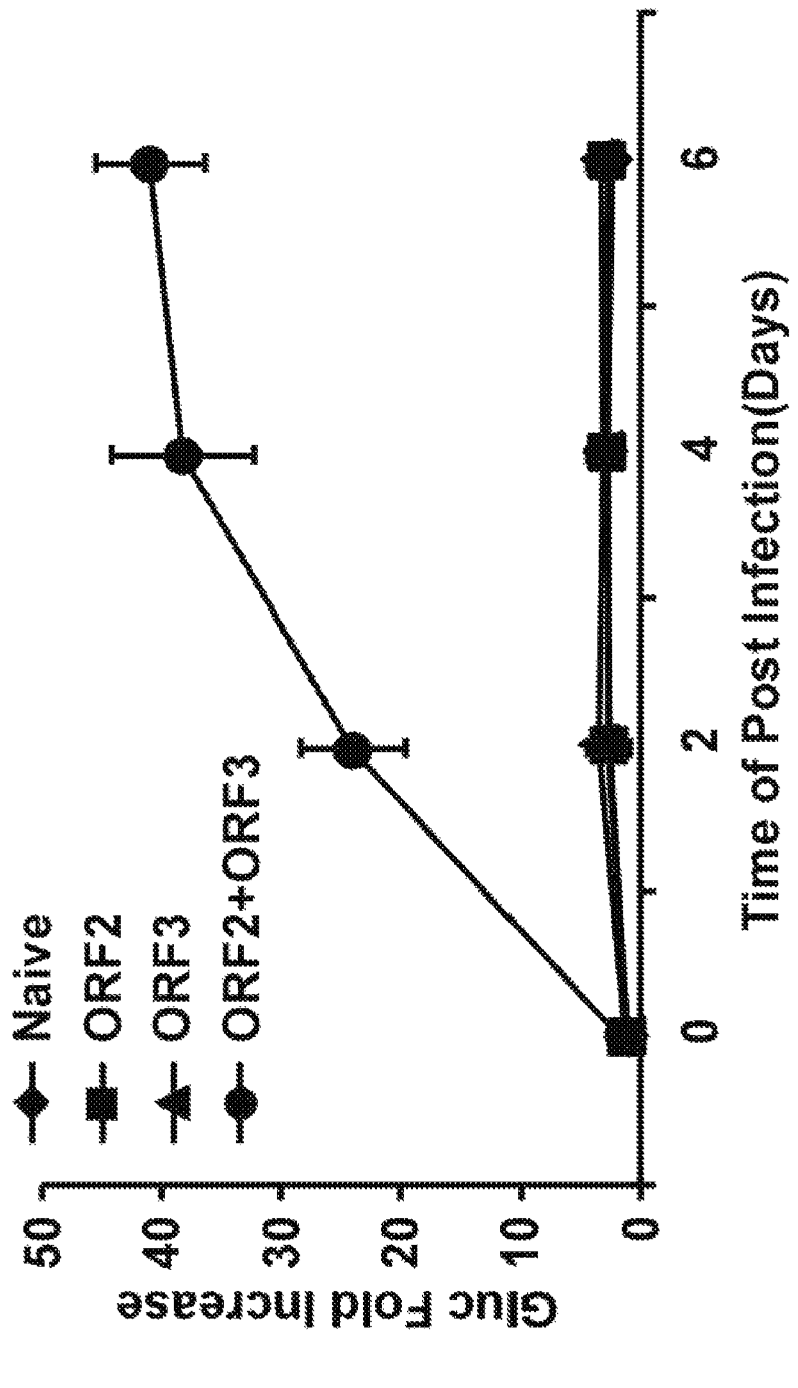
FIGS. 2A and 2B show that ORF2 and ORF3 are required for releasing viral particles to infect naïve HepG2C3A cells.
Figure 2B:
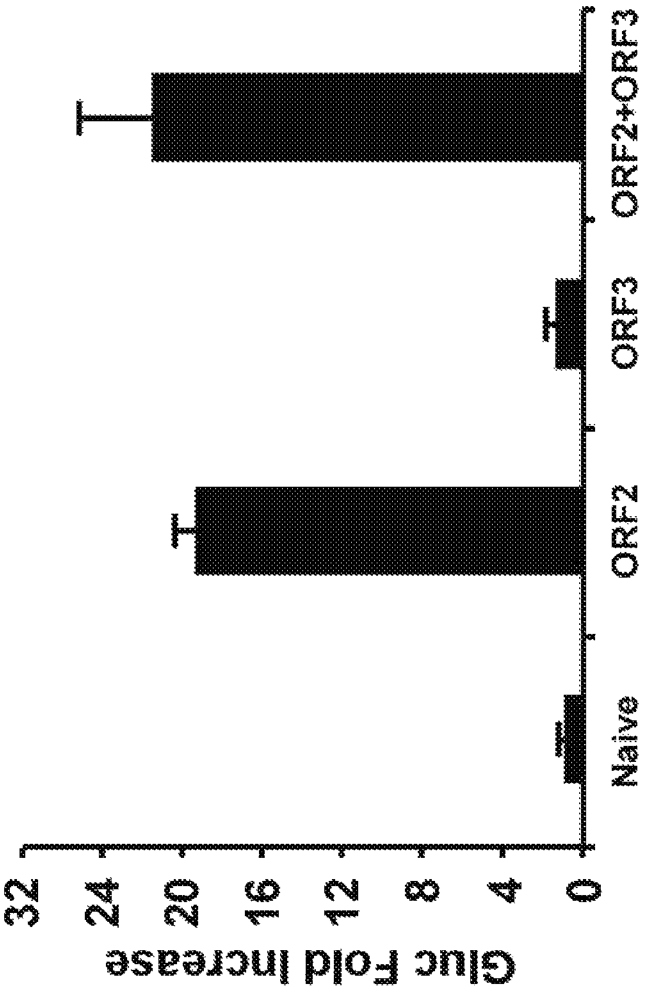
Figure 5A:
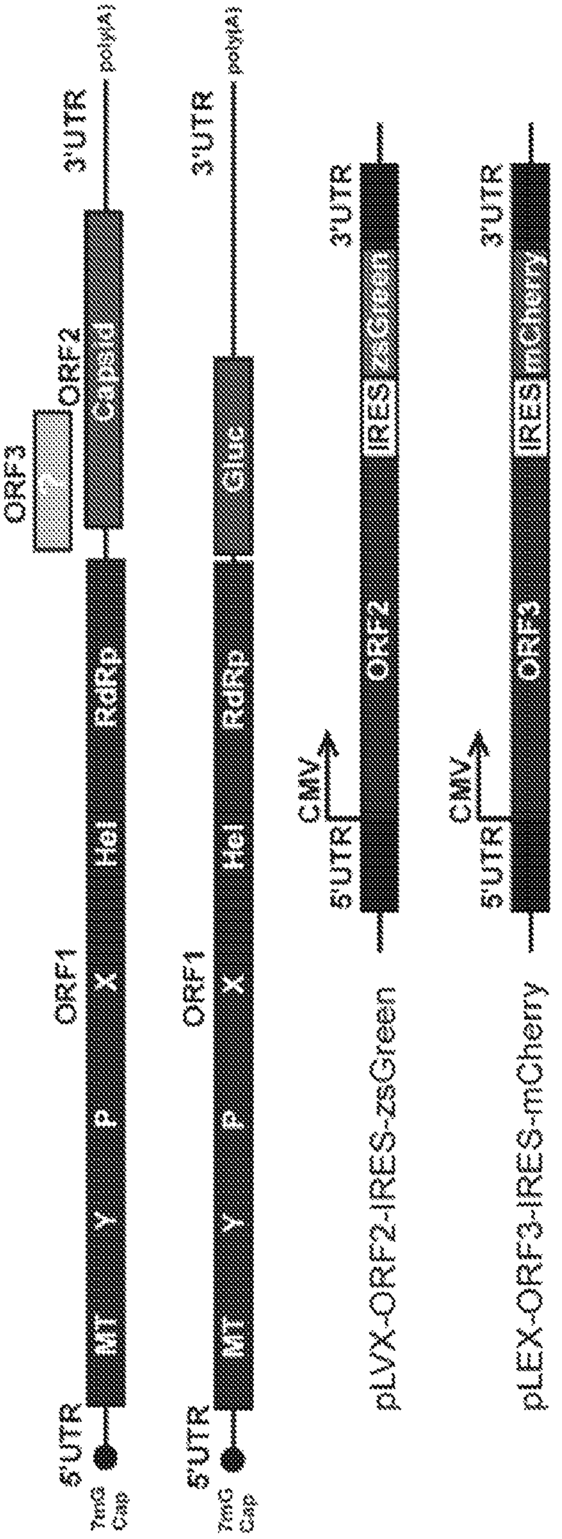
FIGS. 5A-5C relate to the transcomplementation system.
Figure 5B:
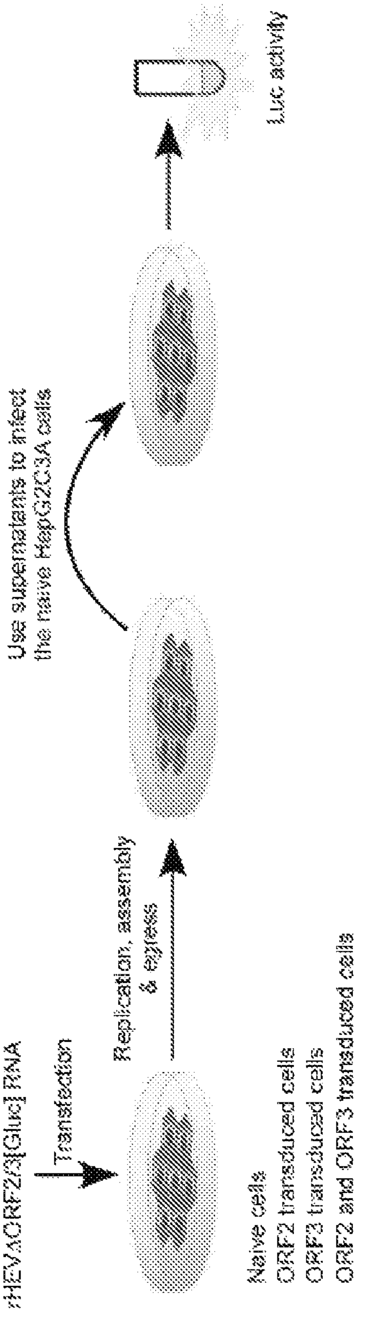
Figure 5C:
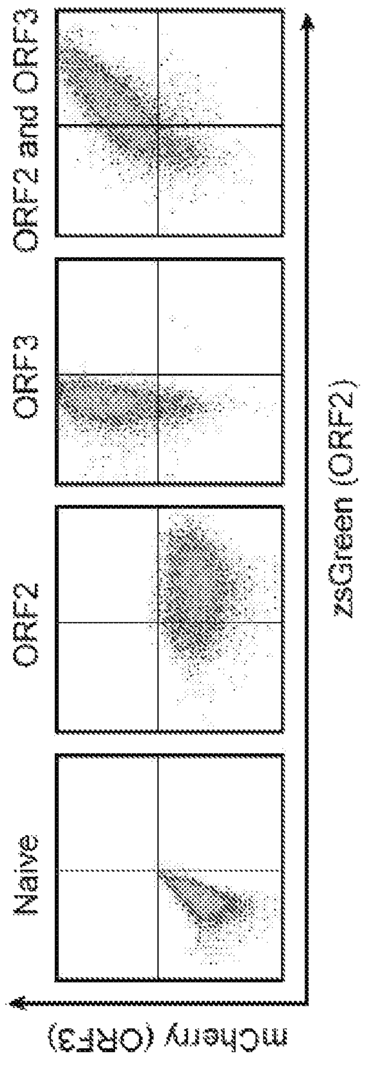

The present study indicated that ORF3 shares some similarities to known viroporins, (virally-encoded protein complexes that serve as functional ion channels). Like other viroporins, ORF3 is a small hydrophobic protein that tends to oligomerize in ER-derived membranes. Similar to class IA viroporins such as IAV M2 (Pinto, L. H., et al. *Cell* 69, 517-528 (1992)), HIV-1 Vpu (Cordes, F. S., et al. *Biochemistry* 41, 7359-7365 (2002)), or the coronavirus E protein (Wilson, L., et al. *Virology* 353, 294-306, (2006)), ORF3 has a short tail at the N-terminus that resides in the ER lumen and a long cytosolic tail at the C-terminus that is prone to phosphorylation at a serine in position 70 (Zafrullah, M., et al. *J Virol* 71, 9045-9053 (1997); Emerson, S. U., et al. *J Virol* 80, 10457-10464 (2006)). To enable direct analysis of ORF3's function, ORF2 and/or ORF3 were expressed lentivirally in HepG2C3A cells (FIG. 5), into which was subsequently transfected vitro transcribed RNA from a recombinant HEV genome derived from the KernowC1/p6 genome (Shukla, P, et al. *Proc Natl Acad Sci USA* 108, 2438-2443 (2011)) in which ORF2 and 3 were replaced by a secreted version of Gaussia luciferase (Glue), termed rHEVΔGRF2/3[Glue] (see also FIG. 5A). Supernatants collected from these cultures at day 5 post-transfection were then used to infect naïve HepG2C3A cells. The recombinant HEV subgenome replicated equally efficiently in all cells, irrespective of ORF2/3 expression (data not shown). In cells expressing ORF2 only, infectious virions assembled but were retained intracellularly (FIG. 2B). Only supernatants collected from HepG2C3A cells expressing HEV ORF2 and 3 together and not separately led to robust re-infection, as indicated by an approximately 35-45 fold increase in luciferase activity over background (FIG. 2A). These data are consistent with previous reports showing that ORF2 is essential for packaging and ORF3 for release of infectious particles (Yamada, et al. *J Gen Viral* 90, 1880-1891 (2009); Emerson, S. U., et al. *J Virol* 80, 10457-10464 (2006)).

Figure 3A:
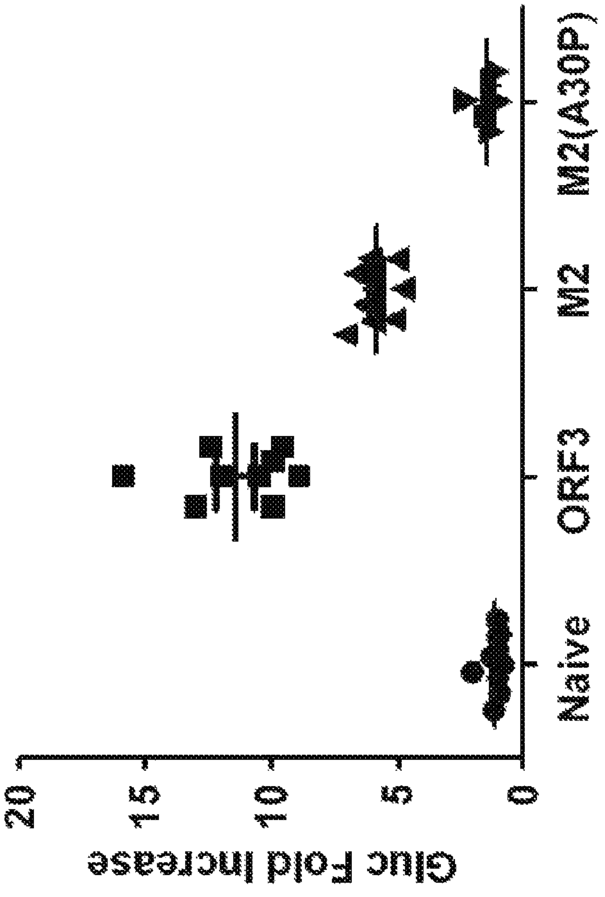
FIGS. 3A and 3B indicate that the HEV ORF3 protein has ion channel activity.

Next, it was determined whether ORF3's essential function in HEV release could be replaced by IAV M2, a well-characterized class IA viroporin (Pinto, L. H., et al. *Cell* 69, 517-528 (1992)). Notably, infection of HepG2C3A cells with supernatants from HepG2C3A cells in which transfection of rHEVΔORF2/3[Gluc] was complemented in trans with HEV ORF2 and IAV M2 resulted in a 5-8 fold increase in Gluc activity. This signal was approximately two fold lower than the 8-15 fold increase in Gluc activity resulting from infection with particles packaged in cells expressing HEV ORF2 and 3 (FIG. 3A). Furthermore, IAV M2-mediated HEV particle release was dependent on M2's ion channel activity as the INV M2(A30P) mutant, which abolishes its ion channel activity (Holsinger, L. J., et al. *J Virol* 68, 1551-1563 (1994)), did not support HEV particle egress. Taken together, these data suggest that HEV ORF3 functions as an ion channel.

Figure 3B:
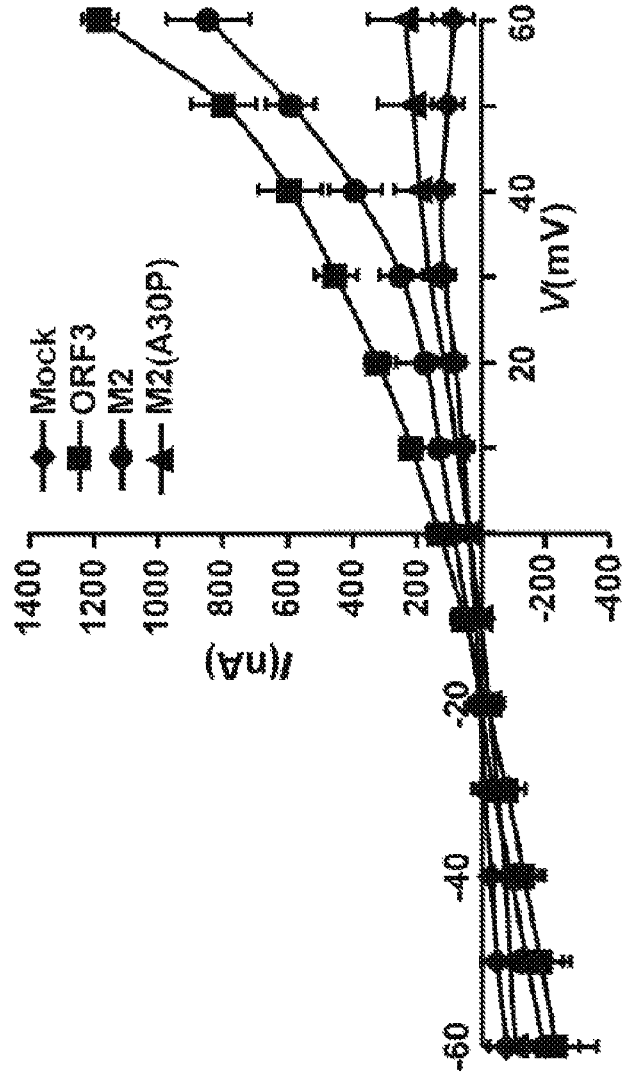
Figure 6A:
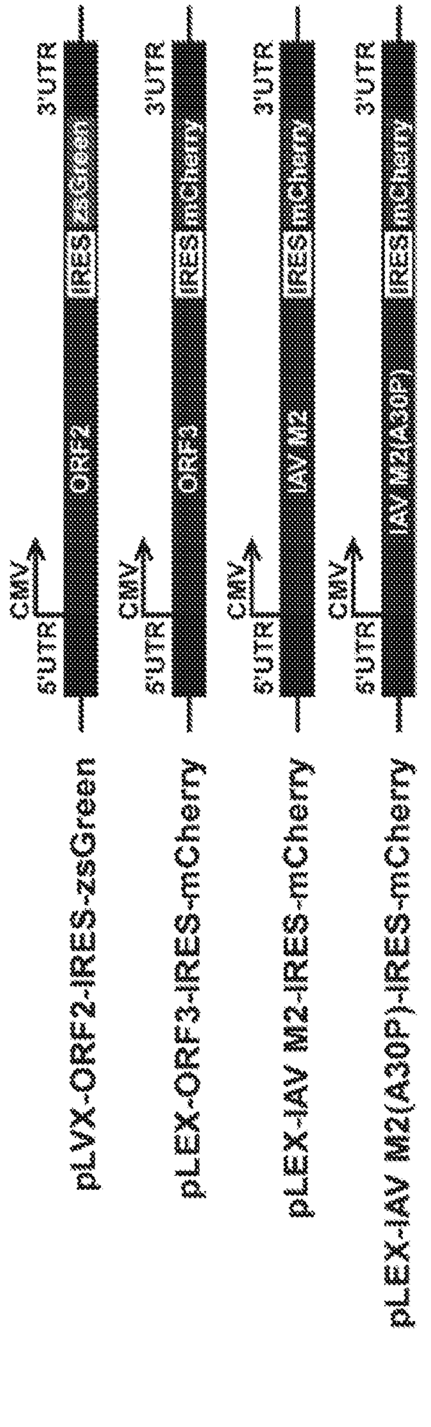
FIGS. 6A-6D illustrate constructs used in ORF3 functional studies and their expression.
Figure 6B:
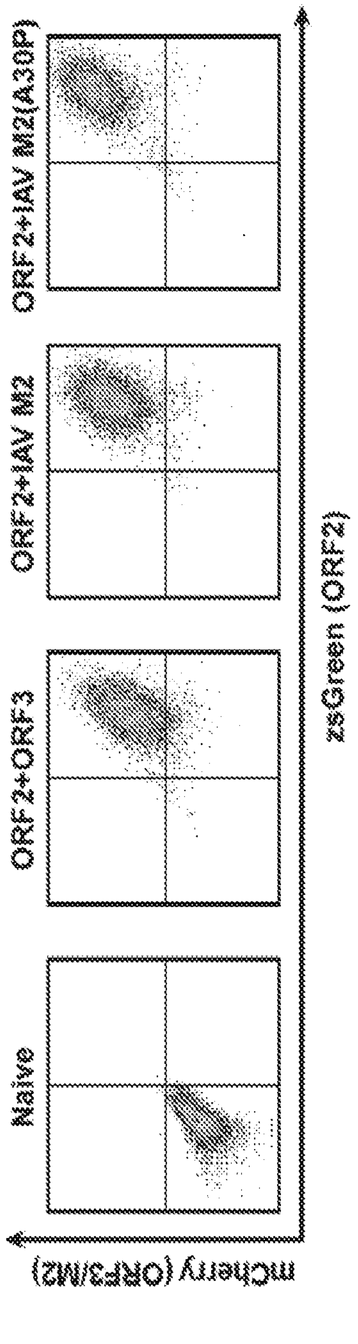
Figure 6C:
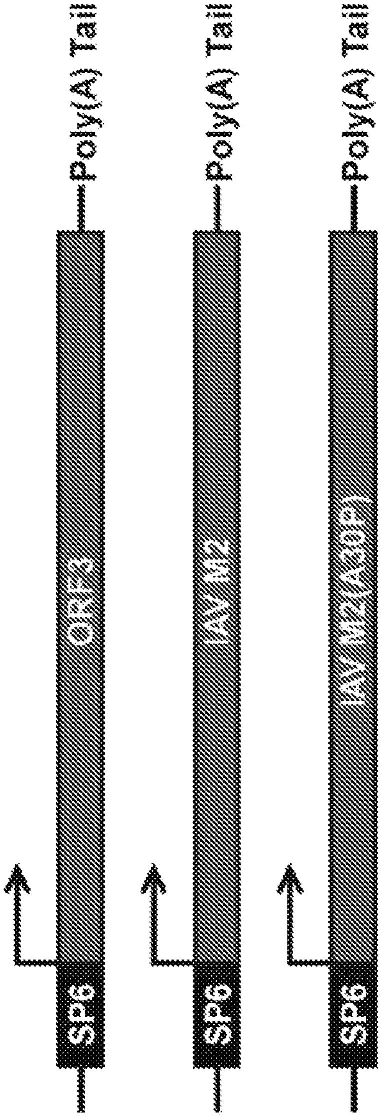
Figure 6D:
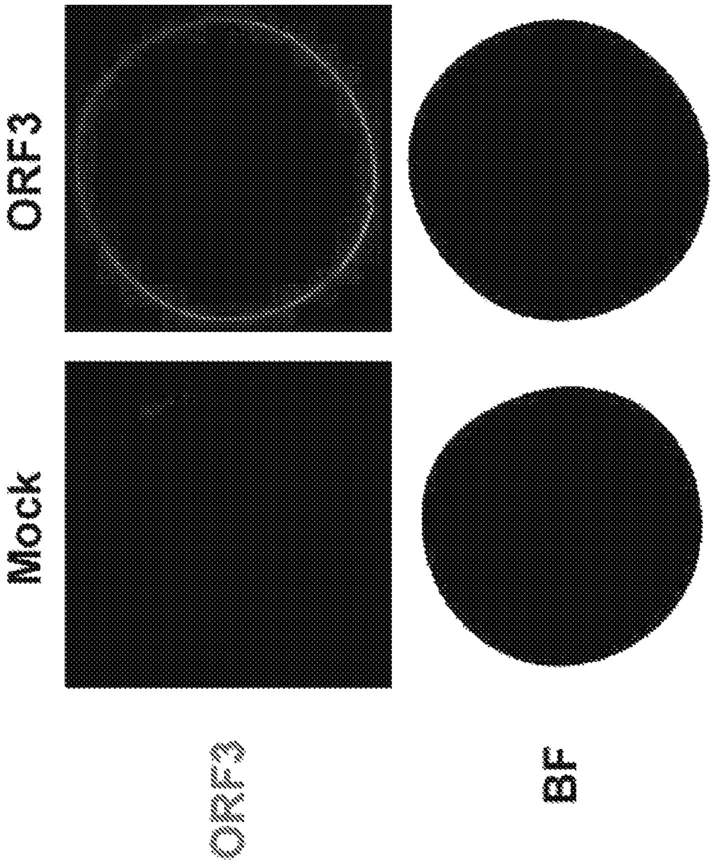

To directly test the ability of ORF3 to facilitate the flux of ions across membranes, a two-electrode voltage-clamp procedure was used in *Xenopus* (*X.*) *laevis* oocytes injected with wild-type ORF3, wild-type M2, or mutant M2(A30P) mRNAs. Cells were cultured for 2 days, and total membrane currents were measured. Immunofluorescence imaging confirmed expression of ORF3 (FIG. 6D) and the M2 proteins (data not shown) on the outer oocyte membrane. The currents of oocytes expressing the wild-type ORF3, M2, or M2 mutant proteins were studied by holding the membrane voltage of the oocytes at −60 mV and then changing the membrane voltage (between −90 and +60 mV) with a voltage-clamp pulse. This hyperpolarization induced an inward current with minimal time dependence that increased to a steady value immediately after the hyperpolarization pulse was applied. This current was significantly larger than the endogenous current evoked by identical changes of membrane voltage in control oocytes injected with M2 mutant (A30P) mRNA or mock injected but was very similar to that observed in oocytes injected with wild-type M2 mRNA (FIG. 3B). Together, these data demonstrate that HEV ORF3 serves as a functional ion channel.

Regions of ORF3 Important for Ion Channel and Viroporin Function

Figure 4A:
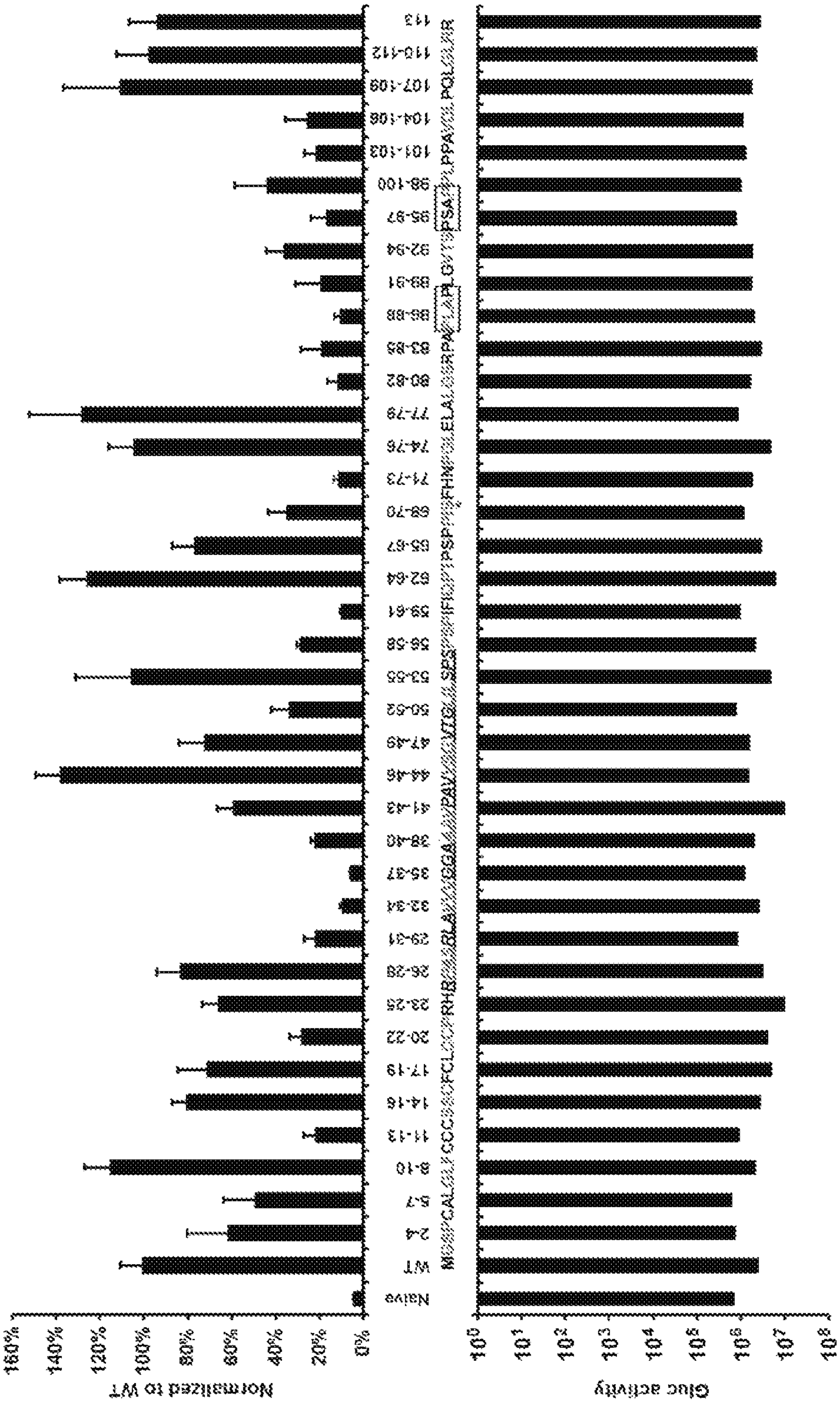
FIGS. 4A-4C demonstrate that HEV ORF3 ion channel activity is required for release of infectious HEV.
Figure 8B:
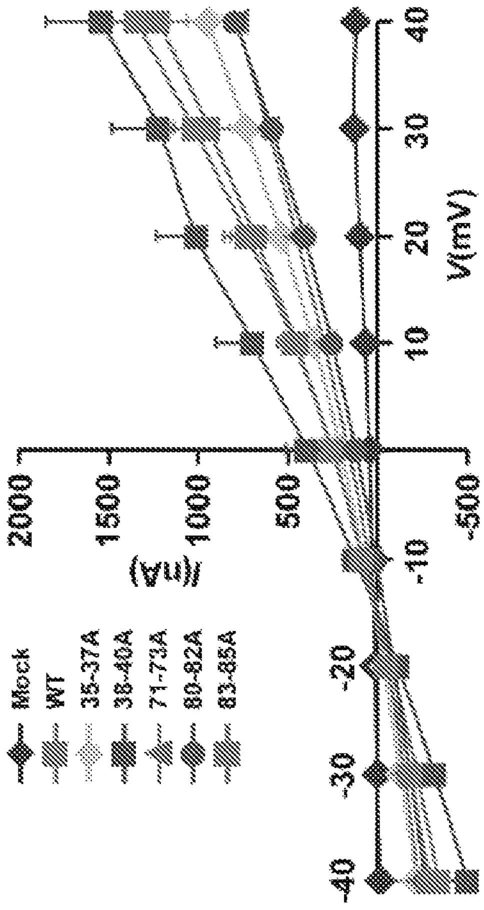
Figure 8A:
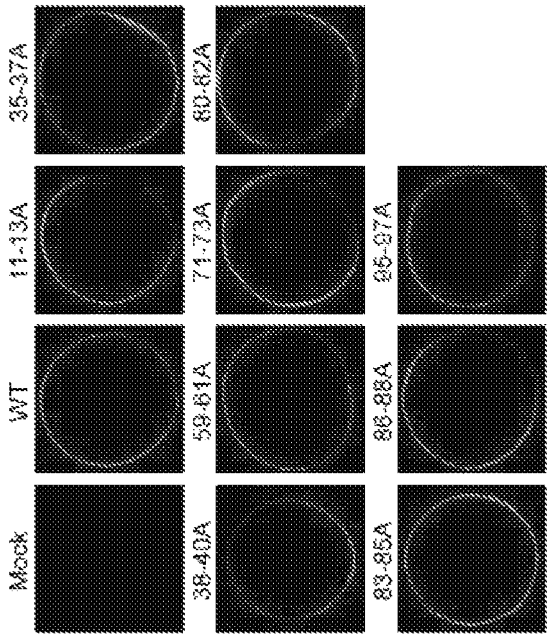
Figure 9:
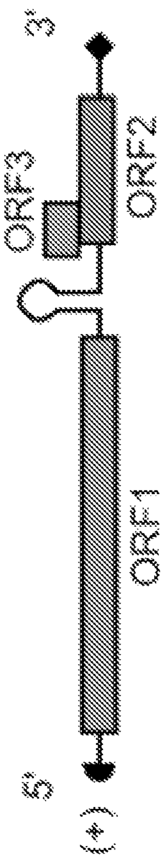
FIG. 9 shows the genomic organization of hepatitis E virus.
Figure 10A:
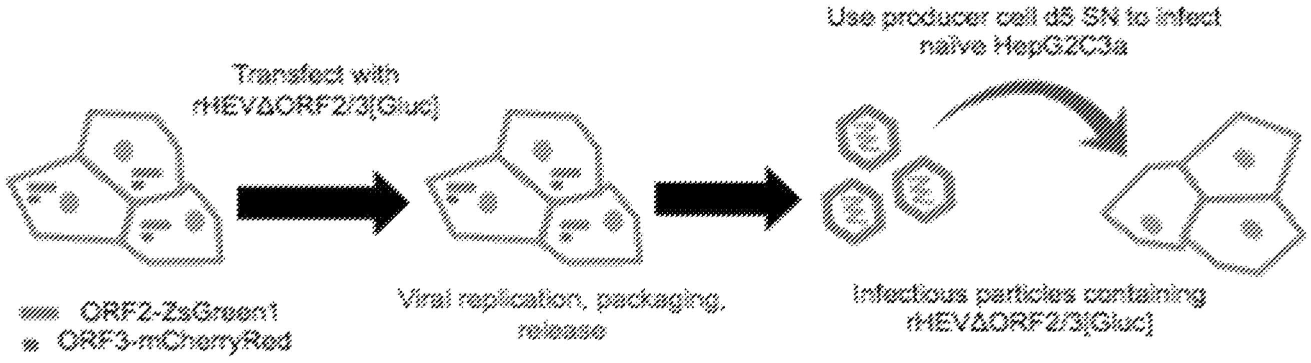
FIGS. 10A and 10B depict the development of a cell culture system for producing infectious virions in trans.
Figure 10B:
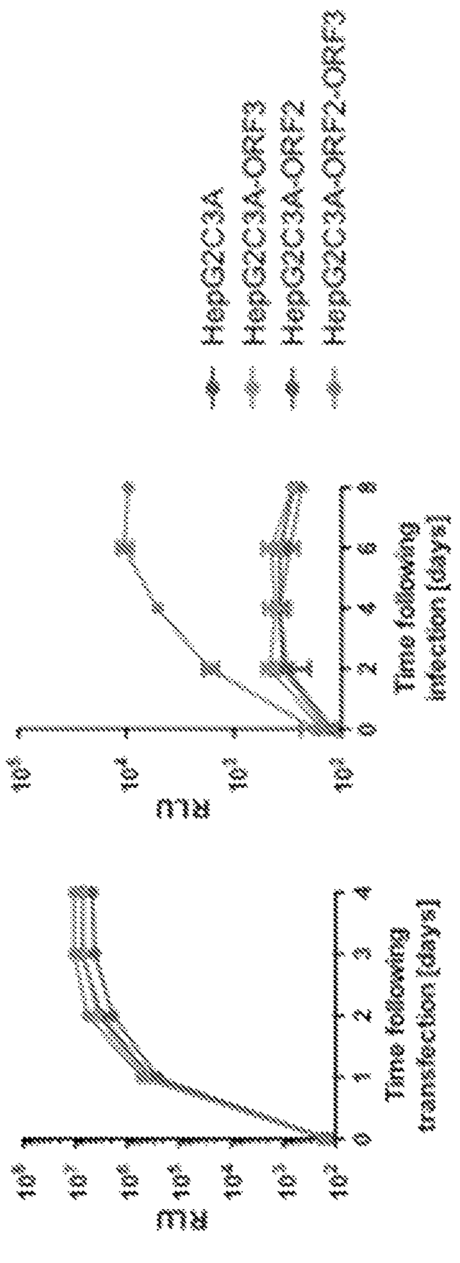

Regions within a HEV ORF3 protein important for release of infectious HEV particles and ion channel function were systematically identified. Alanine scanning mutagenesis was performed to change triplets of amino acids to alanine across the entire ORF3 protein. Lentiviral delivery of individual ORF3 mutants, along with unmodified ORF2, led to high expression of the proteins in the majority of HepG2C3A cells (data not shown). Dually transduced cells were subsequently transfected with rHEVΔORF2/3[Gluc] RNA and supernatants collected 5 days thereafter. To assess whether any of the ORF3 mutants affected release of HEV, supernatants were used to infect naïve HepG2C3A cells. Several positions led to ≥90% reduction in particle release as compared to HEV released from cells expressing wild-type ORF2 and ORF3 (FIG. 4A, top panel, FIG. 8C). In particular, the present study confirmed that ORF3 residues 86-89 and 95-98, each containing a PXXP motif previously shown to be necessary for HEV release (Kenney, S. P. et al. *J Virol* 86, 5637-5646 (2012); Kenney, S. P., et al. *Virology* 486, 198-208 (2015); Emerson, S. U. et al. *J Virol* 84, 9059-9069 (2010); Nagashima, S. et al. *J Gen Virol* 92, 269-278 (2011)), serve essential functions. In addition, mutations in positions 11-13, 29-40, 59-61, 71-73 and 80-85 reduced virion release by 80-95%. Gluc levels in the transfected cells were equivalent across all experimental conditions, demonstrating that the observed differences cannot be simply attributed to differences in RNA transfection and/or HEV replication efficiency in the different producer cells (FIG. 4A, bottom panel).

Figure 4C:
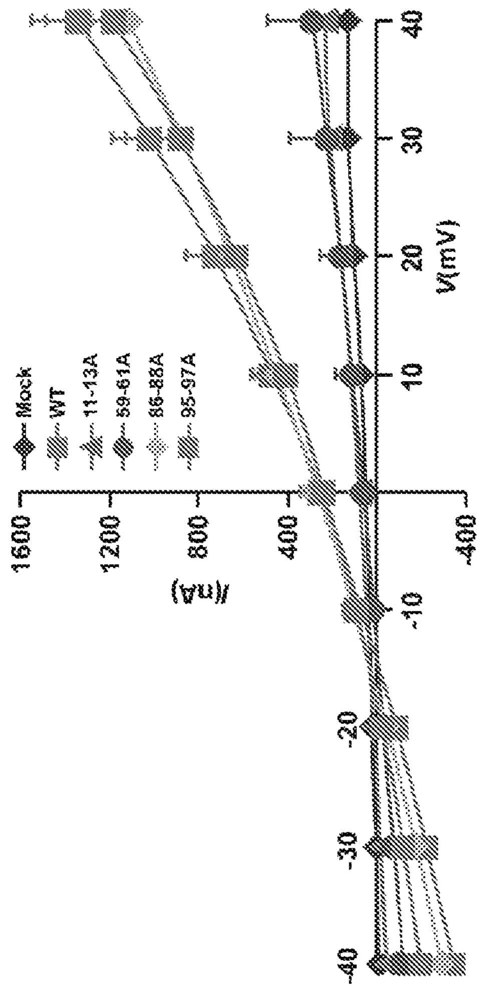
Figure 4B:
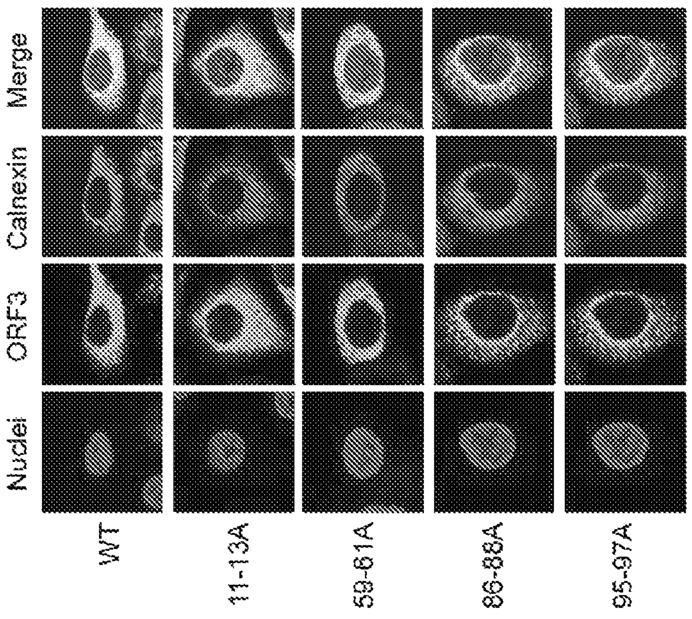
Figure 7A:
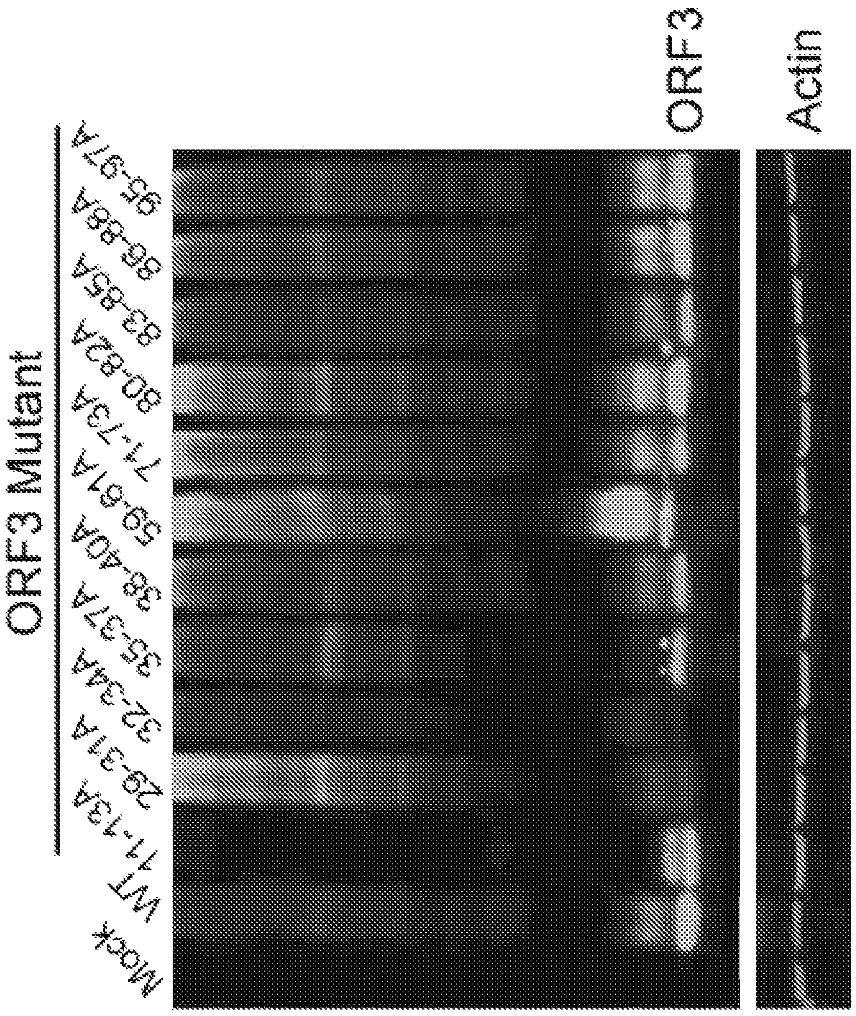
FIGS. 7A and 7B show expression of ORF3 mutant constructs.
Figure 7B:
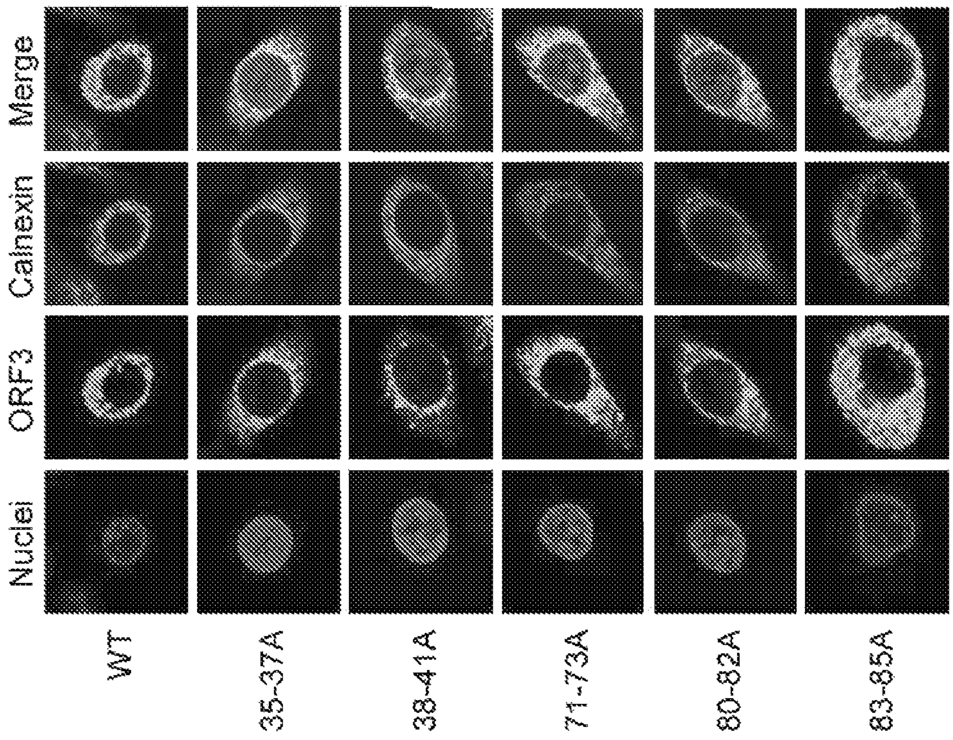

ORF3 mutants that simply affected protein stability were eliminated from the analysis. Western blots of lysates from HepG2C3A cells expressing HA-tagged ORF3 showed that all mutants except ORF3[RLA29-31AAA] and ORF3 [VVV32-34AAA] could readily be detected with an anti-HA antibody (FIG. 7A) and those that did express well, with the exception of ORF3[CCC11-13AAA, still formed higher molecular weight complexes indicative of multimerized ORF3. All stable mutants were then subjected to voltage-clamp experiments. Notably, ORF3[CCC11-13AAA] and ORF3[IF159-61AAA] exhibited a significant decrease in ion flux across the membrane as compared to oocytes expressing wild-type ORF3 (FIG. 4C). ORF3[PLA86-88AAA] and ORF3[PSA95-97AAA], which had alanine triplets disrupting the PXXP motifs critical for interactions with components of the ESCRT machinery and thereby interfere with the release of infectious particles through the vacuolar protein secretion pathway (Emerson, S. U. et al. *J Virol* 84, 9059-9069 (2010); Nagashima, S. et al. *J Gen Vivol* 92, 269-278 (2011); Yamada, K. et al *J Gen Vivol* 90, 1880-1891 (2009); Kenney, S. P., et al. *Virology* 486, 198-208 (2015); Nagashima, S. et al. *J Gen Virol* 92, 2838-2848 (2011); Surjit, M., et al. *J Biol Chem* 281, 8135-8142 (2006)), did not diminish ion channel activity. Of note, none of these mutants, including ORF3[CCC11-13AAA] and ORF3[IFI59-61AAA], displayed vastly different subcellular localization as compared to wild-type ORF3 (FIG. 4B and FIG. 7B). Thus, residues 11-13 and 59-61 likely reside within regions important for ORF3's ion channel function.

Altogether, the data shown herein demonstrate that ORF3's ion channel activity is important for particle release, which is an additional, distinct function from the previously described, essential interactions of HEV ORF3 with components of the ESCRT pathway.

Testing Known Ion Channel Inhibitors for Activity Against MEV ORF3

Figure 11:
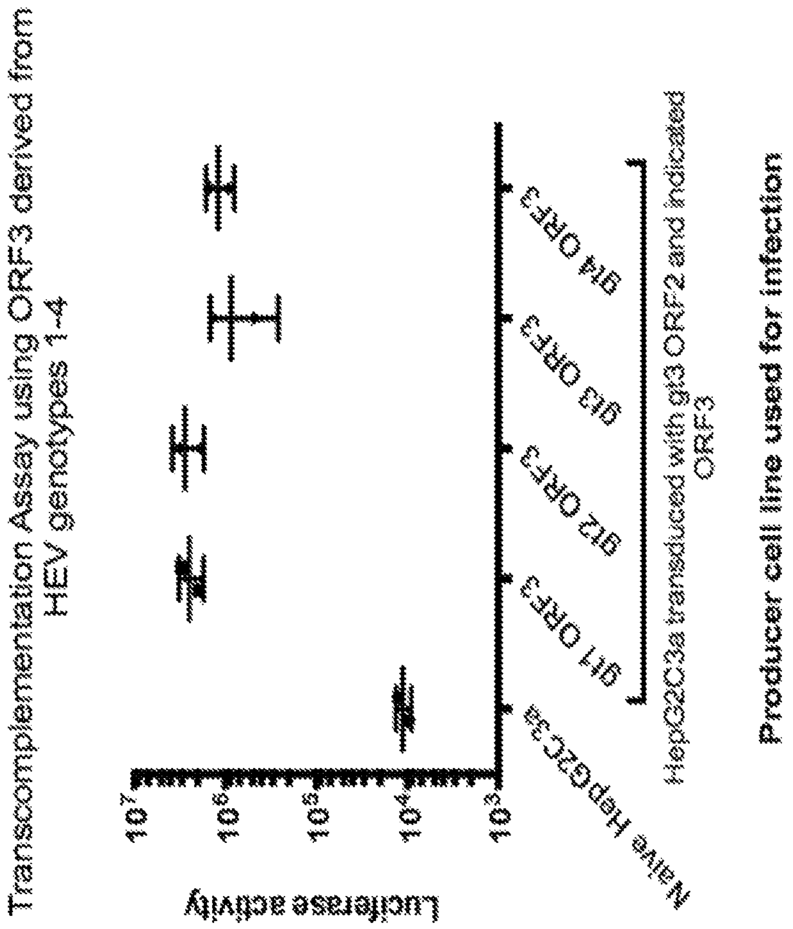
FIG. 11 shows that ORF1 and ORF2 from an HEV gt3 strain were transcomplemented with ORF3 derived from HEV gts 1-4. Supernatant was collected and used to infect naïve HepG2C3A cells, producing comparable levels of infection regardless of the ORF3 variant used.

Using the transcomplementation platform described herein, it was demonstrated that HEV ORF3 exhibits ion channel activity (see hereinabove and Ding et al, PNAS 114(5), 1147-1152 (2017), the contents of which are incorporated herein by reference in their entirety. It was shown that ORF3's viroporin function can be substituted in trans with other class Ia viroporins, specifically the influenza A virus (IAV) M2 protein. Using the transcomplementation platform, ORF3 from different HEV genotypes (gts) known to infect humans (gts 1, 2, 3, or 4) was delivered in trans with ORF1 and ORF2 from gt 3. Interestingly, HEV particle release is equivalent when the genotype of ORF3 is mismatched with ORF1/2 (FIG. 11). These data collectively show that ORF3 operates in a viral genotype-independent fashion.

Figure 12B:
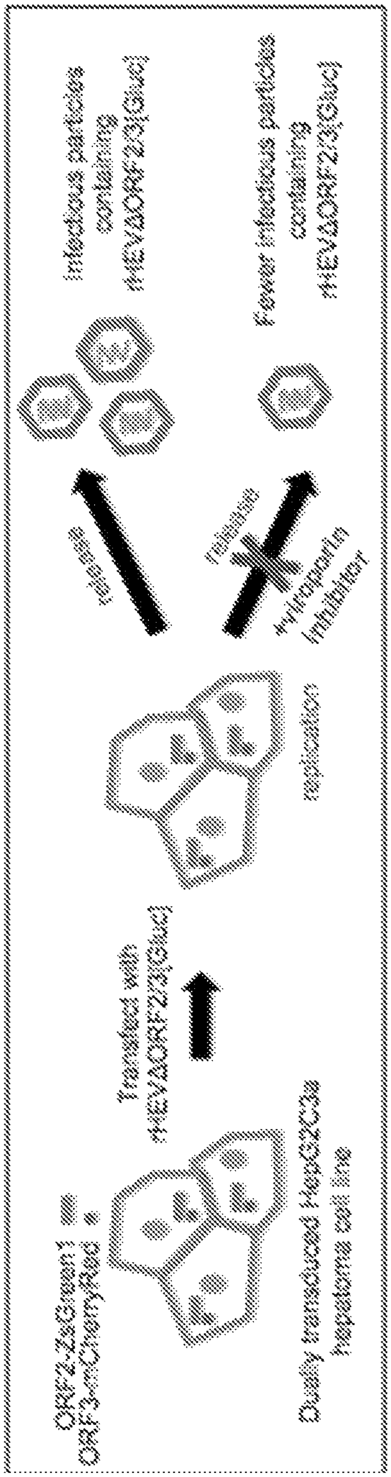
Figure 12C:
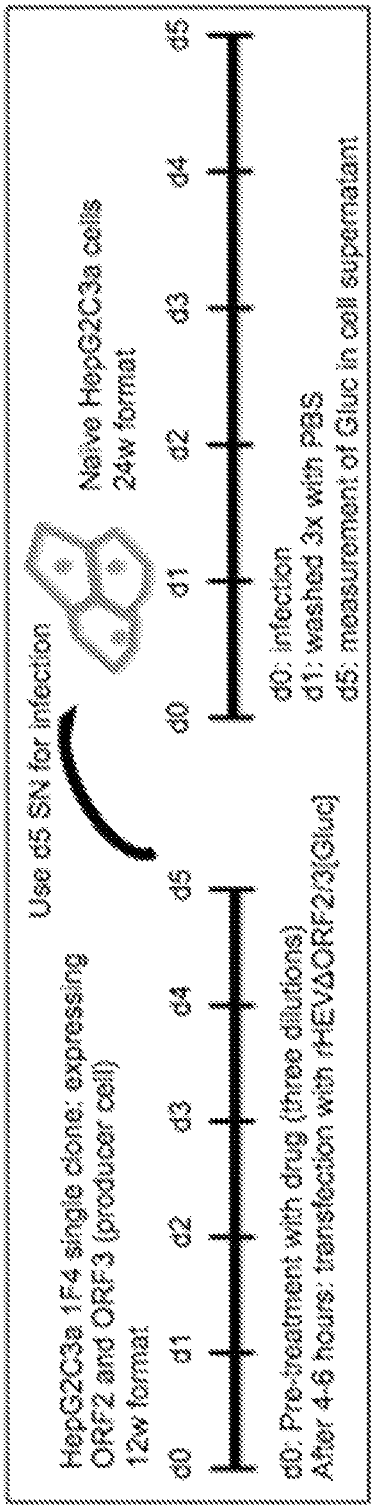
Figure 13A:
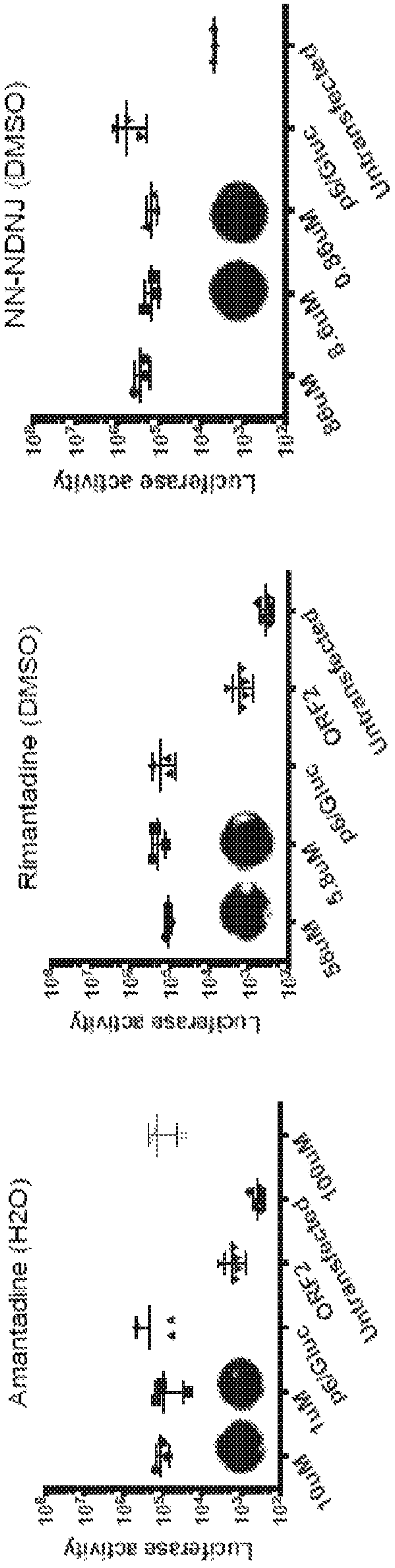
FIGS. 13A-13C shows the results from viroporin inhibitor testing. Supernatant was collected from producer 1F4 HepG2C3a cells treated with varying dilutions of ion channel inhibitors, and used to infect naïve HepG2C3a cells. The infected cells were washed 12 h post infection, and Gluc levels were measured in the supernatants of these cells on day 5 post-infection (shown above). Cells were infected in triplicate in a 24 w format. None of the ion channel inhibitors significantly decreased release of infectious particles compared to the positive control (producer cells transfected with p6/Gluc in the absence of drug). Crystal violet staining on drug-treated cells was performed as a rough measure of cytotoxicity.
Figure 13B:
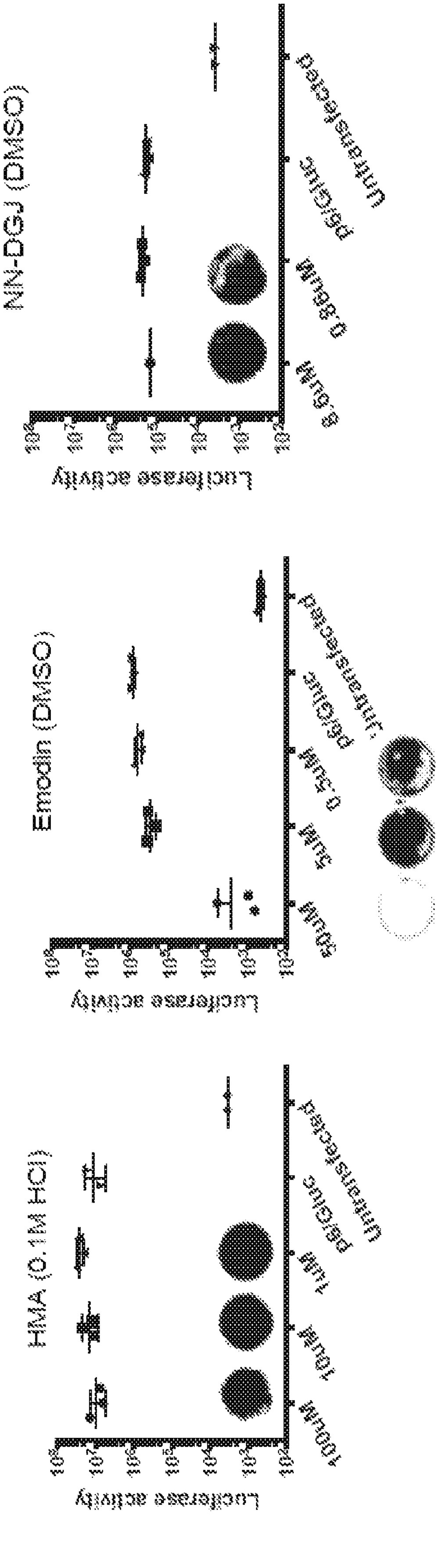
Figure 13C:
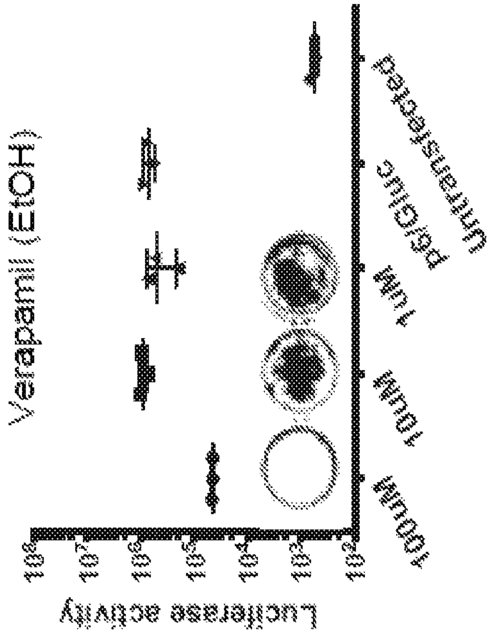

Known ion channel inhibitors were tested for anti-viral activity against HEV using the transcomplementation platform (FIGS. 12A-12C). Of the known inhibitors tested, none significantly inhibited viral particle release, suggesting that HEV ORF3-specific targets are likely needed to interfere efficiently with viral egress (FIGS. 13A-13C).

The teachings of all patents, published applications and references cited herein are incorporated by reference in their entirety.

While this invention has been particularly shown and described with references to example embodiments thereof, it will be understood by those skilled in the art that various changes in form and details may be made therein without departing from the scope of the invention encompassed by the appended claims.

What is claimed is:

1. A method of identifying an agent that inhibits hepatitis E virus (HEV) infectivity, comprising:

a) introducing into a cell culture 1) a nucleic acid that comprises an HEV open reading frame 2 (ORF2) nucleotide sequence, 2) a nucleic acid that comprises an HEV ORF3 nucleotide sequence, and 3) a nucleic acid that i) comprises a reporter gene and an HEV ORF1 nucleotide sequence and ii) lacks HEV ORF2 and ORF3 nucleotide sequences;

b) contacting the cell culture in step a) with an agent to be tested for anti-HEV activity;

c) harvesting the cell culture media from the cell culture that has been contacted with the agent;

d) combining the harvested media with a naïve cell culture;

e) measuring a level of activity of the reporter gene in the naïve cell culture; and f) comparing the level of reporter activity in the naïve cell culture measured in step e) to a reference activity level, wherein a decrease in measured activity level as compared to the reference activity level indicates that the agent inhibits HEV infectivity.

2. The method of claim 1, wherein ORF2 and ORF3 are introduced into the cells in the cell culture on a single vector.

3. The method of claim 1, wherein ORF2 and ORF3 are introduced into the cells in the cell culture on separate vectors.

4. The method of claim 1, wherein the nucleic acid that i) comprises ORF1 and a reporter gene and ii) lacks ORF2 and ORF3 is introduced as an RNA molecule.

5. The method of claim 1, wherein the reporter encodes a luciferase enzyme.

6. The method of claim 1, wherein the cell culture introduced with nucleic acid comprises or is derived from a hepatocyte.

7. The method of claim 1, wherein the naïve cell culture comprises or is derived from a hepatocyte.

8. The method of claim 1, wherein the agent binds to any one or more regions of ORF3 protein comprising SEQ ID NO: 1 at amino acid positions 11-13, 29-40, 59-61, 71-73, 80-85, 86-89, or 95-98 of SEQ ID NO: 1.

9. The method of claim 1, wherein the agent inhibits the release of infectious HEV.

10. The method of claim 6, wherein the cell culture comprises or is derived from a HepG2C3a cell.

11. The method of claim 7, wherein the naïve cell culture comprises or is derived from a HepG2C3a cell.

* * * * *